(12) United States Patent
Schaefer et al.

(10) Patent No.: US 12,616,501 B2
(45) Date of Patent: May 5, 2026

(54) SURGICAL INTRODUCER WITH GUIDANCE SYSTEM RECEPTACLE

(71) Applicant: Vycor Medical, Inc., Boca Raton, FL (US)

(72) Inventors: Robert Schaefer, Riverside, CA (US); David Cantor, Rome (IT)

(73) Assignee: Vycor Medical, Inc., Boca Raton, FL (US)

( * ) Notice: Subject to any disclaimer, the term of this patent is extended or adjusted under 35 U.S.C. 154(b) by 50 days.

(21) Appl. No.: 18/947,714

(22) Filed: Nov. 14, 2024

(65) Prior Publication Data

US 2025/0064480 A1 Feb. 27, 2025

Related U.S. Application Data

(63) Continuation of application No. 17/473,282, filed on Sep. 13, 2021, now Pat. No. 12,178,469, which is a
(Continued)

(51) Int. Cl.
| | |
|---|---|
| *A61B 17/34* | (2006.01) |
| *A61B 34/20* | (2016.01) |
(Continued)

(52) U.S. Cl.
CPC ...... *A61B 17/3421* (2013.01); *A61B 17/3423* (2013.01); *A61B 34/20* (2016.02);
(Continued)

(58) Field of Classification Search
CPC ....... A61B 1/32; A61B 17/02; A61B 17/0218; A61B 17/3415; A61B 17/3417; A61B 17/3421; A61B 34/20
See application file for complete search history.

(56) References Cited

U.S. PATENT DOCUMENTS

| | | | |
|---|---|---|---|
| 1,849,701 | A | 3/1932 | Allyn |
| 2,769,441 | A | 11/1956 | Abramson |
(Continued)

FOREIGN PATENT DOCUMENTS

| | | |
|---|---|---|
| CN | 201879787 U | 6/2011 |
| CN | 203724147 U | 7/2014 |
(Continued)

OTHER PUBLICATIONS

"Neuronavigation", from Wikipedia, dated Jul. 30, 2014, 2 pages.
(Continued)

*Primary Examiner* — Andrew Yang
(74) *Attorney, Agent, or Firm* — CM Law, LLP

(57) ABSTRACT

A surgical introducer system having an outer introducer sidewall extending along a longitudinal axis from a proximal introducer end to a distal introducer end, an inner introducer sidewall extending within the outer introducer sidewall along the longitudinal axis and forming an introducer passage extending in a distal direction from a proximal passage opening at the proximal introducer end to an introducer passage end wall located proximal to the distal introducer end, and an end wall passage extending from the introducer passage end wall towards the distal introducer end. The introducer end wall passage joins the introducer end wall at one or more end wall edges defining an axial stop ring configured to contact the distal tip of a navigation probe between the probe shaft and a terminal end of the distal probe tip at a line of contact to thereby prevent movement of the navigation probe in the distal direction.

20 Claims, 23 Drawing Sheets

Related U.S. Application Data continuation-in-part of application No. 16/740,858, filed on Jan. 13, 2020, now Pat. No. 11,517,347, which is a continuation of application No. 15/805,821, filed on Nov. 7, 2017, now Pat. No. 10,543,016, which is a continuation-in-part of application No. 15/372,890, filed on Dec. 8, 2016, now Pat. No. 10,376,258.

(60) Provisional application No. 62/418,507, filed on Nov. 7, 2016.

(51) Int. Cl.

| | |
|---|---|
| *A61B 90/10* | (2016.01) |
| *A61B 90/11* | (2016.01) |
| *A61B 90/57* | (2016.01) |
| *A61B 17/02* | (2006.01) |
| *A61B 90/00* | (2016.01) |

(52) U.S. Cl.
CPC ............. *A61B 90/10* (2016.02); *A61B 90/11* (2016.02); *A61B 90/57* (2016.02); *A61B 17/0218* (2013.01); *A61B 2017/3429* (2013.01); *A61B 2017/347* (2013.01); *A61B 2034/2051* (2016.02); *A61B 2034/2055* (2016.02); *A61B 2090/103* (2016.02); *A61B 2090/3983* (2016.02)

(56) References Cited

U.S. PATENT DOCUMENTS

| | | | |
|---|---|---|---|
| 2,922,415 | A | 1/1960 | Campagna |
| 3,417,746 | A | 12/1968 | Moore |
| 3,608,547 | A | 9/1971 | Sato |
| 3,626,471 | A | 12/1971 | Florin |
| 3,690,323 | A | 9/1972 | Wortman et al. |
| 3,766,910 | A | 10/1973 | Lake |
| 3,789,829 | A | 2/1974 | Hasson |
| 3,882,855 | A | 5/1975 | Schulte et al. |
| 3,888,117 | A | 6/1975 | Lewis |
| 4,263,900 | A | 4/1981 | Nicholson |
| 4,312,353 | A | 1/1982 | Shahbabian |
| 4,386,602 | A | 6/1983 | Sheldon et al. |
| 4,502,468 | A | 3/1985 | Burgin |
| 4,585,438 | A | 4/1986 | Makler |
| 4,636,199 | A | 1/1987 | Victor |
| 4,638,798 | A | 1/1987 | Sheldon et al. |
| 4,742,815 | A | 5/1988 | Ninan et al. |
| 4,931,039 | A | 6/1990 | Coe et al. |
| 4,945,896 | A | 8/1990 | Gade |
| 5,052,373 | A | 10/1991 | Michelson |
| 5,135,526 | A | 8/1992 | Zinnanti et al. |
| 5,160,323 | A | 11/1992 | Andrew |
| 5,183,464 | A | 2/1993 | Dubrul et al. |
| 5,230,623 | A | 7/1993 | Guthrie et al. |
| 5,249,568 | A | 10/1993 | Brefka et al. |
| 5,251,127 | A | 10/1993 | Raab |
| 5,256,149 | A | 10/1993 | Banik et al. |
| 5,271,380 | A | 12/1993 | Riek et al. |
| 5,275,583 | A | 1/1994 | Crainich |
| 5,284,130 | A | 2/1994 | Ratliff |
| 5,305,203 | A | 4/1994 | Raab |
| 5,320,611 | A | 6/1994 | Bonutti et al. |
| 5,334,150 | A | 8/1994 | Kaali |
| 5,356,421 | A | 10/1994 | Castro |
| 5,376,076 | A | 12/1994 | Kaali |
| 5,380,291 | A | 1/1995 | Kaali |
| 5,409,453 | A | 4/1995 | Lundquist et al. |
| 5,431,151 | A | 7/1995 | Riek et al. |
| 5,431,676 | A | 7/1995 | Dubrul et al. |
| 5,441,041 | A | 8/1995 | Sauer et al. |
| 5,445,142 | A | 8/1995 | Hassler |
| 5,467,762 | A | 11/1995 | Sauer et al. |
| 5,513,238 | A | 4/1996 | Leber et al. |
| 5,540,711 | A | 7/1996 | Kieturakis et al. |
| 5,551,947 | A | 9/1996 | Kaali |
| 5,555,283 | A | 9/1996 | Shui et al. |
| 5,562,696 | A | 10/1996 | Nobles et al. |
| 5,569,160 | A | 10/1996 | Sauer et al. |
| D377,093 | S | 12/1996 | Michelson |
| 5,591,192 | A | 1/1997 | Privitera et al. |
| 5,609,562 | A | 3/1997 | Kaali |
| 5,658,236 | A | 8/1997 | Sauer et al. |
| 5,662,111 | A | 9/1997 | Cosman |
| 5,665,072 | A | 9/1997 | Yoon |
| 5,676,673 | A | 10/1997 | Ferre et al. |
| 5,685,820 | A | 11/1997 | Riek et al. |
| 5,702,761 | A | 12/1997 | DiChiara et al. |
| 5,738,628 | A | 4/1998 | Sierocuk et al. |
| 5,748,703 | A | 5/1998 | Cosman |
| 5,748,767 | A | 5/1998 | Raab |
| 5,762,629 | A | 6/1998 | Kambin |
| 5,778,043 | A | 7/1998 | Cosman |
| 5,782,807 | A | 7/1998 | Falvai et al. |
| 5,785,648 | A | 7/1998 | Min |
| 5,792,044 | A | 8/1998 | Foley et al. |
| 5,800,352 | A | 9/1998 | Ferre et al. |
| 5,803,089 | A | 9/1998 | Ferre et al. |
| 5,829,444 | A | 11/1998 | Ferre et al. |
| 5,846,249 | A | 12/1998 | Thompson |
| 5,848,967 | A | 12/1998 | Cosman |
| 5,860,996 | A | 1/1999 | Urban et al. |
| 5,873,822 | A | 2/1999 | Ferre et al. |
| 5,891,157 | A | 4/1999 | Day et al. |
| 5,902,272 | A | 5/1999 | Eggers et al. |
| 5,921,992 | A | 7/1999 | Costales et al. |
| 5,947,981 | A | 9/1999 | Cosman |
| 5,967,970 | A | 10/1999 | Cowan et al. |
| 5,967,980 | A | 10/1999 | Ferre et al. |
| 5,971,997 | A | 10/1999 | Guthrie et al. |
| 6,005,919 | A | 12/1999 | Kooy et al. |
| 6,006,126 | A | 12/1999 | Cosman |
| 6,007,481 | A | 12/1999 | Riek et al. |
| 6,041,101 | A | 3/2000 | Kooy et al. |
| 6,047,218 | A | 4/2000 | Whayne et al. |
| 6,083,191 | A | 7/2000 | Rose et al. |
| 6,093,145 | A | 7/2000 | Berg et al. |
| 6,096,038 | A | 8/2000 | Michelson |
| 6,120,465 | A | 9/2000 | Guthrie et al. |
| 6,129,685 | A | 10/2000 | Howard |
| 6,142,931 | A | 11/2000 | Kaji et al. |
| 6,156,054 | A | 12/2000 | Zadno-Azizi et al. |
| 6,159,178 | A | 12/2000 | Sharkawy et al. |
| 6,167,295 | A | 12/2000 | Cosman |
| 6,175,756 | B1 | 1/2001 | Ferre et al. |
| 6,179,826 | B1 | 1/2001 | Aebischer et al. |
| 6,214,017 | B1 | 4/2001 | Stoddard et al. |
| 6,221,078 | B1 | 4/2001 | Bylsma |
| 6,224,599 | B1 | 5/2001 | Bayham et al. |
| 6,228,059 | B1 | 5/2001 | Astarita |
| 6,236,875 | B1 | 5/2001 | Bucholz et al. |
| 6,245,052 | B1 | 6/2001 | Orth et al. |
| 6,256,859 | B1 | 7/2001 | Stoddard et al. |
| 6,259,943 | B1 | 7/2001 | Cosman et al. |
| 6,275,725 | B1 | 8/2001 | Cosman |
| 6,277,069 | B1 | 8/2001 | Gray |
| 6,278,766 | B1 | 8/2001 | Kooy et al. |
| 6,283,912 | B1 | 9/2001 | Hu et al. |
| 6,293,952 | B1 | 9/2001 | Brosens et al. |
| 6,296,647 | B1 | 10/2001 | Robionek et al. |
| 6,312,443 | B1 | 11/2001 | Stone |
| 6,326,875 | B1 | 12/2001 | Tuovinen |
| 6,331,180 | B1 | 12/2001 | Cosman et al. |
| 6,341,231 | B1 | 1/2002 | Ferre et al. |
| 6,351,659 | B1 | 2/2002 | Vilsmeier |
| 6,351,661 | B1 | 2/2002 | Cosman |
| 6,359,959 | B1 | 3/2002 | Butler et al. |
| 6,364,832 | B1 | 4/2002 | Propp |
| 6,371,964 | B1 | 4/2002 | Vargas et al. |
| 6,374,135 | B1 | 4/2002 | Bucholz |
| 6,383,191 | B1 | 5/2002 | Zdeblick et al. |
| 6,405,072 | B1 | 6/2002 | Cosman |

(56) References Cited

U.S. PATENT DOCUMENTS

| | | | |
|---|---|---|---|
| 6,409,686 | B1 | 6/2002 | Guthrie et al. |
| 6,416,520 | B1 | 7/2002 | Kynast et al. |
| 6,425,859 | B1 | 7/2002 | Foley et al. |
| 6,428,556 | B1 | 8/2002 | Chin |
| 6,445,944 | B1 | 9/2002 | Ostrovsky |
| 6,459,769 | B1 | 10/2002 | Cosman |
| 6,461,330 | B1 | 10/2002 | Miyagi |
| 6,478,028 | B1 | 11/2002 | Paolitto et al. |
| 6,478,806 | B2 | 11/2002 | McFarlane |
| 6,551,240 | B2 | 4/2003 | Henzler |
| 6,565,574 | B2 | 5/2003 | Michelson |
| 6,589,211 | B1 | 7/2003 | MacLeod |
| 6,595,917 | B2 | 7/2003 | Nieto |
| 6,596,008 | B1 | 7/2003 | Kambin |
| 6,599,292 | B1 | 7/2003 | Ray |
| 6,602,227 | B1 | 8/2003 | Cimino et al. |
| 6,605,036 | B1 | 8/2003 | Wild |
| 6,613,038 | B2 | 9/2003 | Bonutti et al. |
| 6,654,999 | B2 | 12/2003 | Stoddard et al. |
| 6,662,036 | B2 | 12/2003 | Cosman |
| 6,669,685 | B1 | 12/2003 | Rizoiu et al. |
| 6,675,040 | B1 | 1/2004 | Cosman |
| 6,685,630 | B2 | 2/2004 | Sauer et al. |
| 6,761,687 | B1 | 7/2004 | Doshi et al. |
| D495,053 | S | 8/2004 | Laun |
| 6,863,674 | B2 | 3/2005 | Kasahara et al. |
| 6,896,680 | B2 | 5/2005 | Michelson |
| 6,942,634 | B2 | 9/2005 | Odland |
| 7,081,089 | B2 | 7/2006 | Bonadio et al. |
| 7,153,304 | B2 | 12/2006 | Robie et al. |
| 7,235,084 | B2 | 6/2007 | Skakoon et al. |
| 7,449,011 | B2 | 11/2008 | Wenchell et al. |
| 7,474,820 | B2 | 1/2009 | Vayser et al. |
| 7,479,150 | B2 | 1/2009 | Rethy et al. |
| 7,510,524 | B2 | 3/2009 | Vayser et al. |
| 7,686,492 | B2 | 3/2010 | Vayser et al. |
| 7,799,035 | B2 | 9/2010 | Krueger et al. |
| 8,360,970 | B2 | 1/2013 | Mangiardi |
| 8,386,052 | B2 | 2/2013 | Harris et al. |
| 8,409,083 | B2 | 4/2013 | Mangiardi |
| 8,608,650 | B2 | 12/2013 | Mangiardi |
| 8,608,769 | B2 | 12/2013 | Kahle et al. |
| 8,679,088 | B2 | 3/2014 | Abrahams |
| 9,216,015 | B2 | 12/2015 | Wilson |
| 9,307,969 | B2 | 4/2016 | Novak et al. |
| 10,258,316 | B2 | 4/2019 | Rhad et al. |
| 10,327,748 | B2 | 6/2019 | Gifford et al. |
| 10,376,258 | B2 | 8/2019 | Cantor et al. |
| 10,543,016 | B2 | 1/2020 | Cantor et al. |
| 2001/0010002 | A1 | 7/2001 | Michelson |
| 2001/0011175 | A1 | 8/2001 | Hunter et al. |
| 2001/0027271 | A1 | 10/2001 | Franck et al. |
| 2001/0037050 | A1 | 11/2001 | Lemperle |
| 2002/0022764 | A1 | 2/2002 | Smith et al. |
| 2002/0151769 | A1 | 10/2002 | Kim |
| 2002/0161366 | A1 | 10/2002 | Robie et al. |
| 2003/0040753 | A1 | 2/2003 | Daum et al. |
| 2003/0073934 | A1 | 4/2003 | Putz |
| 2003/0139648 | A1 | 7/2003 | Foley et al. |
| 2003/0145865 | A1 | 8/2003 | Sterman et al. |
| 2004/0024291 | A1 | 2/2004 | Zinkel |
| 2004/0059375 | A1 | 3/2004 | Ginn et al. |
| 2004/0068172 | A1 | 4/2004 | Nowinski et al. |
| 2004/0097792 | A1 | 5/2004 | Moll et al. |
| 2004/0102804 | A1 | 5/2004 | Chin |
| 2004/0186346 | A1 | 9/2004 | Smith et al. |
| 2004/0230100 | A1 | 11/2004 | Shluzas |
| 2005/0273132 | A1 | 12/2005 | Shluzas et al. |
| 2005/0277811 | A1 | 12/2005 | Richards et al. |
| 2006/0041270 | A1 | 2/2006 | Lenker et al. |
| 2006/0122462 | A1 | 6/2006 | Roth et al. |
| 2006/0212062 | A1 | 9/2006 | Farascioni |
| 2006/0287583 | A1 | 12/2006 | Mangiardi |
| 2007/0129747 | A1 | 6/2007 | Dorman |
| 2007/0135679 | A1 | 6/2007 | Hunt et al. |

| | | | |
|---|---|---|---|
| 2007/0232874 | A1 | 10/2007 | Ince |
| 2008/0100061 | A1 | 5/2008 | Sage et al. |
| 2008/0109026 | A1 | 5/2008 | Kassam |
| 2008/0119693 | A1 | 5/2008 | Makower et al. |
| 2009/0048622 | A1 | 2/2009 | Wilson |
| 2009/0312611 | A1 | 12/2009 | Mangiardi |
| 2010/0010315 | A1 | 1/2010 | Mangiardi |
| 2011/0118710 | A1 | 5/2011 | Begemann et al. |
| 2011/0160672 | A1 | 6/2011 | Boebel et al. |
| 2011/0196205 | A1 | 8/2011 | Hathaway et al. |
| 2011/0301424 | A1 | 12/2011 | Steigerwald |
| 2012/0016204 | A1 | 1/2012 | Bastia |
| 2012/0016316 | A1 | 1/2012 | Zhuang et al. |
| 2012/0035424 | A1 | 2/2012 | Schulte |
| 2012/0071748 | A1 | 3/2012 | Mark et al. |
| 2012/0253375 | A1 | 10/2012 | Mark et al. |
| 2012/0265058 | A1 | 10/2012 | Carrascosa |
| 2012/0289816 | A1 | 11/2012 | Mark et al. |
| 2013/0066154 | A1 | 3/2013 | Mangiardi |
| 2013/0102851 | A1 | 4/2013 | Mark et al. |
| 2013/0102886 | A1 | 4/2013 | Mark et al. |
| 2013/0204095 | A1 | 8/2013 | Mark et al. |
| 2013/0204287 | A1 | 8/2013 | Mark et al. |
| 2013/0211200 | A1 | 8/2013 | Brannon |
| 2013/0245381 | A1 | 9/2013 | Dang et al. |
| 2014/0107426 | A1 | 4/2014 | Wilson |
| 2014/0171873 | A1 | 6/2014 | Mark et al. |
| 2014/0187922 | A1 | 7/2014 | Mark et al. |
| 2015/0201985 | A1 | 7/2015 | Rampersaud et al. |
| 2016/0015374 | A1 | 1/2016 | Gifford et al. |
| 2016/0015375 | A1 | 1/2016 | Kaiser et al. |
| 2016/0317182 | A1 | 11/2016 | Mark et al. |
| 2017/0000579 | A1 | 1/2017 | Mark et al. |
| 2017/0265893 | A1 | 9/2017 | Mark et al. |
| 2017/0265925 | A1 | 9/2017 | Mark et al. |
| 2017/0360291 | A1 | 12/2017 | Chegini et al. |
| 2018/0014890 | A1 | 1/2018 | Stanton et al. |
| 2018/0085182 | A1 | 3/2018 | Ewers et al. |
| 2018/0125603 | A1 | 5/2018 | Cantor et al. |
| 2018/0161024 | A1 | 6/2018 | Davis et al. |
| 2021/0085363 | A1 | 3/2021 | Mark et al. |
| 2021/0236161 | A1 | 8/2021 | Mark et al. |

FOREIGN PATENT DOCUMENTS

| | | | |
|---|---|---|---|
| DE | 102005032197 | A1 | 1/2007 |
| JP | 2289221 | A | 11/1990 |
| JP | 5344978 | A | 12/1993 |
| JP | 9224943 | | 9/1997 |
| JP | 2003153907 | | 5/2003 |
| RU | 45928 | U1 | 6/2005 |
| RU | 55570 | U1 | 8/2006 |
| SU | 131027 | A1 | 3/1959 |
| SU | 349136 | | 9/1972 |
| SU | 585840 | A1 | 12/1977 |
| SU | 1521465 | A1 | 11/1989 |
| WO | 0143627 | A1 | 6/2001 |
| WO | 2006017507 | A2 | 2/2006 |
| WO | 2006050047 | A2 | 5/2006 |
| WO | 2006050225 | A2 | 5/2006 |
| WO | 2014137530 | A1 | 9/2014 |
| WO | 2014137551 | A1 | 9/2014 |

OTHER PUBLICATIONS

Alberti et al., "Frameless Navigation and Endoscopy", J. Neurosurg., Sep. 2001;95(3), pp. 541-543.

Alexander et al., "Chapter 20: Stereotactic Frame Systems: The Compass System", Advanced Neurosurgical Navigation, 1999, pp. 267-277.

Amstutz et al., "A-Mode Ultrasound-Based Registration in Computer-Aided Surgery of the Skull", Arch. Otolaryngol Head Neck Surg., 2003, 129(12), pp. 1310-1316.

Andrews et al., "A Review of Brain Retraction and Recommendations for Minimizing Intraoperative Brain Injury", Neurosurgery, 1993, 33(6), pp. 1052-1063.

(56)           References Cited

OTHER PUBLICATIONS

Burtscher et al., "Neuroendoscopy Based on Computer Assisted Adjustment of the Endoscope Holder in the Laboratory", Minimum Invasive Neurosurgery, 2003, 46, pp. 208-214.

Del Ray Medical Center Press Release, "Advanced Neuroscience Network Brings New Innovations in Neurosurgery to South Florida", May 13, 2015, pp. 1-6.

Ding et al., "Endoport-assisted Microsurgical Resection of Cerebral Cavernous Malformations", J. Clin. Neurosci., Jun. 2015, vol. 22, No. 6, pp. 1025-1029. (Abstract only).

Eldeib et al., "Rigid Neuroendoscope Navigation System for Minimally Invasive Surgery", Engineering in Medicine and Biology, 1999, 1 page. (Abstract only).

Engh et al., "NeuroendoportSM Surgery Facilitates Removal of Hard-to-Reach Brain Tumors", Neurosurgery News, Spring 2009, vol. 10, No. 2, 8 pages.

Fukamachi et al., "Postoperative Intracerebral Hemorrhages: A Survey of Computed Tomographic Findings After 1074 Intracranial Operations", Surg. Neurol., Jun. 1985, 23(6), pp. 575-580.

Greenfield et al., "Stereotactic Minimally Invasive Tubular Retractors System for Deep Brain Lesions", Neurosurgery, 2008, 63(4), pp. 334-339. (Abstract only).

Gumprecht et al., "Neuroendoscopy Combined with Frameless Neuronavigation", British Journal of Neurosurgery, 2000, 14(2), pp. 129-131.

Hellwig et al., "Neuroendoscopic Treatment for Colloid Cysts of the Third Ventricle: The Experience of a Decade", Neurosurgery, Mar. 2003, vol. 52, Iss. 3, pp. 525-533.

Herrera et al., "Use of Transparent Plastic Tubular Retractor in Surgery for Deep Brain Lesions: A Case Series", Surgical Technology International XIX, published in 2010, pp. 1-4.

Hilton et al., "METRx Microdiscectomy Surgical Technique", Medtronic Sofamor Danek, 2001, 20 pages.

K043602 510(k) Summary, Feb. 23, 2005, 5 pages.

K060973 510(k) Summary, Jul. 26, 2006, 6 pages.

Kelly et al., "The Stereotaxic Retractor in Computer-Assisted Stereotaxic Microsurgery", J. Neurosurgery, 1988, 69, pp. 301-306.

Konen et al., "An Image-based Navigation Support System for Neuroendoscopic Surgery", in: R. Ahlers (ed.), 5. Symposium Bildverarbeitung, 1997, Technische Akademie Esslingen, 8 pages.

Kubo et al., "A Newly Designed Disposable Introducer Sheath for a Ventricular Fiberscope", Minim Invasive Neurosurg, 2004, 47(2), pp. 124-126.

Lemole et al., "Cranial Application of Frameless Stereotaxy", Barrow Neurological Institute, Barrow Quarterly, 2001, vol. 17, No. 1, 12 pages.

McInerney et al., "Frameless Stereotaxy of the Brain", The Mount Sinai Journal of Medicine, Sep. 2000, vol. 67, No. 4, pp. 300-310.

Mettler et al., "Optical Trocar Systems: Laparoscopic Entry and its Complications (A Study of Cases in Germany)", Gynaecological Endoscopy, Dec. 1999, vol. 8, Iss. 6, pp. 383-389. (Abstract only).

Nagatani et al., "High Definition Exoscope System for Microneurosurgery: Use of an Exoscope in Combination with Tubular Retraction and Frameless Neuronavigation for Microsurgical Resection of Deep Brain Lesions", No Shinkei Geka, Jul. 2015, 43(7), pp. 611-617.

NICO Corporation Press Release, "NICO Corporation Gains Market Expansion after Multiple Published Clinical Articles Support Access Technology for Deep Brain Lesions", May 5, 2015, 2 pages.

Ogura et al., "New Microsurgical Technique for Intraparenchymal Lesions of the Brain: Transcyclinder Approach", Aeta Neurochirurgica (Wein) 2006, 148, pp. 779-785.

O'Shaughnessy, P., "New Brain Tumor Technology Helps Man Who Took Two Bullets to the Head Return to Normal Life", Daily News, Jun. 19, 2011, 2 pages.

Otsuki et al., "Stereotactic Guiding Tube for Open-System Endoscopy: A New Approach for the Stereotactic Endoscopic Resection of Intra-Axial Brain Tumors", Neurosurgery, 1990, 27(2), pp. 326-330.

Prevedello et al., "Vycor ViewSite TC®: Endoscope Guided Intraparenchimal Brain Tumor Ressection", Ohio State University Medical Center Minimally Invasive Neurosurgery, 2 pages.

Rampini et al., "Stereotactically Guided Endoscopy for the Treatment of Arachnoid Cysts", Pediatric Neurosurgery, 1998, 29(2), pp. 102-104. (Abstract only).

Raza et al., "Minimally Evasive Trans-Portal Resection of Deep Intracranial Lesions", Neurosurgery, vol. 54, Feb. 2011, pp. 1-7.

Recinos et al., Use of Minimally Invasive Tubular Retraction System for Deep-seated Tumors in Pediatric Patients, J. Neurosurg. Pediatrics 7, 2011, pp. 516-521.

Ross et al., "A Simple Stereotactic Retractor for the use with the Leskell Stereotactic System", Neurosurgery, 1993, 32 (3), pp. 475-476, discussion p. 476.

Rymarczuk et al., "Use of Minimally Invasive Retractor System for Retrieval of Intracranial Fragments in Wartime Trauma", World Neurosurgery, 2015, pp. 1-26.

Scholz et al., "Development of an Endoscopic Navigation System Based on Digital Image Processing", Computer Aided Surgery, 1998, 3(3), pp. 134-143. (Abstract only).

Scholz et al., "Virtual Image Navigation: A New Method to Control Intraoperative Bleeding in Neuroendoscopic Surgery", Neurosurg. Focus, 2000, 8(6), pp. 1-8.

Shoakazemi et al., "A 3D Endoscopic Transtubular Transcallosal Approach to the Third Ventricle", J. Neurosurg., 2015, pp. 1-10.

Shults et al., Neuro-opthalmic Complications of Intracranial Catheters, Neurosurgery, vol. 33, No. 1, Jul. 1993, pp. 135-138.

Slavin, K. "Testimonials", no date, but admitted as prior art between Jun. 17, 2005 and Mar. 27, 2012, 4 pages.

Spetzger et al., "Navigational Microneurosurgery: Experience with EasyGuide Neuro", Medicamundi, 1997, 41(1), pp. 28-35.

Tao et al., "Microsurgical Resection for Lateral Ventricular Meningiomas with Neuronavigation and Tubular Retractor System", Chin. J. Neurosurgery, vol. 31, No. 4, 2015, pp. 332-336. (Abstract only).

UPMC: Minimally Invasive Brain Surgery, Legacy of Innovations, Breakthroughs in Minimally Invasive Brain Surgery at UPMC, 2014, 1 page.

Vycor Medical, "Vycor ViewSite TC: Endoscopic Intraparenchimal Brain Tumor Resection with Image Guidance," 2 pages, no date but admitted as prior art between Jun. 17, 2005 and Mar. 27, 2012, 2 pages.

Wang et al., "Endoscopic Hematoma Evacuation in Patients with Spontaneous Supratentorial Intracerebral Hemorrhage", Journal of the Chinese Medical Association, 78, 2015, pp. 101-107.

Zhong et al., "Brain Retraction Injury", Neurological Research, Dec. 2003, vol. 25, pp. 831-838.

Canadian Examination Report for Canadian Application No. 3,191,957, dated Jul. 23, 2024, 4 pages.

Canadian Examination Report for Canadian Application No. 3,191,957, dated Dec. 4, 2025, 5 pages.

SURGICAL INTRODUCER WITH GUIDANCE SYSTEM RECEPTACLE

This application is a continuation of U.S. Utility application Ser. No. 17/473,282, filed Sep. 13, 2021, which is a continuation-in-part of U.S. Utility application Ser. No. 16/740,858, filed Jan. 13, 2020 (now U.S. Pat. No. 11,517, 347), which is a continuation of U.S. application Ser. No. 15/805,821, filed on Nov. 7, 2017 (now U.S. Pat. No. 10,543,016), which is a continuation-in-part that claims priority to U.S. Provisional Application No. 62/418,507, entitled SURGICAL INTRODUCER WITH GUIDANCE SYSTEM RECEPTACLE, filed Nov. 7, 2016, and U.S. Utility application Ser. No. 15/372,890, filed Dec. 8, 2016 (now U.S. Pat. No. 10,376,258), the complete contents of all of which are incorporated herein by reference.

FIELD OF THE INVENTION

The present invention relates to delicate tissue surgical retractor systems for use in the brain or other tissue susceptible to retraction injury.

BACKGROUND

A variety of different devices have been used to retract delicate tissue during surgical procedures. One such device is illustrated in United States Patent Publication Number 2010/0010315, which is incorporated herein by reference. FIG. 1 of this publication illustrates a soft tissue retractor system having a hollow retractor 100, and an introducer 102 that is selectively inserted into the retractor 100. The retractor 100 and/or introducer 102 may include a handle 104 to facilitate manipulation and placement of the retractor system, and a lock to hold the introducer and retractor together. The handle 104 is configured to connect to a clamp 106, such as the standard surgical clamp 106 shown in FIG. 1. The device in FIG. 1 (with some modifications) is commercially sold as the "VBAS" device by Vycor Medical, Inc. of Boca Raton, Florida.

A retractor system such as shown in FIG. 1 is often used by inserting the introducer 102 into the retractor 100 and locking it in place, so the two can be moved and manipulated as a unit. The combined retractor system is inserted into the patient's body and moved to the surgery site, and then the introducer 102 is unlocked and removed to permit access to the site through the retractor 100. When the unit is in place (either before or after the introducer 102 is removed), the handle 104 may be locked to a clamp 106 to hold the retractor 100 in place. Surgeons using this retractor sometimes do not use a clamp to hold the retractor at the surgery site, and often manually manipulate the retractor to access different parts of the surgery site during the surgical procedure. The retractor system and the retractor may be manipulated by holding the proximal ends of the introducer or retractor or by holding the handle.

The device shown in FIG. 1 may have a transparent introducer 102 and/or retractor 100, and surgeons using such devices advantageously use the transparent introducer and retractor to observe the underlying tissue and to visually guide the unit to the surgery site. While it has been found that visual guidance by looking through the introducer 102 is very beneficial, it also has been found that some form of additional guidance or navigation may be desired in some cases. For example, in some cases, surgeons have used a probe or guide wire (a narrow elongated rod) to guide the movement of the retractor system. In such cases, the probe is advanced to the surgery site, and then the interlocked retractor system is slid over the probe until it reaches the surgery site. This is facilitated by the inclusion of a hole at the tip of the introducer that fits around the probe. If the hole through the tip of the introducer is absent, this method cannot be used. This type of system is described in United States Patent Publication Numbers 2008/0109026 and 2009/0048622, which are incorporated herein by reference. These references also show an alternative construction, in which the retractor is not locked to the introducer.

It has been found that some surgeons using the above procedure may use a probe that is integrated into a computer navigation system. For example, the probe may include a so-called "starburst" or the like, on the probe's proximal end (i.e., the end opposite the distal end that is inserted to the surgical site). This and other navigation systems are known in the art. For example, frameless navigation systems and other computerized guidance systems and methods are described in U.S. Publication No. 2001/0027271 (which is incorporated herein by reference in its entirety) and others, and are commercially available from companies such as Medtronic, Inc., Stryker, BrainLab, AG, and GE Healthcare. As used herein, "computerized guidance" encompasses any method of guiding a device to or at a surgical site that relies on computer visualization and/or control.

United States Patent Publication Number 2010/0010315 briefly notes the possibility of using stereotactic guidance or navigation in conjunction with a surgical retractor, but does not illustrate or describe this procedure or any apparatus for accomplishing this objective. Nevertheless, surgeons have been known to use a navigation probe "freehand" with a VBAS device such as shown in FIG. 1. In such cases, the surgeon holds the navigation probe in place within the introducer while advancing the unit towards the surgery site. The tip of the probe may be placed in or near an opening through the tip of the introducer, but the opening through the introducer may be somewhat larger than the probe tip and is oval, and does not hold the probe tip in any particular orientation. Such techniques can suffer from inaccuracy and displacement of the probe from the introducer tip, and it can be difficult to hold the probe in place. Also, in some cases the probe tip may extend partially through the introducer tip opening, which can risk damaging underlying tissue. However, freehand use can be helpful to allow occasional removal of the probe to provide an unobstructed view through the introducer of the underlying tissue.

While computerized surgical guidance systems are well-known, a number of limitations exist with respect to their use with retractor systems, and particularly with systems like those shown in FIG. 1. For example, while some surgeons use computerized guidance to direct a probe to the surgery site, and then slide the retractor system over the probe to the site, the movement of the retractor may be somewhat imprecise and the process can be unduly cumbersome. This method also is not available if the retractor system does not have a through-hole that fits over the probe (due either to the absence of a hole or a hole that is too small). In addition, the probe does not provide a view of the tissue through which it is advanced, so there is no visual means to perceive and avoid critical tissue (e.g., major blood vessels or nerves) when inserting a probe before inserting a retractor/introducer system. Also, the small-diameter probe may sever delicate tissue cells, such as grey or white brain matter, rather than moving the cells aside and passing between them as would be expected to happen when advancing the retractor system.

United States Patent Publication Number 2013/0066154, which is incorporated herein by reference, shows examples of systems for integrating a navigation probe into a surgical introducer. For example, FIGS. 1-6 of this publication show a navigation probe that is secured to the inside of a pre-existing introducer by resilient means, such as rubber plugs or O-rings. Another embodiment uses a slip fit (e.g., FIGS. 7-8), and still another embodiment uses an arm to hold the probe down inside the introducer (FIG. 9). Still other versions mount the navigation device outside the introducer, to an arm that is connected to the retractor assembly (FIGS. 10-11). While these systems may provide suitable performance, they also have certain potential shortcomings. For example, resilient plugs may slip in the presence of fluids and may be difficult to disengage to remove the navigation device during surgery, a slip fit requires careful monitoring to ensure proper positioning, an arm as shown in FIG. 9 to hold the probe in place requires the probe to be modified to include a surface against which the arm pushes, and locating the navigation device outside the introducer complicates the correlation between the navigation device and the tip of the introducer or retractor.

United States Patent Publication Number 2012/0071748, which is incorporated herein by reference, shows another example of a system for integrating a navigation probe into a surgical introducer. In this case, the probe is retained in a narrow channel through the introducer, and held in place with a threaded locking screw. The locking screw adds an additional potentially-removable part to the operating theater, and therefore this reference adds a separate retaining device (see FIG. 7B) to prevent the locking screw from being removed. The locking screw also can be relatively difficult to manipulate, particularly when wearing surgical gloves.

United States Patent Publication Number 2016/0015374, which is incorporated herein by reference, shows yet another example of a system for integrating a navigation probe into a surgical introducer. The device shown in this publication holds the probe in a tube-like registration indicator that extends distally into the introducer from the proximal open end of the introducer, and has a convenient single-throw clamp to lock the probe in place. This registration indicator beneficially indicates when the navigation probe is fully seated in the introducer, however, it might it may obstruct the surgeon's view to some degree, and may make frequent removal and reinstallation of the navigation probe somewhat cumbersome as compared to freehand use of the probe. Movement of the navigation probe (with or without the registration indicator) is limited by a stop surface, which may be flat, or tapered to guide the probe tip to the desired location. The stop surface also may comprise a circular ring or arrangement of ribs that surround the probe tip and hold it along the tapered surface of the probe tip. While such shapes are contemplated, they are not illustrated.

It has been found that there still remains a need to provide alternative apparatus and methods for coordinating the use of guidance systems with surgical introducers.

SUMMARY OF THE INVENTION

In one exemplary aspect, there is provided a surgical introducer system for use with a navigation probe having a navigation element, a probe shaft, and a distal probe tip that tapers from a first probe diameter at the probe shaft to a second probe diameter at a terminal end of the distal probe tip, the second diameter being less than the first diameter. The introducer system comprises an introducer having: an outer introducer sidewall extending along a longitudinal axis from a proximal introducer end to a distal introducer end; an inner introducer sidewall extending within the outer introducer sidewall along the longitudinal axis and forming an introducer passage extending in a distal direction from a proximal passage opening at the proximal introducer end to an introducer passage end wall located proximal to the distal introducer end; and an end wall passage extending from the introducer passage end wall towards the distal introducer end. The introducer end wall passage joins the introducer end wall at one or more end wall edges defining an axial stop ring configured to contact the distal probe tip between the probe shaft and the terminal end of the distal probe tip at a line of contact to thereby prevent movement of the navigation probe in the distal direction.

The foregoing summary of the invention provides a variety of exemplary embodiments that may be used in any suitable combination, and is not intended to impose any limitations upon the invention recited in the claims.

BRIEF DESCRIPTION OF THE DRAWINGS

A better understanding of the exemplary embodiments may be understood by reference to the attached drawings, in which like reference numbers designate like parts. The drawings are exemplary, and not intended to limit the claims in any way.

FIGS. 10C and 10D show the distal introducer end of the embodiment of

FIG. 10A in cutaway side view at various levels of magnification.

Figure 18:
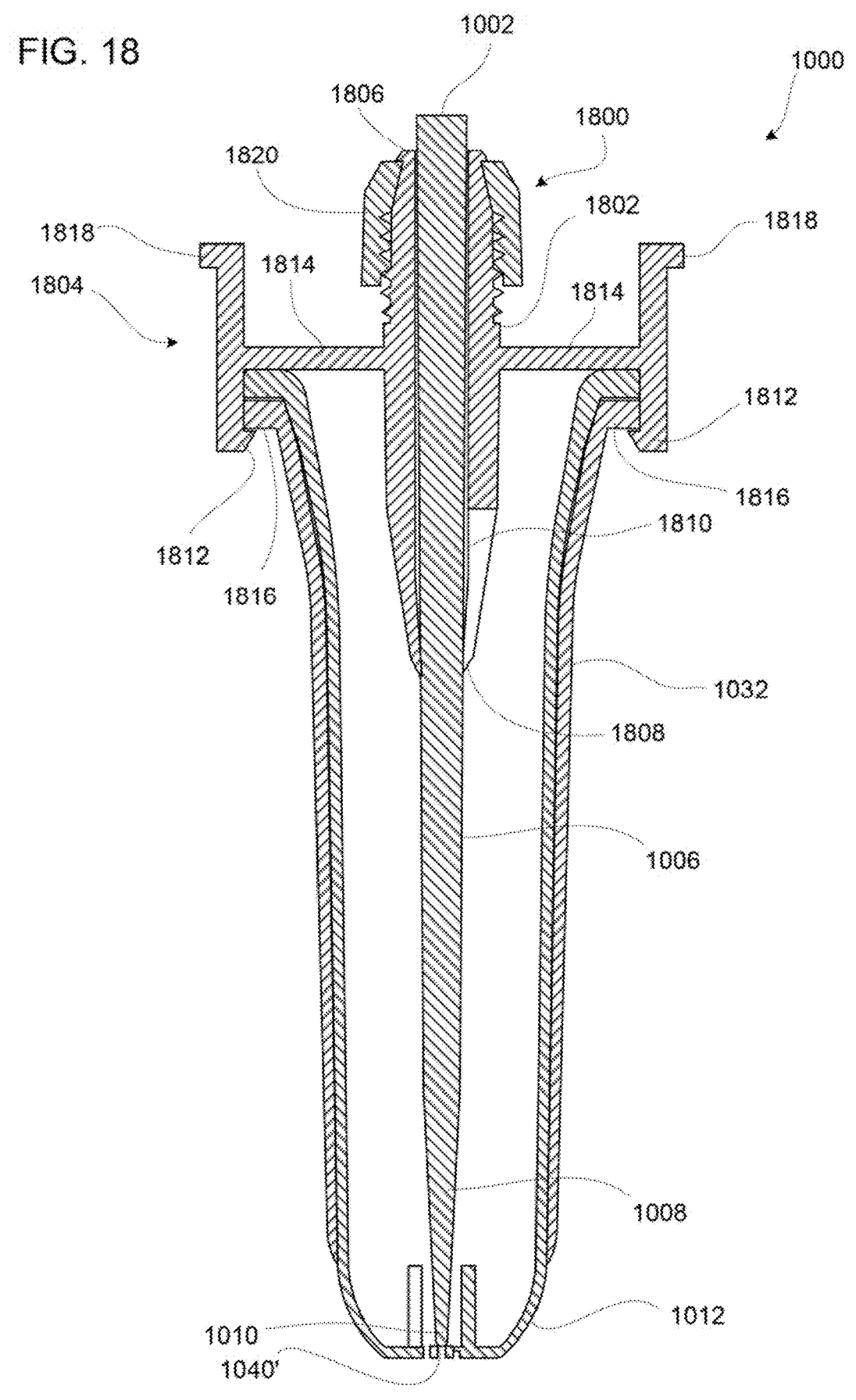

FIG. 18 is a cutaway side view of another exemplary embodiment of an introducer system, including a probe retainer.

FIG. 20 is a cutaway side view of another exemplary embodiment of an introducer system.

FIG. 21 is a partial cutaway side view of another exemplary embodiment of an introducer system, including a probe retainer.

DETAILED DESCRIPTION OF EMBODIMENTS

Embodiments of the invention may provide various features to supplement or advance the state of the art of surgical introducers and retractor systems. As used herein, the term "guidance system" is intended to include any system for assisting a surgeon with advancing the retractor system to the surgery site, and can include passive systems like guide wires, or active systems like navigation probes that are detected and tracked using a computerized telemetry system. The term "surgeon" includes anyone in the operation theater who might use or manipulate the introducer system. Active probes can be tracked by various techniques, including: optically tracking a "starburst" or other marker mounted on a portion of the probe that remains visible during the procedure; directly monitoring the probe's position using radiation imaging (e.g., X-ray) or magnetic imaging; physically connecting the probe to a frame of reference system to mechanically track the position of the probe; or other means or combinations of means, as known in the art. The terms "navigation" and "guidance" are used interchangeably herein. Embodiments also may be used with manual systems in which the surgeon moves the retractor system entirely by hand, or semi-automated or automated systems that operate under the surgeon's control or automatically advance the retractor system to the surgery site without the surgeon's intervention.

Figure 1:
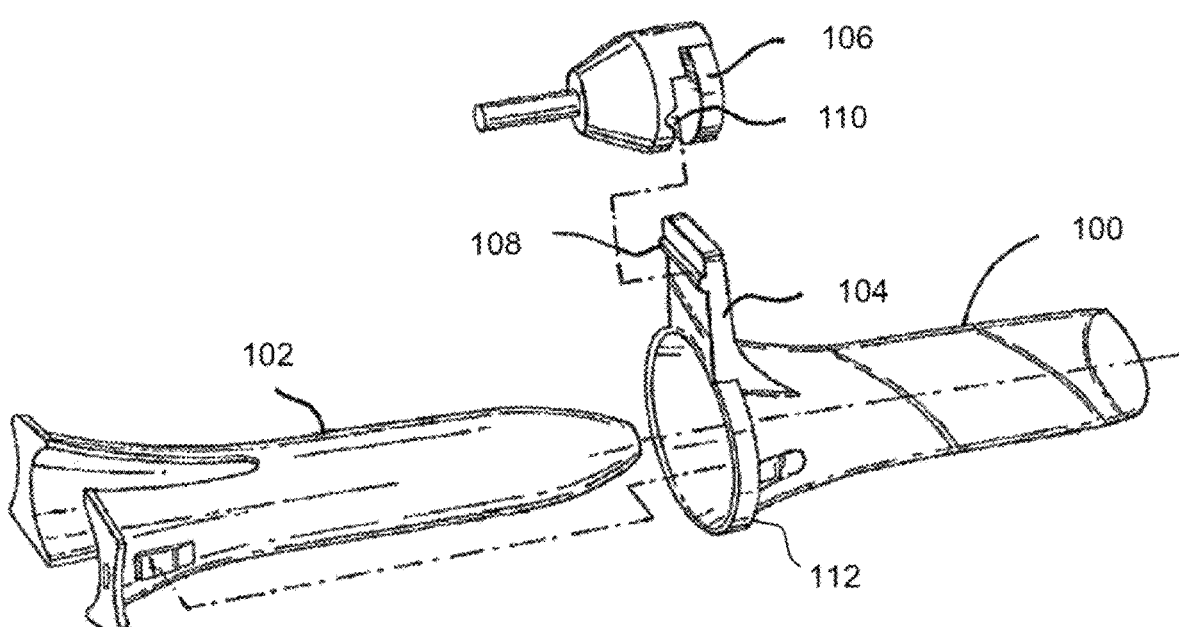
FIG. 1 is an example of a prior art delicate tissue retractor system.

Embodiments may be used with dedicated systems that are designed anew, or with preexisting systems. For example, embodiments may be used with systems like the one shown in FIG. 1, such as by supplementing, modifying or replacing the introducer 102, or with other introducer assemblies, as will be appreciated by persons or ordinary skill in the art. The embodiments described herein may be used with a retractor 100 as shown in FIG. 1, or in other retractors. It will be readily appreciated that the shape of the introducer can be modified to fit into any conventional retractor, and the introducer also may be modified to connect to the retractor (if necessary or desired) using any suitable clamp or other engagement mechanism. For example, embodiments may be used with small-scale versions of introducers like the one shown in FIG. 1, in which the embodiment optionally may be scaled down to allow visibility into the retractor, but providing such visibility is not required in all embodiments.

The exemplary embodiments described herein are directed towards introducers for use in neurosurgery or other operations in and around the brain or skull. However, uses in other parts of the body are also possible.

Figure 2A:
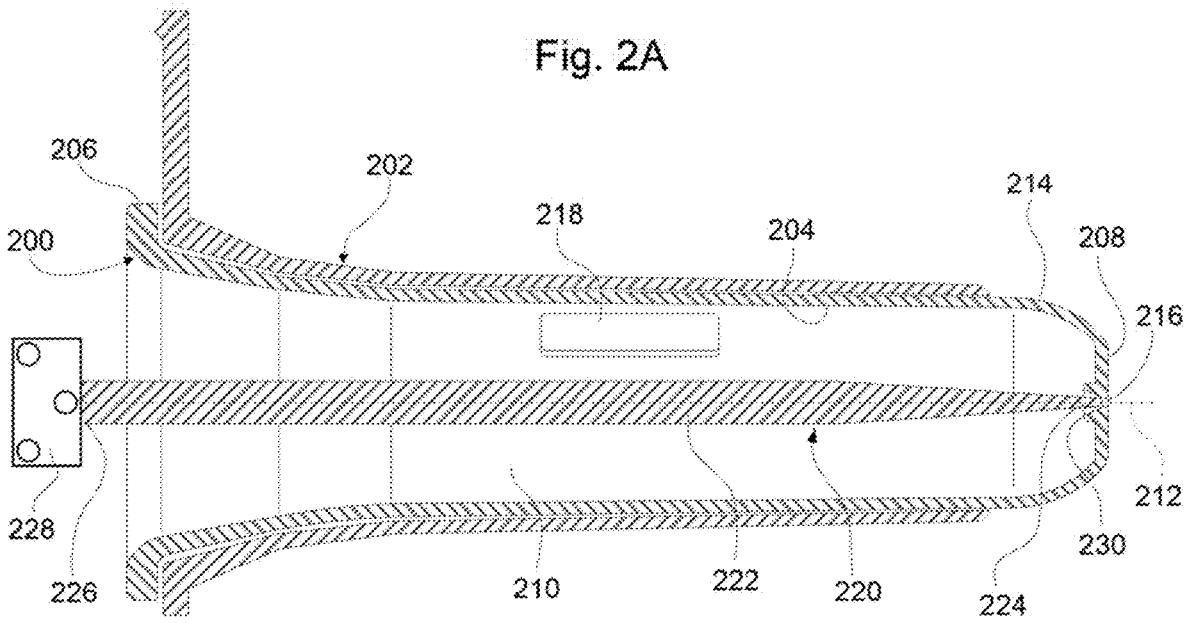
FIG. 2A is a cutaway side view of a first embodiment of an introducer having a guidance probe receptacle.

FIG. 2A shows an exemplary embodiment of an introducer 200 that is configured to be releasably retained inside a retractor 202 such as retractor 100 of FIG. 1. The introducer 200 comprises a sidewall 204 that extends from a proximal introducer end 206 to a distal introducer end 208. As used herein, "proximal" refers to the end that generally faces the surgeon in use, and "distal" refers to the end that is located towards or inserted into the patient. When connected together, the proximal introducer end 206 may be located at or near a proximal retractor end, and the distal introducer end 208 extends beyond a distal retractor end. The retractor 202 preferably comprises a hollow tubular retractor passage extending along a longitudinal axis from a proximal retractor end to a distal retractor end, and is dimensioned to allow surgical procedures to be undertaken therethrough.

The introducer sidewall 204 forms an introducer passage 210 that extends along a longitudinal axis 212 extending from the proximal introducer end 206 to the distal introducer end 208. When assembled with the retractor 202, a distal tip portion 214 of the introducer 200 extends beyond the distal end of the retractor 202. Together, the distal tip portion 214 and the retractor 202 form a generally smooth and continuous surface for gently displacing brain tissue or the like as the assembly is advanced into the body. The distal tip portion 214 preferably is tapered with a rounded (such as shown) or conical shape. A tip opening 216 may be provided at or near the distal introducer end 208, as discussed in more detail below. A lock (see, e.g., FIG. 1) may be provided to selectively hold the introducer 200 to the retractor 202.

The sidewall 204 preferably comprises a continuous wall surface such that the passage 210 has a closed outer perimeter, such as shown in FIG. 1. This can help prevent unwanted entry of body fluids and provide a smooth continuous surface for viewing through the sidewall 204 (if it is transparent) and for guiding instruments down the length of the passage 210 without risk of displacement. However, one or more openings 218 may be provided in the sidewall 204 in alternative embodiments.

The introducer sidewall 204 may have any suitable cross-sectional profile (i.e., profile in a plane orthogonal to the longitudinal axis 212). For example, the sidewall 204 may be circular, elliptical, oval or otherwise generally curved (i.e., comprised entirely of curved surfaces and/or very short straight surfaces that effectively simulate a smoothly-curved shape). If desired, the cross-section may include one or more rectilinear segments (e.g., a D-shape), or may be entirely rectilinear (e.g., a square or triangular shape). The sidewall profile also may taper to be larger at the proximal end than at the distal end, and preferably reduces at least slightly in size as it approaches the distal introducer end 208. The outer surface of the sidewall 204 may be shaped to match the shape of a corresponding inner wall of the retractor 202, but this is not strictly required. The introducer sidewall 204 also preferably has a generally consistent wall thickness along its length, which can facilitate manufacturing and provide a more suitable optical path for viewing through the sidewall 204. It will be understood that cross-sectional shape of the passage 210 will be defined by the shape of the sidewall 204, and therefore the foregoing discussion about the shapes of the sidewall 204 applies also the shape of the passage 210.

The introducer 200 preferably is transparent at least at the distal end 206, and more preferably at the distal tip portion 214, and more preferably along most or the full length of the sidewall 202. The transparent portion allows the surgeon to visualize underlying tissue while advancing the introducer 200 through brain tissue or the like, which can provide significant benefits during surgery. However, in alternative embodiments, the introducer 200 may be opaque. Suitable materials for the introducer 200 include polycarbonate and other kinds of plastic, metals such as aluminum, stainless steel or titanium, glass or ceramic, or other materials that are biocompatible or that can be treated via coatings or the like to be biocompatible.

The passage 210 is sized to accommodate a navigation probe 220. The probe 220 comprises a shaft 222 that extends from a distal probe tip 224 to a proximal probe end 226. The probe 220 includes a navigation element 228 that is operatively associated with a navigation system to track the position of the probe 220 and convey this information to the surgeon during the course of surgery.

The navigation element 228 may comprise, for example, an optical array (e.g. three or more lights or reflectors in a predetermined physical pattern) that provides a three-dimensional registration of the position of the probe tip 224 when viewed by a corresponding navigation camera system. Such an array may be mounted to the proximal probe end 226 or elsewhere where it can be viewed by the navigation cameras. The need for a line-of-sight between the optical array and the cameras is likely to require the navigation element 228 to be positioned outside the introducer 200. Alternatively, the navigation element 228 may comprise a magnetic element that can be tracked by a corresponding magnetic tracking system. In this case, it may not be necessary to position the navigation element 228 outside the introducer 200. Other alternatives of navigation elements 228 will be apparent to persons of ordinary skill in the art in view of the present disclosure. Examples of navigation probes 220 and corresponding tracking systems are provided by Stryker Navigation of Kalamazoo, Michigan, U.S.A.; Brainlab AG of Feldkirchen, Germany; Synaptive Medical of Toronto, Ontario; and Medtronic of Minneapolis, Minnesota, U.S.A.

The introducer passage 210 is significantly larger in the lateral direction (i.e., perpendicular to the longitudinal axis 212) than the probe shaft 222. This may allow the surgeon to visualize down the length of the passage 210 without her vision being unduly obstructed by the probe 220. This also may allow the surgeon to insert other instruments such as an endoscope or aspiration tube into the passage 210 while the probe 220 remains in place, and so on. As a consequence of their disparate relative sizes, the sidewall 204 does not hold the navigation probe shaft 222 against lateral movement within the passage 210. It expected that some lateral movement of the probe shaft 222 within the passage 210 will not critically affect proper navigation, but it is believed to be more important to assure continuous proper registration between the distal probe tip 224 and a fixed location at the distal introducer end 208. For example, maintaining the probe tip 224 with little or no deviation from the geometric center of the introducer profile at the distal introducer end 208 is expected to provide sufficient registration for accurate navigation, even if the proximal end of the shaft 222 might move laterally within the passage 210.

Figure 2B:
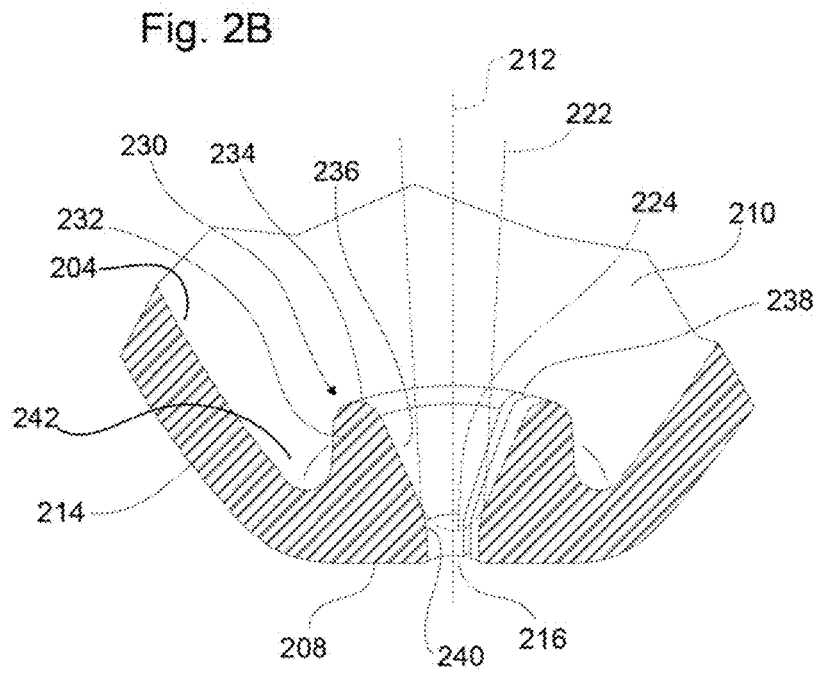
FIG. 2B is a cutaway side view of the distal tip of the embodiment of FIG. 2A, shown at a slight oblique angle.

In the embodiment of FIGS. 2A and 2B, the probe tip 224 is maintained in registration with the distal introducer end 208 by a probe receptacle 230. The probe receptacle 230 preferably is located at the geometric center of the introducer profile at the distal introducer end 208 (e.g., the geometric center of the ellipse if the distal introducer end 208 is elliptical), but this is not strictly required in all embodiments. For example, the receptacle 230 may be offset from the introducer's central axis.

The probe receptacle 230, in this embodiment, comprises a generally circular receptacle wall 232 having an inner surface 236 that extends within the passage 210 from a distal receptacle end 240 to a proximal receptacle end 234. The inner surface 236 tapers from a relatively large diameter at the proximal receptacle end 234 to a relatively small diameter at a distal receptacle end 240. The distal receptacle end may be located at or near the distal introducer tip 208. The receptacle wall 232 is sized to restrict the distal probe tip 224 from moving laterally beyond a predefined range of movement. For example, the receptacle wall 232 may restrict movement of the probe tip 224 to a range of less than 1 millimeter ("mm") in the lateral direction, or more preferably it may be sized to restrict any movement in the lateral direction.

The diameter of the proximal receptacle end 234 may have any size, but preferably is not so large as to significantly obstruct vision through the introducer 200, and not so small that it is overly difficult to position the probe tip 224 within the receptacle 230 during surgery. The receptacle wall's tapered surface 236 helps guide the probe tip 224 to the proper location within the receptacle 230, and the surface 236 may have a conical or curved profile as viewed from the lateral direction. The surface 236 also may have a region with a shape specifically selected to match the shape of the probe tip 224. For example, if the probe tip 224 is hemispherical, all or a portion of the surface 236 may have a matching shape. As another example, if the probe tip 224 is cylindrical (or has a hemispherical tip with a cylindrical body immediately adjacent the tip), a distal portion of the surface 236 may have a matching cylindrical shape. Other alternatives will be apparent to persons of ordinary skill in the art in view of the present disclosure.

The receptacle wall 232 also may be shaped and sized to hold the probe tip 224 in close proximity to the distal introducer end 208. For example the distance from the distal introducer end 208 to the probe tip, as measured along the longitudinal axis 212, preferably is less than 5.0 mm, and more preferably less than 1.0 mm, and most preferably 0.5 mm or less. Where the probe tip 224 is at 1.0 mm or less from the distal introducer end 208 it may not be necessary to attempt to correct for this amount of displacement for purposes of navigating into the brain tissue, as this is expected to be within the normal amount of deviation of brain tissue movement within the skull. It is preferred, but not strictly required, that the probe tip 224 does not protrude beyond the distal introducer end 208.

The introducer tip opening 216 (if one is provided) may be located within the probe receptacle 230 at the end of the receptacle wall 232, such as shown in FIG. 2B. Alternatively, the introducer tip opening 216 may be located elsewhere in the distal introducer end 208 at a location outside the receptacle 230. The probe receptacle 230 also may include one or more openings forming flow passages 238 to allow fluid to bypass the receptacle wall 232; this feature can help ensure proper drainage of fluids that might otherwise accumulate at the distal end of the passage 210 at locations between the proximal receptacle end 234 and the sidewall 204. More specifically, a gap 242 may be provided between an outer wall 244 of the probe receptacle 230 and the introducer sidewall 204, and fluid may accumulate in this gap 242 under some circumstances. The flow passages 238 are provided to allow fluid to exit the gap 242.

In use, the surgeon assembles the introducer 200 and retractor 202 together, places the probe tip 224 into the receptacle 230, and uses computer-aided navigation provided by the probe 220 to guide the assembly to the surgery site. During navigation, the probe 220 indicates the position of the distal introducer end 208 relative to the underlying tissue via a computer screen overlay of a representation of the probe and a representation of the tissue. Throughout the process, the surgeon preferably can inspect the tissue through transparent walls of the introducer 200 and retractor 202, and can periodically remove the probe 220 as necessary to obtain a better visual image or to perform intermediate procedures such as suctioning fluid and the like.

Figure 3A:
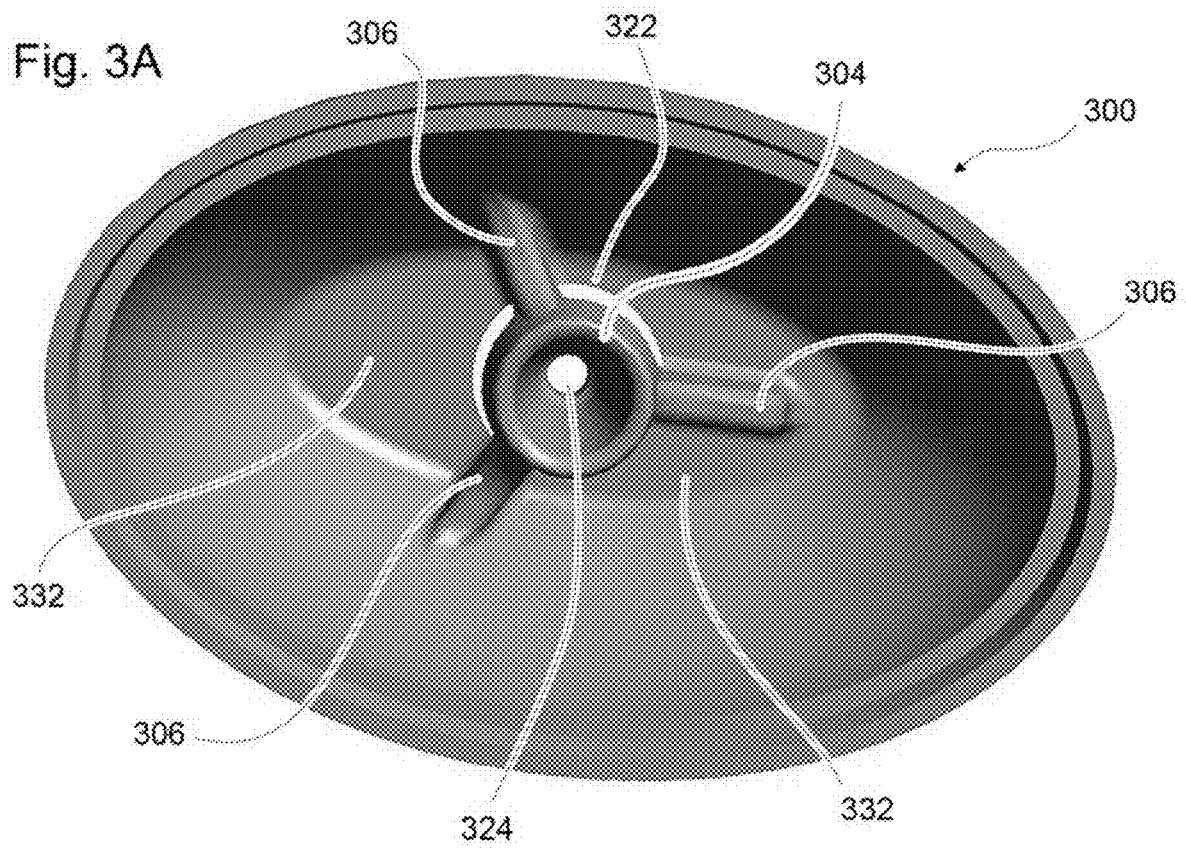
FIG. 3A illustrates a distal tip of another embodiment of an introducer having a guidance probe receptacle, as viewed from inside the introducer.
Figure 3B:
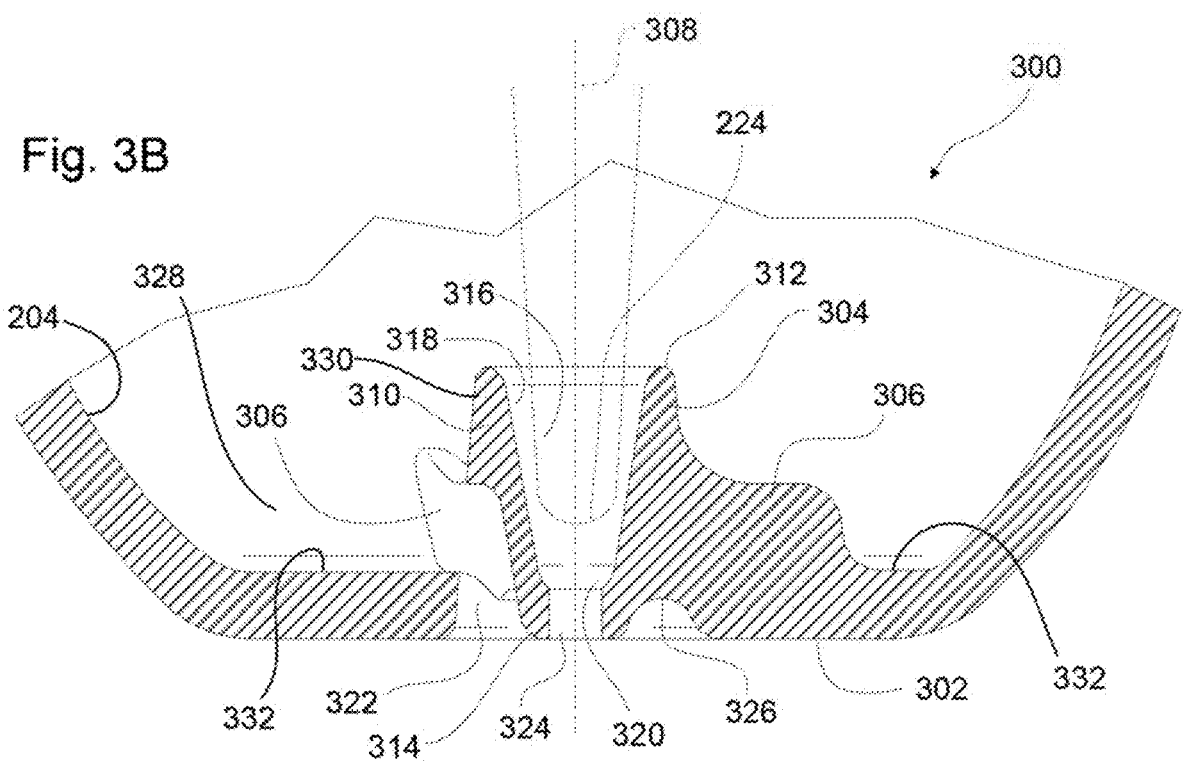
FIG. 3B is a cutaway side view of the distal tip of the embodiment of FIG. 3A.

FIGS. 3A and 3B illustrate another embodiment of an introducer 300. For simplicity, only the portion of the introducer 300 located near the distal introducer end 302 is shown in these illustrations, and it will be understood that other features of the introducer 300 such as the remainder of the internal passage and other features described previously herein will be connected to the illustrated portion. In this embodiment, introducer 300 has a probe receptacle 304 that is suspended within the introducer 300 by a number of supports 306.

The probe receptacle 304 may be located on the introducer's centerline, which is parallel to the introducer's longitudinal axis 308, but other locations are possible. The probe receptacle 304 preferably comprises a receptacle wall 310 (which is circular, but can have other shapes) that extends from a proximal receptacle end 312 to a distal receptacle end 314. The receptacle wall 310 has an inner surface 316 that tapers from a relatively large size at the proximal receptacle end 312 to a relatively small size at the distal receptacle end 314. The inner surface 316 is sized and shaped to retain the distal probe tip 224 to prevent the probe tip 224 from moving laterally. For example, FIG. 3B shows the probe tip 224 at a position shortly before it fully seats in the probe receptacle 304, to more clearly show that the tapered inner surface 316 transitions from a linearly tapering proximal surface portion 318 to a distal surface portion 320 that is shaped to match the hemispherical shape of the probe tip 224. When fully seated, the probe tip 224 abuts the distal surface portion 320 in something like a ball-and-socket arrangement, with the semi-hemispherical surface of the distal surface portion 320 cupping and closely conforming to the hemispherical probe tip 224. In other embodiments, the inner surface 316 may have other shapes to accommodate different shapes and sizes of probe tip 224. For example, a simple conical shape can accommodate different probes having various tip diameters.

The supports 306 are formed as planar ribs that radiate outward from the introducer's centerline, and extend in parallel with the longitudinal axis 308. In alternative embodiments, the supports 306 may be replaced by other shapes, such as blocks, pillars, and so on.

The probe receptacle 304 may be positioned adjacent to an introducer tip opening 322 that passes through the distal introducer end 302. The introducer tip opening 322 and probe receptacle 304 are positioned such that fluid located in a gap 328 between the probe receptacle's outer wall 330 and the sidewall 204 can pass through the introducer tip opening 322 without passing through the probe receptacle 304. Thus, fluid can flow through the introducer tip opening 322 even when the probe tip 224 is installed within the probe receptacle 304. The probe receptacle 304 also may include a distal receptacle opening 324 passing thorough the distal receptacle end 314, which provides an additional flow path when the probe is not installed in the probe receptacle 304 and prevents fluid from pooling in the probe receptacle 304.

In the illustrated embodiment, the distal receptacle end 314 extends into the introducer tip opening 322, such that it lies at or near the plane of the distal introducer end 302. Thus, the introducer tip opening 322 is formed as an annular passage that surrounds the probe receptacle 304, and the supports 306 bridge the gap between the distal introducer end 302 and the probe receptacle 304. The supports 306 may include arched voids 326 to help reduce any disruption in the flow through the introducer tip opening 322 that the supports 306 might otherwise cause.

The placement of the distal receptacle end 314 within the introducer tip opening 322 can place the probe tip 224 as close as possible to the distal introducer end 302. This simplifies the registration between the probe 220 and the introducer 300 because there is very little offset between their distal ends. However, this arrangement is not required in all embodiments. For example, the probe receptacle 304 may be moved further in the proximal direction (i.e., back into the introducer passage) to allow more fluid flow capacity through the introducer tip opening 322, to make the introducer tip opening 322 smaller, and for other reasons. If the offset between the probe tip 224 and the distal introducer end 302 is significant, the computer system associated with the probe 220 can be programmed to account for this offset when indicating the position of the introducer 300 to the surgeon, as known in the art.

The receptacle 304 is preferably positioned and sized such that at least a portion of the introducer sidewall 204 at the distal introducer end 302 is visible to the surgeon while the probe tip 224 is installed in the receptacle 304. For example, a pair of transparent faces 332 of the sidewall 204 (which may be flat as shown or curved) may be visible around the receptacle 304 and probe 220. The surgeon can visually inspect the underlying tissue even while the probe 220 is in place, and can move the probe shaft 222 around within the passage 210 to alter her view without displacing the probe tip 224 from the receptacle 304.

Figure 4A:
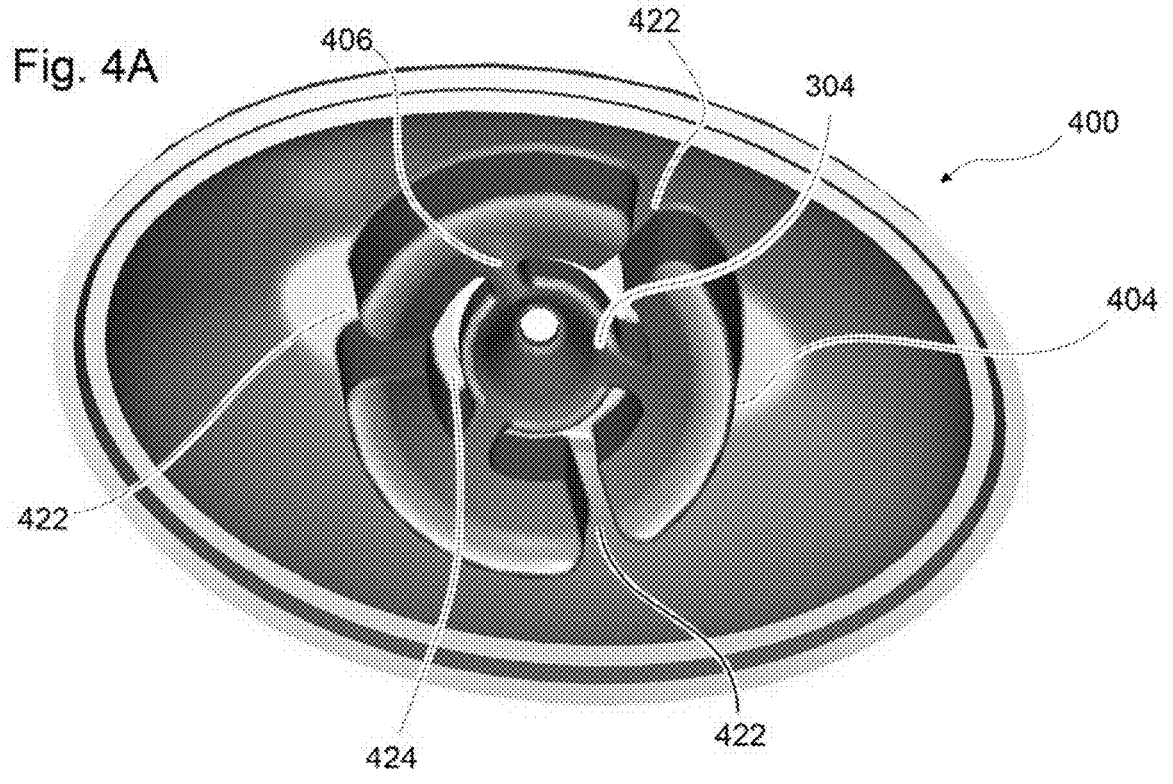
FIG. 4A illustrates a distal tip of another embodiment of an introducer having a guidance probe receptacle, as viewed from inside the introducer.
Figure 4B:
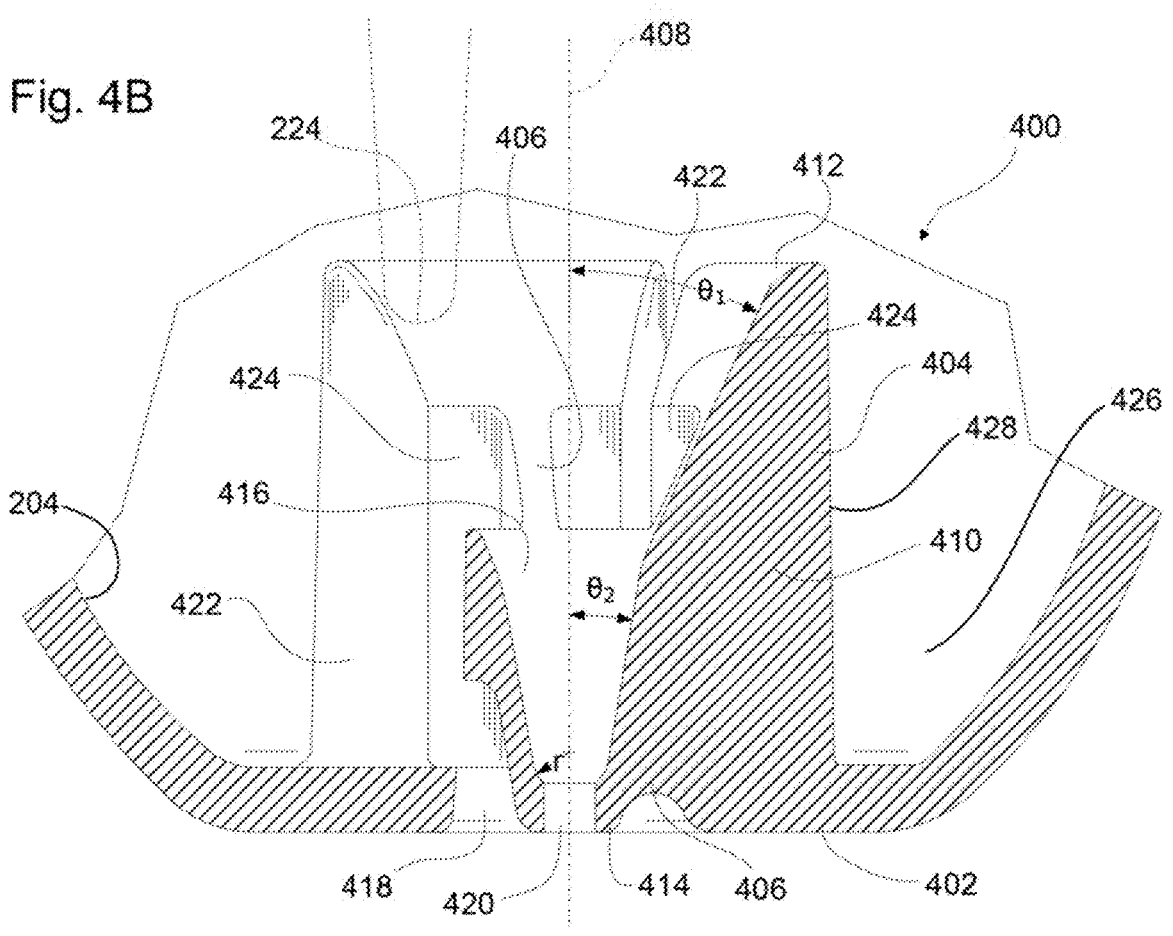
FIG. 4B is a cutaway side view of the distal tip of the embodiment of FIG. 4A.

FIGS. 4A and 4B illustrate another embodiment of an introducer 400. As with FIGS. 3A and 3B, only the region of the introducer 400 adjacent the distal introducer end 402 is shown. It will be understood that other features of the introducer 400 such as the remainder of the internal passage and other features described previously herein will be connected to the illustrated portion. In this embodiment, the introducer 400 has a probe receptacle 404 that includes a portion that is suspended within the introducer 400 by a number of supports 406. The probe receptacle 404 may be located on the introducer's centerline, which is parallel to the introducer's longitudinal axis 408, but other locations are possible.

The probe receptacle 404 preferably comprises a receptacle wall 410 (which is circular, but can have other shapes) that extends from a proximal receptacle end 412 to a distal receptacle end 414. The receptacle wall 410 has an inner surface 416 that tapers from a relatively large size at the proximal receptacle end 412 to a relatively small size at a the distal receptacle end 414. The inner surface 416 is sized and shaped to retain the distal probe tip 224 to prevent the probe tip 224 from moving laterally when the probe tip 224 is fully seated in the probe receptacle 404. The inner surface 416 may be similar in construction to the probe receptacle 304 described in relation to FIGS. 3A and 3B, or have other shapes configured to retain the probe tip 224. For example, the inner surface 416 may comprise a proximal portion adjacent the proximal receptacle end 412 having a first angle $\theta_1$ relative to the longitudinal axis 408 in the range of 20°-30° (e.g., 25°), an intermediate portion located distally from the upper portion having a second angle $\theta_2$ relative to the longitudinal axis 408 in the range of 5°-15° degrees (e.g., 10°), and a distal portion located distally from the intermediate portion having a hemispherical or semi-hemispherical shape having a radius r in the range of 0.3-0.8 mm. This arrangement is expected to provide simple and repeatable installation of the probe tip 224 into the receptacle 404, and provide a distinct feel to indicate when the probe tip 224 is fully seated.

The probe receptacle 404 is positioned adjacent to an introducer tip opening 418 that passes through the distal introducer end 402. The introducer tip opening 418 and probe receptacle 404 are positioned such that fluid can pass through the introducer tip opening 418 without passing through the proximal receptacle end 412. This allows fluid located in a gap 426 between the probe receptacle's outer wall 428 and the introducer sidewall 204 to flow through the introducer tip opening 418 when the probe tip 224 is installed within the probe receptacle 404. In the shown embodiment, the outer wall 428 is shown being spaced from the sidewall 204 around its entire perimeter, but it will be appreciated that the outer wall 428 may merge with the sidewall 204 at some locations (such as when the introducer profile is a narrow ellipse or oval, and the receptacle 404 has a circular profile).

The probe receptacle 404 also may include a distal receptacle opening 420 passing thorough the distal receptacle end 414, to provide an additional flow path when the probe is not installed in the probe receptacle 404, and prevent fluid from pooling in the probe receptacle 404. The distal receptacle end 414 may extend into the introducer tip opening 418, such that it lies at or near the plane of the distal introducer end 402. In this case, the introducer tip opening 418 may be formed as an annular passage that surrounds the probe receptacle 404 with the supports 406 bridging the gap between the distal introducer end 402 and the probe receptacle 404. The supports 406 may include arched voids to help reduce any disruption in the flow through the introducer tip opening 418 that the supports 406 might otherwise cause. As with the embodiment of FIGS. 3A and 3B, locating the distal receptacle end 414 within the introducer tip opening 418 can place the probe tip 224 as close as possible to the distal introducer end 402. However, this arrangement is not required in all embodiments.

In this embodiment, the proximal receptacle end 412 is larger in the lateral direction (i.e., perpendicular to the longitudinal axis 408) than the introducer tip opening 418. This provides a relatively large probe receptacle 404 to help guide the probe 220 into place, while keeping the size of the introducer tip opening 418 relatively small to help prevent the possibility of brain tissue or other delicate tissue being damaged by being forced into or cut by the edges of the introducer tip opening 418. FIG. 4B shows how this configuration helps guide the probe tip 224 into the probe receptacle 404, even when it starts at a location that is significantly offset from the probe receptacle's centerline (which, in this example, is collinear with the geometric center of the introducer 400).

Where the proximal receptacle end 412 is larger than the introducer tip opening 418, it may be particularly favorable to provide additional provisions for assuring suitable flow through the introducer tip opening 418. To this end, the probe receptacle 404 may include one or more (preferably three) openings at a location between the proximal receptacle end 412 and the distal receptacle end 414 to allow fluid to flow to the introducer tip opening 418 without passing through the proximal receptacle end 412. Such openings may be, for example, slots 422 extending inward from the outer surface of the probe receptacle 404 to the introducer tip opening 418. These slots 422 allow fluid to drain from the most distal parts of the introducer passage to prevent pooling around the outer perimeter of the probe receptacle 404 at the distal end of the introducer. The slots 422 in the shown embodiment extend in the longitudinal direction from the proximal receptacle end 412 to a portion of the sidewall 204 located adjacent the distal receptacle end 414, but other embodiments may have slots having different lengths in the longitudinal direction.

Each slot 422 may terminate at its inner end at an annular passage 424 that overlies the introducer tip opening 418. The annular passage 424 passes through the inner surface 416 of the receptacle 424 and extends to the introducer tip opening 418, and is expected to help redistribute fluids passing through the introducer tip opening 418 into a more uniform and less restricted flow. The supports 406 bridge and interrupt the annular passage 424 to join the proximal receptacle end 412 to the distal receptacle end 414 and to suspend the distal receptacle end 414 at the introducer tip opening 418. The slots 422 and annular passage 424 are sized to prevent the probe tip 224 from entering them (e.g., by having a 0.5 mm maximum width if the smallest probe tip 224 to be used is 0.8 mm or larger).

As with the other embodiments, the receptacle 404 is preferably positioned and sized such that a transparent portion of the introducer sidewall 204 at the distal introducer end 402 is visible to the surgeon while the probe tip 224 is installed in the receptacle 404, to allow visualization of the underlying tissue while the probe 220 is in place.

FIGS. 5A through 5D illustrate another embodiment of an introducer 500, of which only the region of the introducer 500 adjacent the distal introducer end 502 is shown. As with the previous embodiments, it will be understood that other features of the introducer 500 will be connected to the illustrated portion. In this embodiment, the introducer 500 has a probe receptacle 504 having primary supports 506 joining a proximal receptacle end 508 to a distal receptacle end 510. The distal receptacle end 510 is adjacent (and preferably within) an introducer tip opening 512. The proximal receptacle end 508 is larger, in a direction perpendicular to the longitudinal axis 514 of the introducer 500, than the introducer tip opening 512. The structure of this probe receptacle 504 is similar to the one illustrated in FIGS. 4A and 4B, and can include the same variations and features (e.g., a distal receptacle opening, etc.). The description of FIGS. 4A and 4B applies equally to the embodiment of FIGS. 5A-5D.

Figure 5A:
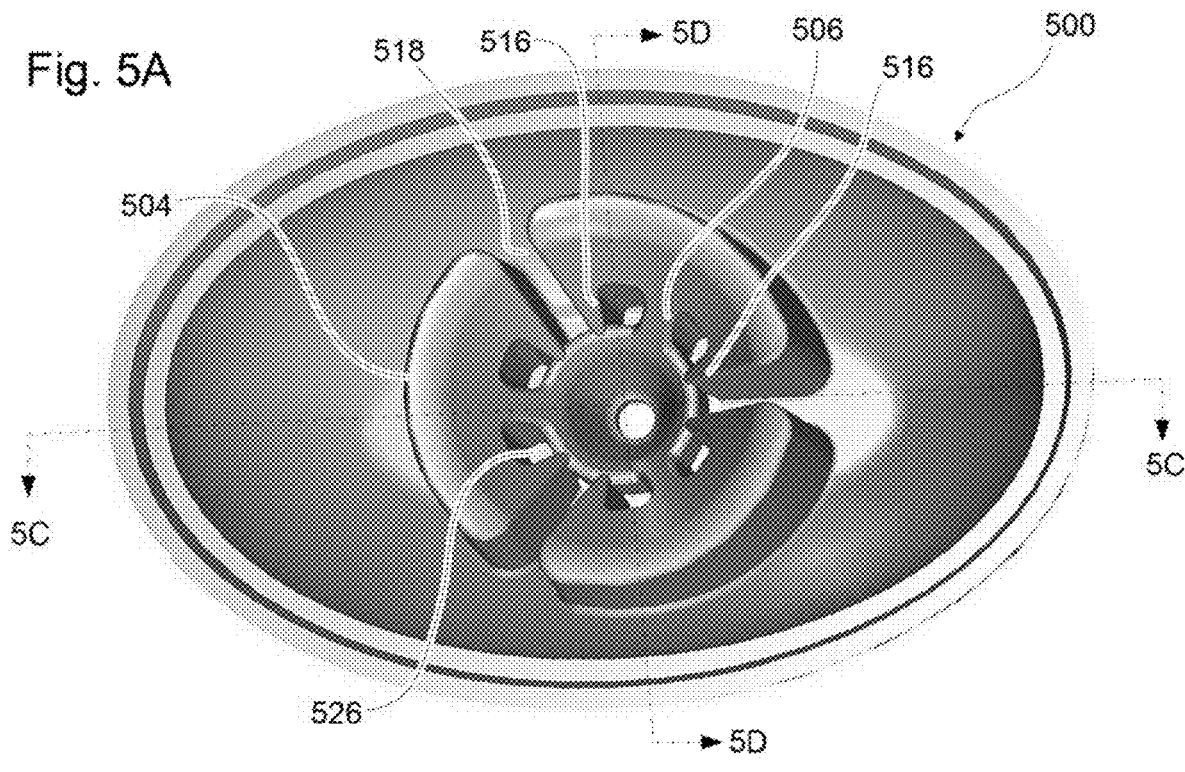
FIG. 5A illustrates a distal tip of another embodiment of an introducer having a guidance probe receptacle, as viewed from inside the introducer.
Figure 5B:
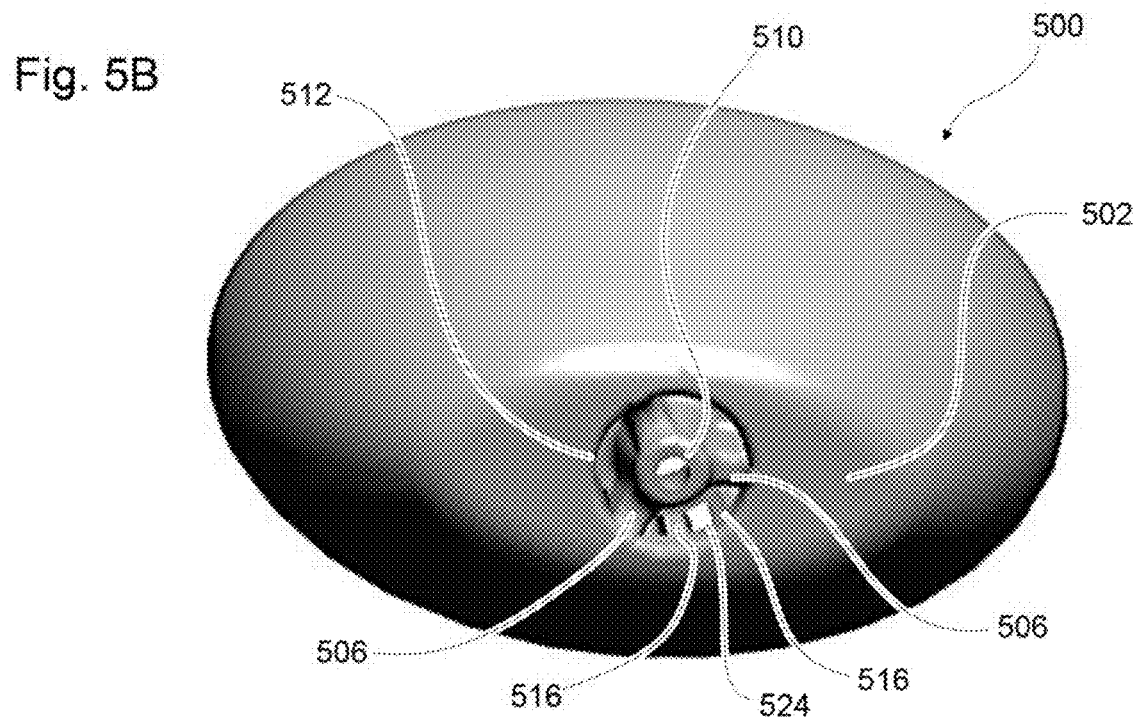
FIG. 5B illustrates the embodiment of FIG. 5A, as viewed from outside the introducer.
Figures 5C, 5D:
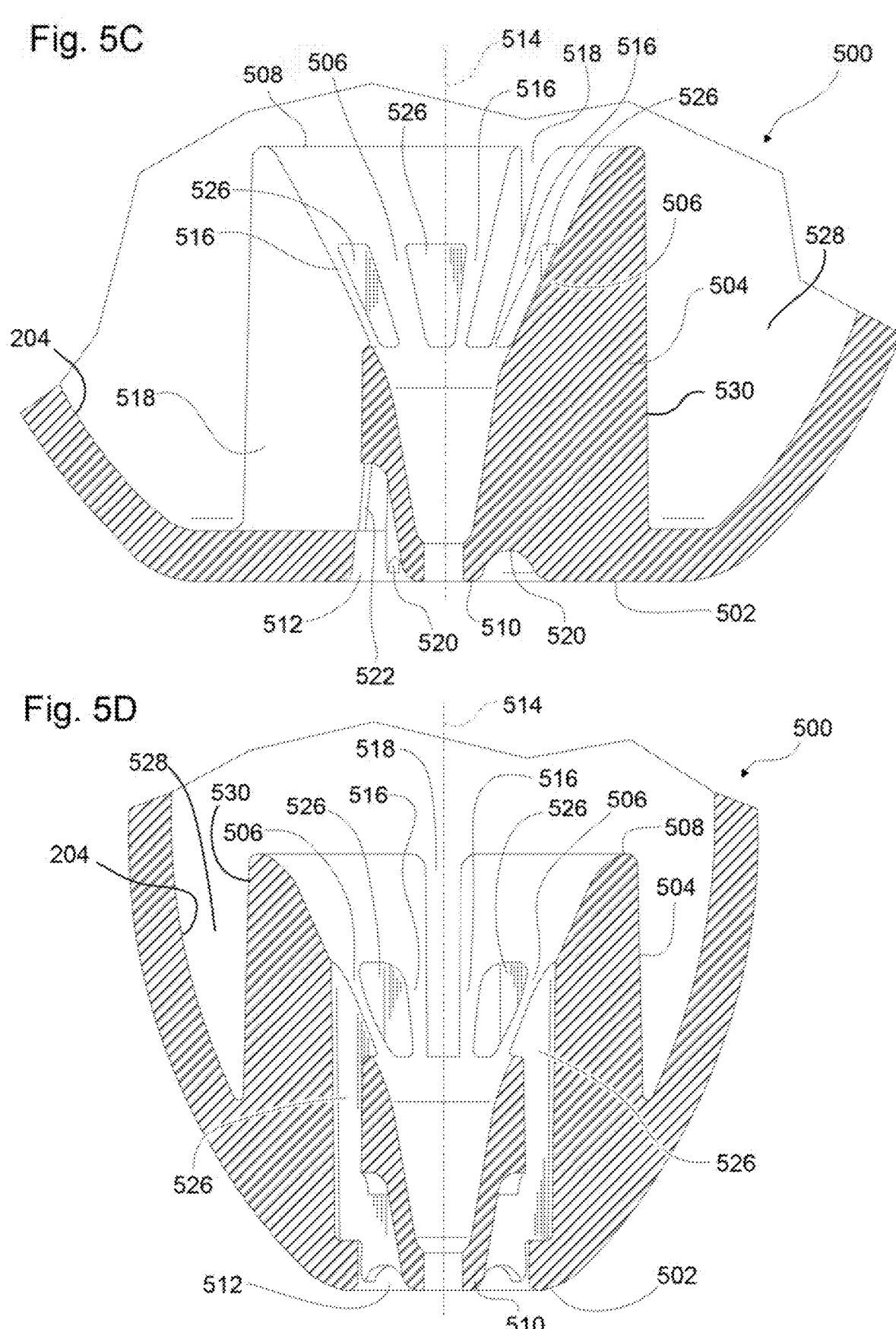
FIG. 5C is a cutaway side view of the distal tip of the embodiment of FIG. 5A, as shown along line 5C-5C.
FIG. 5D is a cutaway side view of the distal tip of the embodiment of FIG. 5A, as shown along line 5D-5D.
Figure 6A:
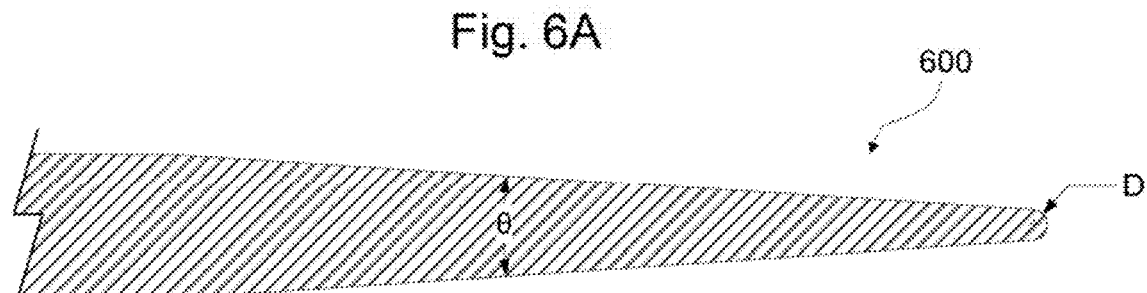
FIGS. 6A-6D are cross-sectional side views of the distal tips of four different navigation probes.
Figure 6B:
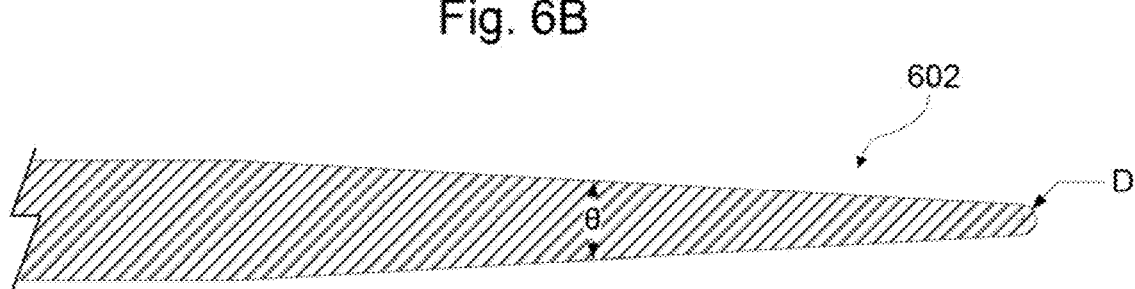
Figure 6C:
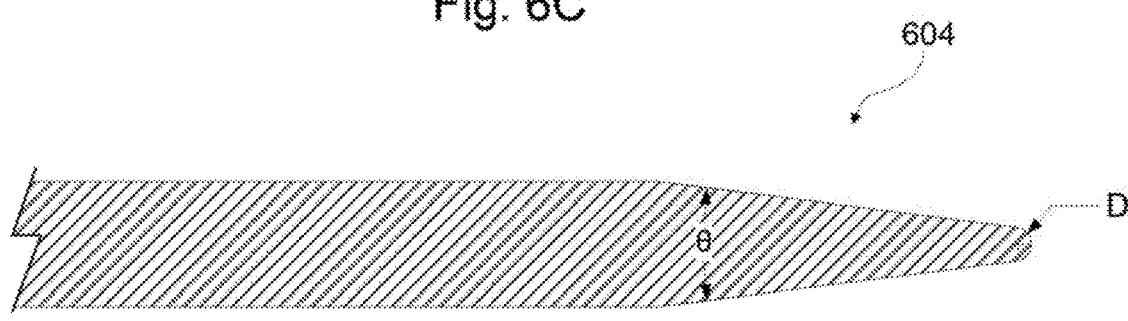
Figure 6D:
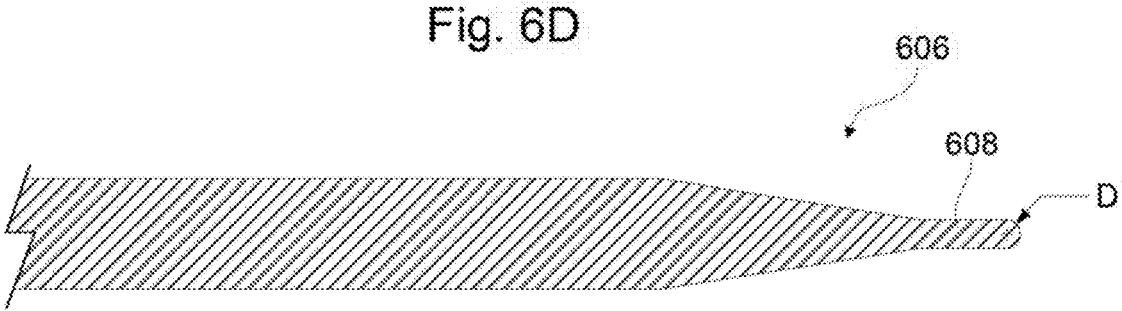

The embodiment of FIGS. 5A-5D differs from FIGS. 4A and 4B in that secondary supports 516 joining the proximal receptacle end 508 to the distal receptacle end 510 are provided on either side of each slot 518. The secondary supports 516 preferably have larger voids at their distal ends to provide a more continuous flow passage adjacent the introducer tip opening 512. For example, the primary supports 506 may be connected to the distal receptacle end 510 by ribs 520 having a lower end located within or near the introducer tip opening 512, while the secondary supports 516 are connected to the distal receptacle end 510 by ribs 522 that are spaced above the introducer tip opening 512, such as best shown in FIG. 5C. This arrangement provides additional structures to support the distal receptacle end 510 and to prevent a surgeon from lodging the probe tip 224 in the slots 518 or the gaps between the proximal receptacle end 508 and the distal receptacle end 510, while still providing an annular passage 524 (FIG. 5B) (which may be interrupted at some locations by the primary support ribs 520) at the introducer tip opening 512 to allow relatively free flow therethrough. Openings 526, located between the secondary supports 516 and primary supports 506, provide flow passages that pass through the inner surface of the probe receptacle 504 and extend along the longitudinal axis 514 to the introducer tip opening 512, to allow vertical fluid flow at various locations. As with the previous embodiments, fluid located in a gap 528 between the probe receptacle's outer wall 530 and the introducer sidewall 204 can flow through the introduced tip opening 512 without having to pass through the proximal introducer end 508, which helps reduce any flow restriction that might be caused by the probe tip 224.

It is also contemplated that the primary supports 506 may be constructed like the shown secondary supports 516 (i.e., with high arched ribs 522 joining to the distal receptacle end 510). However, the lower ribs of the primary supports 506 such as shown in FIGS. 5A-5D may be helpful to add strength and to prevent tissue from entering the introducer tip opening 512. Alternatively, the secondary supports 516 can be structurally identical to the primary supports 506, if it is found that the added support is desirable and the restriction to flow through the introducer tip opening 512 is not unduly compromised. Other alternatives will be apparent to persons of ordinary skill in the art in view of the present disclosure.

The probe receptacle of any given embodiment may have any suitable shape to fit any desired navigation probe. The probe receptacle may be configured to fit one particular kind of probe, or it may be configured to retain a number of different navigation probes. For example, a probe receptacle as described above with reference to FIGS. 2A-5D may be configured to interchangeably receive any one of four or more different probes such illustrated in FIGS. 6A to 6D. A first probe 600 has a tip diameter D of 1.0 mm and a taper angle θ of approximately 6.0°. A second probe 602 has a tip diameter D of 0.8 mm and a taper angle θ of approximately 7.5°. A third probe 604 has a tip diameter D of 1.0 mm and a taper angle θ of approximately 18.0°. A fourth probe 606 has a tip diameter D of 1.0 mm and a 1.0 mm diameter cylindrical shaft 608 extending proximally from the tip. Each of these probes can be inserted with the probe tip seated at the distal end of the receptacle, within 1.0 mm and more preferably within 0.5 mm of the distal introducer end, to hold probe tip against lateral movement.

The receptacle may be formed such that it is not likely for the surgeon to "wedge" the probe tip in place, as this may cause difficulty with removing the probe. To this end, it is preferred for the taper angle of the receptacle's inner wall to not exactly match the taper angle of any particular probe tip in such a way to lock the two parts together. It is also preferred for the material of the receptacle to be relatively hard to prevent it from deforming to allow the probe tip to become lodged therein. Polycarbonate plastic is expected to be suitable for this purpose, but other materials may be used. Of course, a surgeon applying a very large force on the probe might lodge it in the receptacle regardless of how the receptacle is designed, so it will be understood that these preferences are predicated on normal use of the instrument and are not intended to set strict requirements for all embodiments under all circumstances.

Alternatively, the receptacle may be deliberately formed to tend to capture the probe tip in place. For example, the probe tip may include an enlarged end that snaps into a corresponding shape within the receptacle such that a force is required to remove the probe, or the receptacle may include thin deformable ribs that tend to grip the tip of the probe. This may require more care when removing the probe, but add the benefit of not requiring the surgeon to handhold the probe at all times.

The foregoing embodiments are expected to help surgeons use introducer and retractor systems with navigation systems. It is expected that surgeons will use the device by assembling the introducer with a retractor, placing the navigation probe in the introducer until the tip of the probe reaches the end of the probe receptacle, and then advancing the three parts forward into the tissue as a unit. During the process, the surgeon can remove the probe to get a better view into the introducer or to insert other instruments or devices into the introducer. If desired, a clamp or other device may be provided to hold the probe in place to free up the surgeon's hands for other tasks. Examples of clamps are disclosed in the incorporated references, but other mechanisms may be used. Other uses and methods will be apparent to those of ordinary skill in the art in view of this disclosure.

The introducer tip opening may add significant benefits to the system, such as by allowing fluids to ventilate to prevent an excessive accumulation of pressure around the introducer, allowing removal of fluids, and if the opening is large enough allowing resection or manual movement of tissue adjacent the opening. The tip opening also may allow air to vent towards the tissue as the introducer is withdrawn from the retractor after the assembly is placed at the surgery site, which can help prevent the introducer from generating suction that pulls on the tissue as the introducer is withdrawn. Other benefits will be apparent in view of the this disclosure and with further use of the system.

While it is expected that the foregoing embodiments can be used "freehand" by simply placing the probe tip 224 into the probe receptacle, in some cases a surgeon may wish to lock the probe 220 in place within the introducer 200. This may be accomplished by using a retaining mechanism, such as the exemplary probe retainer 700 shown in FIGS. 7A-8B.

The probe retainer 700 comprises a receiver 702 that is affixed to the introducer 200 by a pair of clamps 704. The receiver 702 includes a channel 706 sized to receive a probe 220. The channel 706 preferably is a closed passage having a diameter suitable to accommodate a probe 220, but it may include a longitudinal slot or have a "C" or "U" shaped profile, or the like, in other embodiments. The channel 706 has a proximal channel end 708 facing towards the surgeon, and a distal channel end 710 that extends into the introducer 200. When the probe shaft 222 is located in the channel 706, the channel 706 limits and may completely restrict movement of the probe shaft 222 in the lateral direction.

The receiver 702 may be configured to selectively lock the probe 220 in place within the channel 706. For example, the proximal channel end 708 may have a threaded outer surface 712 that is configured to engage a corresponding lock nut 714, and one or more cutout sections 716 passing through the proximal channel end 708. The threaded outer surface 712 and lock nut 714 are configured such that the lock nut 714 compresses the threaded outer surface 712 as it is tightened onto the threaded outer surface 712, such as by providing one or both with a slight taper or making the lock nut's threads slightly smaller in diameter than the threads on the outer threaded surface 712. The cutout sections 716 provide reliefs to allow the threaded surface 712 to move inwards as the lock nut 714 is tightened. Thus, as the lock nut 714 is tightened on the threaded outer surface 712, the threaded outer surface 712 moves radially inwards, and an inner surface 718 of the proximal channel end 708 clamps against and secures the probe 220 in place. The receiver 702 also may include one or more retaining lips 720 to prevent the lock nut 714 from being fully removed from the receiver 702.

Other locking mechanisms may be used in other embodiments. For example, the lock nut 714 may be replaced by a band clamp, a set screw, or other devices. Examples of alternative locks are provided in the incorporated references, and other options will be apparent to the person of ordinary skill in the art in view of this disclosure.

In the shown embodiment, the receiver 702 may include a number of slots 722 (e.g., three slots) that extend proximally from the distal channel end 710. The exemplary slots 722 extend longitudinally along the longitudinal axis 212 of the assembly, but other orientations may be used (e.g. helical). The inner surface of the channel 706 is also may be gently tapered such that the diameter of the channel 706 decreases as it approaches the distal channel end 710. The final diameter of the channel 706 at the distal channel end 710 may be slightly less than the largest diameter probe 220 expected to be used with the device, such that the probe 220 is slightly compressed by the receiver 702 at the distal channel end 710. The slots 722 allow the channel 706 to flex outwards at the distal channel end 710 to accommodate probes 220 of different sizes. This feature is expected to provide a useful slight retaining force, and may help center the probe 220 within the channel 706.

The receiver also may be configured to direct the distal probe tip 224 towards a receptacle (e.g., receptacle 230, 304, 404 or 504) as the probe 220 is installed into the introducer 200. The foregoing tapered and slotted arrangement is expected to accomplish this by orienting the channel 706 towards a corresponding receptacle at the distal introducer tip, but other embodiments may use other configurations to do the same thing. Preferably, the channel 706 extends in the longitudinal direction, so that it prevents significant angulation of the probe 220 within the channel 706 (i.e., it prevents angulation that could prevent the distal probe tip 224 from entering the receptacle). For example, the channel 706 may have an inner diameter that is no more than 110% of the largest probe diameter, and a length that is at least 300% and more preferably at least 1000% of the largest probe diameter.

Despite the foregoing, in other embodiments the channel 706 may comprise a simple ring or passage that is not tapered and does not include slots, or the taper and slots may be replaced by a flexible diaphragm or cantilevered arms that help center the probe 220 within the channel 706. Other alternatives will be apparent to persons of ordinary skill in the art in view of the present disclosure.

The clamps 704 are attached to the receiver 702, and configured to hold the receiver 702 at a fixed location relative to the introducer 200. The receiver 702 may be centered on the introducer 200, such as shown, or it may be offset from the introducer's centerline. In this embodiment, the clamps 704 are connected to the receiver 702 by clamp arms 724 that are shaped to generally match the shape of the introducer sidewall 204 at the proximal introducer end 206. Thus, each clamp arm 724 has an opening 726 through which the surgeon can view into the introducer passage 210.

Each clamp 704 comprises a tab 728 that is shaped to receive a user's finger, and a hook 730 that is shaped to wrap around a corresponding lip 800 (FIGS. 8A-B) on the introducer. The clamp arms 724 are located between the tab 728 and the hook 730. The clamp arms 724 and hooks 730 are movable between a latched position in which the hooks 730 are relatively close to one another, and an unlatched position in which the hooks 730 are relatively far from one another. In their latched position, the hooks 730 are spaced by a first distance at which they wrap around the corresponding lips 800 to secure the probe retainer 700 to the introducer 200. The hook spacing in the latched position may be slightly greater than their natural resting position when not attached to an introducer 200. Thus, when attached to the introducer 200, the clamp arms 724 may be under a slight bending force caused by flexing the hooks 730 from their resting position to their latched position. This can help provide a stronger locking connection, and may reduce the likelihood of shifting or moving when connected.

When the surgeon pinches the tabs 728 together, the clamp arms 724 flex and provide a fulcrum about which the hooks 730 rotate until they are located at a second distance from one another. In this position, the hooks 730 release the lips 800 and the probe retainer 70 can be removed from the introducer. The clamps 704 may be reinstalled onto the introducer 200 by reversing this operation, and the hooks 730 may include ramped surfaces to allow them to be snapped onto the lips 800 simply by pressing the probe retainer 700 against the proximal introducer end 206.

In the exemplary embodiment, there are two clamp arms 724, each of which has two spaced portions that surround an opening 726 to allow visualization into the introducer 200. Each clamp arm 724 is connected to the receiver 702 at two locations on opposite sides of the receiver 702. The attachments between the receiver 702 and the clamp arms 724 may have buttresses 732 to increase the rigidity of the connection. This is expected to help the clamp arms 724 flex in a more predictable manner during the detachment and installation process.

The foregoing clamp 704 arrangement is expected to provide simple and reliable engagement to selectively connect the probe retainer 700 to the introducer 200. However, other embodiments may use different structures to hold the probe in place. For example, the flexible clamp arms 724 may be replaced by more rigid members having a mechanical pivot such as a pivot pin or the like and a return spring to bias the hooks 730 to the clamped position. As another example, each clamp arm 724 may have a single portion located on one side of the introducer 200, rather than two spaced portions, and the clamps 704 may be turned 90° relative to the shown position such that the grip the introducer 200 from the side rather than from the top. Other alternatives will be apparent to persons of ordinary skill in the art in view of the present disclosure.

Figures 7A, 7B:
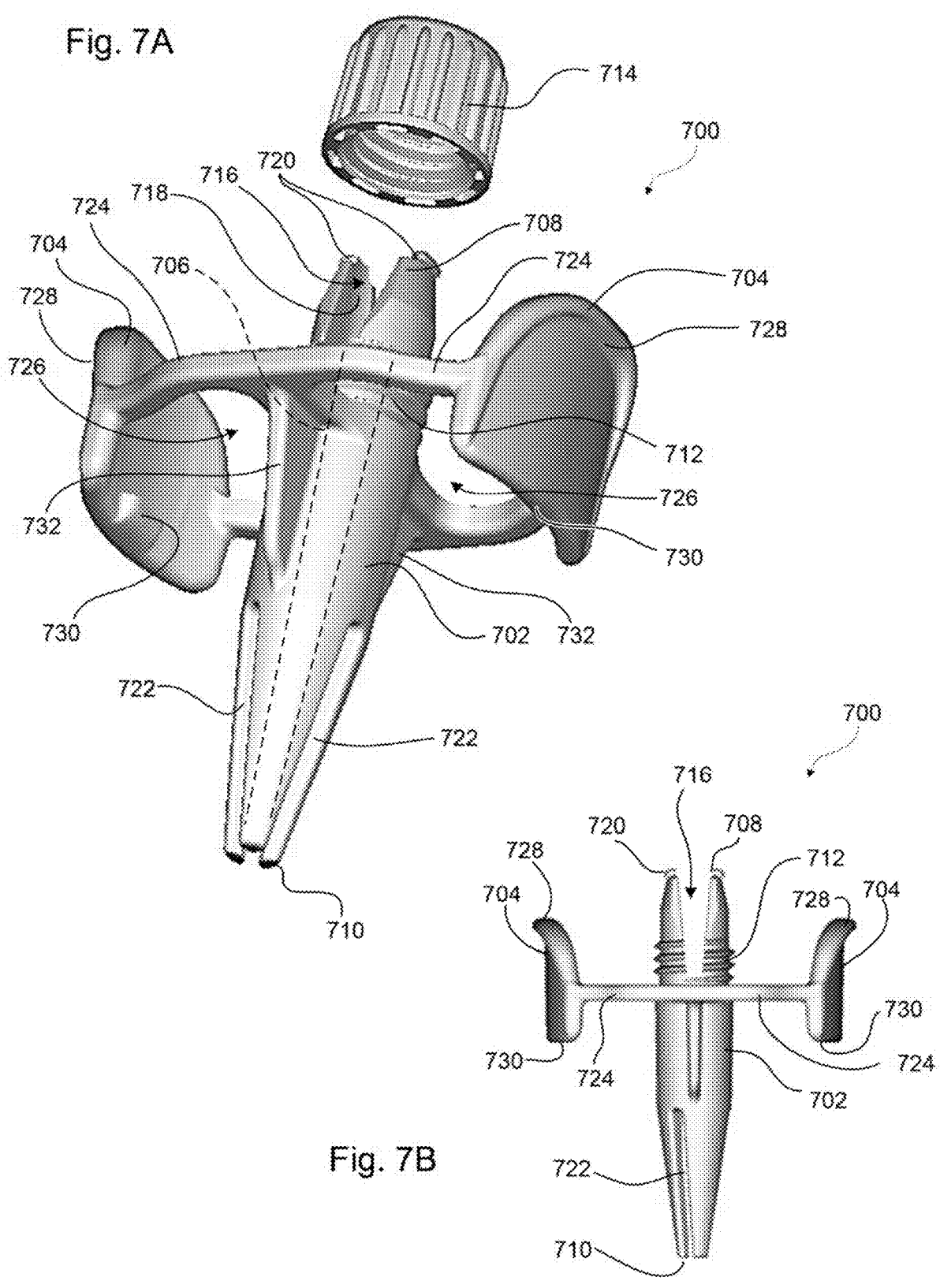
FIGS. 7A-7B illustrate an embodiment of a centering device that may be used with embodiments of introducers.
Figures 8A, 8B:
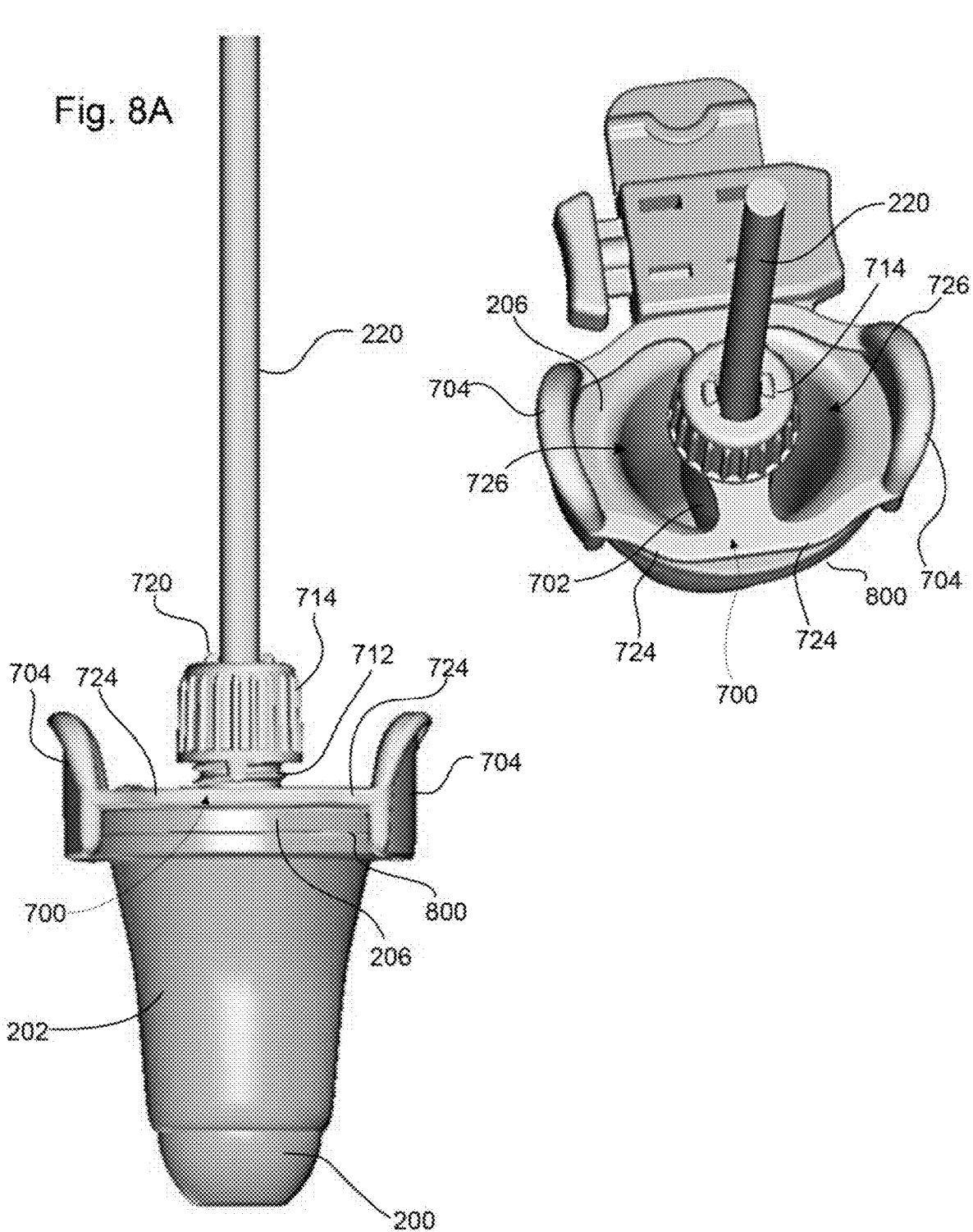
FIGS. 8A-8B illustrate the embodiment of FIGS. 7A-7B in use.

FIGS. 8A and 8B show the embodiment of FIGS. 7A-B as it appears when installed on an exemplary introducer 200. The introducer 200 is shown assembled with a corresponding retractor 202. The introducer 200 preferably includes a probe tip receptacle such as those described previously herein, but it is also envisioned that the probe retainer 700 may be used with introducers that do not have a probe tip receptacle, such as those discussed with reference to FIG. 1. The assembly of the probe retainer 700 and navigation probe 220 preferably can be removed from or installed into the introducer 200 without separating the introducer 200 from the retractor 202. This provides rapid access to the introducer interior, if necessary.

Figures 9A, 9B:
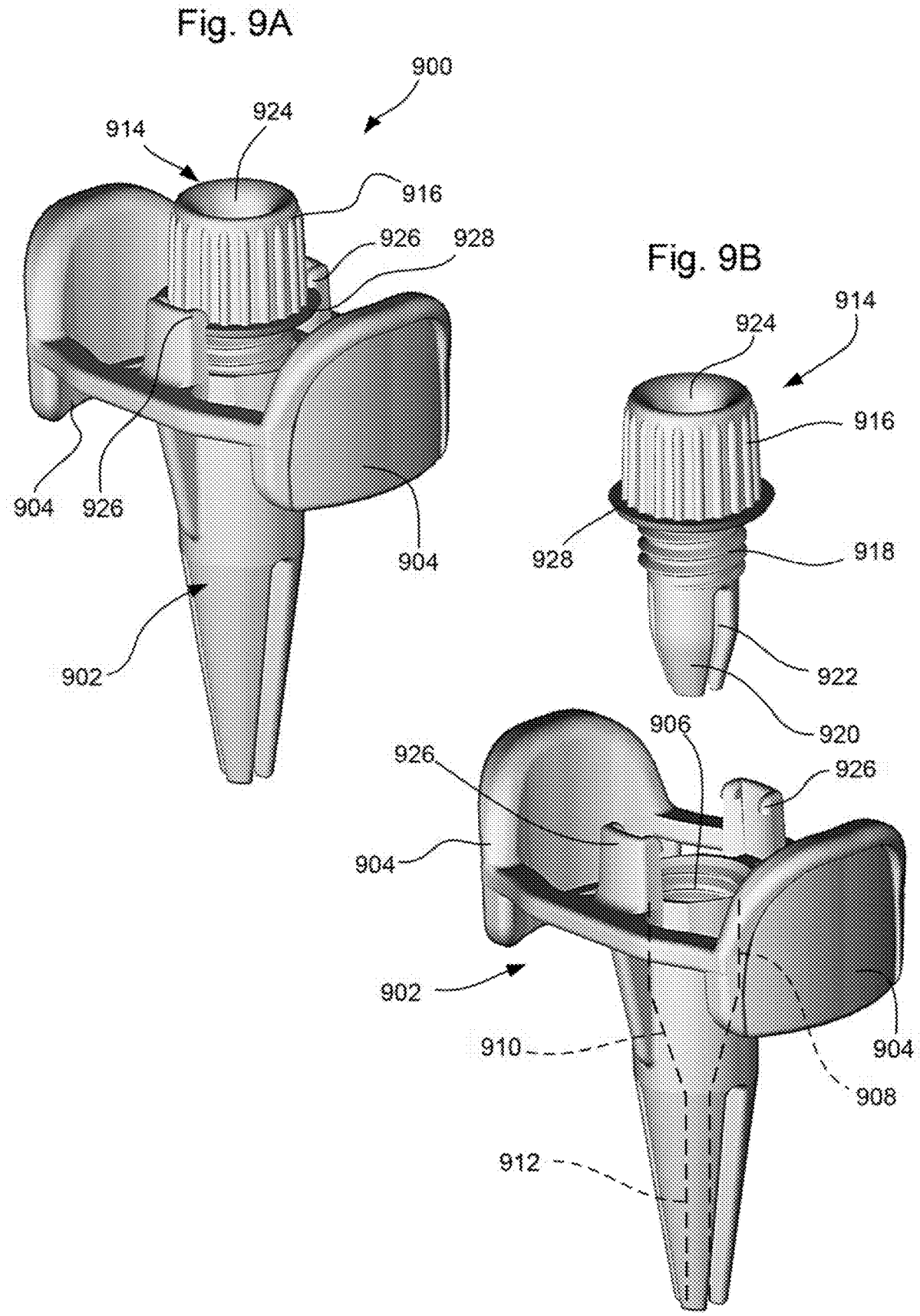
FIGS. 9A and 9B are assembled and exploded views, respectively, of an alternative embodiment of a centering device and probe retainer system.

FIGS. 9A and 9B show another embodiment of a probe retainer 900. In this case, the probe retainer includes a receiver 902 that can be affixed to an by a pair of clamps 904. This embodiment is generally the same as the embodiment of FIGS. 7 through 8B. However, in this embodiment the mechanism for locking the probe shaft in place is different. The receiver channel 906 is formed with a threaded proximal end 908, a conically tapered central portion 910, and a relatively narrow distal portion 912. The locking nut 914 comprises a proximal knob portion 916 that is adapted for use by the surgeon (e.g., knurled, or otherwise shaped to be engaged by fingers or a tool), a male-threaded central portion 918, and a tapered conical distal end 920 having one or more longitudinal slots 922. A central passage 924 passes through the locking nut 914 to receive the probe shaft. The threads 918 of the locking nut 914 are configured to thread into the threads 908 of the receiver 902, and the conical distal end 920 of the locking nut 914 is dimensioned to fit into the conical central portion 910 of the receiver 902. The locking nut 914 is advanced into the receiver 902 by rotating it relative to the receiver 902. When the tapered end 920 of the locking nut 914 engages the tapered central portion 916 of the receiver channel 906, contact between the parts flexes the tapered end 920 radially inwards to compress against the probe shaft. Thus, the locking nut 914 can cooperate with the receiver 902 to engage and hold the probe shaft at a fixed location.

The locking nut 914 may be retained by one or more features that interlock with the receiver 902. For example, the receiver 902 may have one or more hooks 926 that surround a lip 928 that extends radially from the knob portion 916 of the locking nut 914. These retaining features inhibit the locking nut 914 from accidentally separating from the receiver 902 when the locking nut 914 is fully-loosened. However, in some embodiments, the hooks 926 may be designed to be deformable to allow the locking nut 914 to be removed. Other alternatives and variations will be apparent to persons of ordinary skill in the art in view of the present disclosure.

It will be appreciated that the foregoing embodiments may be modified in various ways. As one example, features disclosed in one embodiment may be used with any of the other embodiments. As another example, the probe receptacles described herein can be formed integrally with the introducer by additive manufacturing or molding (the illustrated embodiments show various configurations in which conventional two-part injection molding processes may be used to make the introducer and probe receptacle as a single integrally molded part), or formed separately and attached to the introducer. As another example, the probe receptacle may have any sidewall profile shape, rather than the generally circular shapes shown in the embodiments. The probe receptacles also may have any combination of conical, cylindrical, hemispherical, or other shapes. It is also envisioned that the probe receptacle may have openings such as the flow passages of FIG. 2B and slots of the later embodiments, even when the introducer does not have an introducer tip opening, which can be beneficial to displace fluid from the receptacle to allow free entry of the probe tip. Other alternatives will be apparent to persons of ordinary skill in the art in view of the present disclosure.

Referring now to FIGS. 10A-17, additional embodiments are shown with a different construction for the probe receptacle and other features that address shortcoming that have been identified with prior art systems. For example, it has been determined that the probe tip retaining structures described in United States Patent Publication Number 2016/0015375 can fail to provide proper registration of the probe tip at the desired location due to excess play between the probe tip and the introducer structure. In particular, when used without a registration indicator, a probe tip can be lodged in the corner between the stop surface and the sliding mount, regardless of whether the stop surface has a feature (e.g., ring or ribs) to hold the probe tip in place. Furthermore, the probe tip can be placed between the sliding mount and the outer wall of the introducer. Such issues can arise from excess tolerances and from the fact that the clamp mechanism is openable to a position that allows rotation of the probe relative to the clamp prior to full engagement of the clamp. If the probe is rotated prior to clamping, it can be directed to any number of incorrect locations, and subsequently operating the clamp may not reposition the probe tip (and may bend or damage the probe and potentially break parts of the introducer). Thus, while this reference discusses configuring the stop surface to retain the probe tip at the desired location when a registration indicator is not used, the structure and inherent nature of the clamping device allow displacement of the probe tip in an unfavorable manner, and do not provide a secure seating for the probe tip at the desired registration position in the absence of the registration indicator.

The embodiments of FIGS. 10A-23 also address potential shortcomings and inefficiencies of the embodiments discussed in relation to FIGS. 2A through 5D. For example, the foregoing embodiments use tapered surfaces to guide the probe tip to the desired location, which addresses the shortcomings of United States Patent Publication Number 2016/0015375 as described immediately above. These tapered surfaces can be beneficial to facilitate proper insertion of the probe tip. However, such tapered surfaces can have various shortcomings. For example, the surfaces require complex geometry, which can obstruct and distort the surgeon's view though the introducer wall, and can be relatively complicated to design and manufacture (e.g., maintaining a uniform part thickness to ensure uniform molding is relatively difficult, and small insert pins to form small voids are prone to breaking).

The tapered surfaces of the probe receptacle can also generate aligning forces when they interact with the tapered probe tip, which can be problematic in certain situations. For example, it is often desirable to insert the navigation probe during the course of surgery, without using the probe retainer, to quickly check the introducer's position. During such use, it is not strictly necessary to orient the navigation probe along the axis of the introducer, because the most relevant position is often the very tip of the introducer. Thus, the probe may be held at an angle relative to the longitudinal axis of the introducer—for example, the surgeon may hold the probe at an angle to minimize the probe's obstruction of his or her view down the introducer and to leave room for other surgical instruments. However, when the tapered wall of the probe reaches the tapered wall of the probe receptacle, the walls act on each other to try to force the probe into alignment with the introducer's longitudinal axis. Such forces can interfere with the desire to hold the tip of the probe at the registration position while tilting the probe relative to the longitudinal axis to maintain view or access for other devices. Such forces can also cause the introducer to move laterally within the surrounding tissue.

It is also expected that interaction between the tapered surfaces of the probe tip and the tapered surfaces of the probe receptacle can generate other conditions that may not be desired. For example, fluid trapped between similarly tapered surfaces can be relatively difficult to evacuate when trying to mate the surfaces together, due to increase surface tension and the need to evacuate a relatively large volume of liquid trapped between the impinging surfaces. This may also lead to a suction-like resistance against separating the surfaces from one another.

While the foregoing issues are not necessarily experienced or problematic in use, it has been determined that the need for such tapered surfaces can be eliminated by using the self-aligning properties of the tapered navigation probe tip to provide proper guidance to the registration position, and/or by providing a probe retainer that ensures proper positioning of the probe tip when the parts are assembled, without relying on tapered surfaces of the probe receptacle. Eliminating the tapered surfaces can help alleviate one or more of the foregoing issues, but it will be understood that there is no strict requirement for any of the claimed structures to provide a particular set of benefits or capabilities as compared to other devices.

A first example of an alternative surgical introducer system 1000 is illustrated in FIGS. 10A-10D. The surgical introducer system 1000 is configured for use with a navigation probe 1002 having a navigation element 1004, a probe shaft 1006 connected to the navigation element 1004, and a distal probe tip 1008 extending from the probe shaft 1006. The navigation element 1004 may comprise a conventional infrared reflector assembly or any other suitable navigation device (e.g., magnetic, sonar, etc.). The shown navigation element 1004 is attached to a proximal end of the probe shaft 1006 such that it is exposed to the surrounding environment for viewing by an optical system, but other navigation elements 1004 may be connected to the probe shaft 1006 (or probe tip 1008) at other locations. The probe tip 1008 tapers from a first probe diameter D1 at the probe shaft 1006 to a second probe diameter D2 at a distal terminal end 1010 of the probe tip 1008, with the second probe diameter D2 being less than the first probe diameter D1. The tapered shape may comprise a continuous conical surface, but this is not strictly required (see, e.g., FIG. 6D). The portion of the probe tip 1008 at the terminal end 1010 may be hemispherical, rounded or flat.

The introducer system 1000 includes an introducer 1012 having an outer introducer sidewall 1014 that extends along a longitudinal axis 1016 from a proximal introducer end 1018 to a distal introducer end 1020. The outer introducer sidewall 1014 preferably is tapered and/or rounded at the distal introducer end 1020 to form an atraumatic surface for parting delicate tissue such as brain tissue. The remainder of the outer introducer sidewall 1014 also may be tapered to generally narrow in size perpendicular to the longitudinal axis 1016 as it extends from the proximal introducer end 1018 towards the distal introducer end 1020, but such taper is not strictly necessary. The outer introducer sidewall 1014 may have a circular or ovate profile as viewed along the longitudinal axis 1016, but other shapes may be used.

The introducer 1012 has an inner introducer sidewall 1022, which extends within the outer introducer sidewall 1012 along the longitudinal axis 1016, and defines an introducer passage 1024. The introducer passage 1024 extends distally from a proximal passage opening 1026 at the proximal end 1018 of the introducer 1012 to an introducer passage end wall 1028 located proximal to the distal introducer end 1020. The inner introducer sidewall 1022— and thus the introducer passage 1024—may have a circular, ovate or other profile as viewed along the longitudinal axis 1016. The inner introducer sidewall 1022 and introducer passage 1024 also may be tapered to reduce in size, in a direction perpendicular to the longitudinal axis, from a first introducer passage size at the proximal introducer end 1018 to a second introducer passage size at the introducer passage end wall 1028.

The outer introducer sidewall 1014 and inner introducer sidewall 1022 define between them the wall thickness t of the introducer 1012. The wall thickness t may vary in size at different locations along the introducer 1012, but preferably is generally uniform in size between the proximal introducer end 1018 and the introducer passage end wall 1028. For example, the wall thickness t may vary by less than 20% along the length of the introducer 1012 extending between a radially-flared flange 1030 at the proximal introducer end 1018 and the end wall 1028. The introducer 1012 preferably is made completely or partially of a transparent, biocompatible material, such as polycarbonate plastic, but other materials may be used.

The outer introducer sidewall 1014 preferably is configured to fit within a retractor 1032, which may be provided as part of the surgical introducer system 100. The retractor 1032 has a hollow body extending from a proximal retractor end 1034 to a distal retractor end 1034. The retractor 1032 is selectively securable to the introducer 1012 (e.g., by clips, cooperating shapes of the parts, by a surgeon's hand, etc.) in an introducing configuration in which the hollow body surrounds the outer introducer sidewall 1014, with the proximal retractor end 1034 adjacent to the proximal introducer end 1018, and the distal retractor end 1036 between the proximal introducer end 1018 and the distal introducer end 1020. The retractor 1032 may be used at a surgical site after the inducer 1012 is removed to provide an access passage for surgical operations. In the shown example, the retractor 1032 is tapered in a manner similar to the introducer 1012 to thereby fit securely to the outer surface of the introducer 1012. If the introducer 1012 and retractor 1032 are not tapered, the introducer 1012 may have a flange 1030 or other structure to prevent over-insertion into the retractor 1032. The retractor 1032 preferably is partially or completely transparent (e.g., transparent polycarbonate plastic) but this is not strictly required. In addition, the distal retractor end 1036 may be shaped to taper or blend into the adjacent portion of the outer introducer sidewall 1014 to help ensure atraumatic spreading of tissue at this location.

Figure 10A:
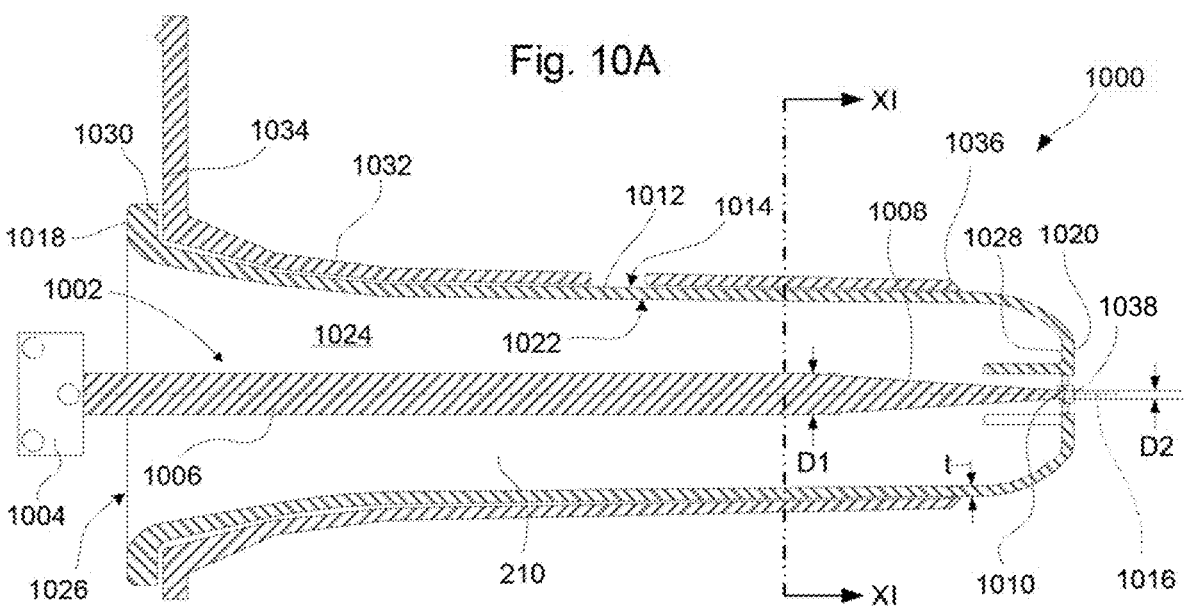
FIG. 10A shows a cutaway side view of another exemplary embodiment of a surgical introducer system.
Figure 10B:
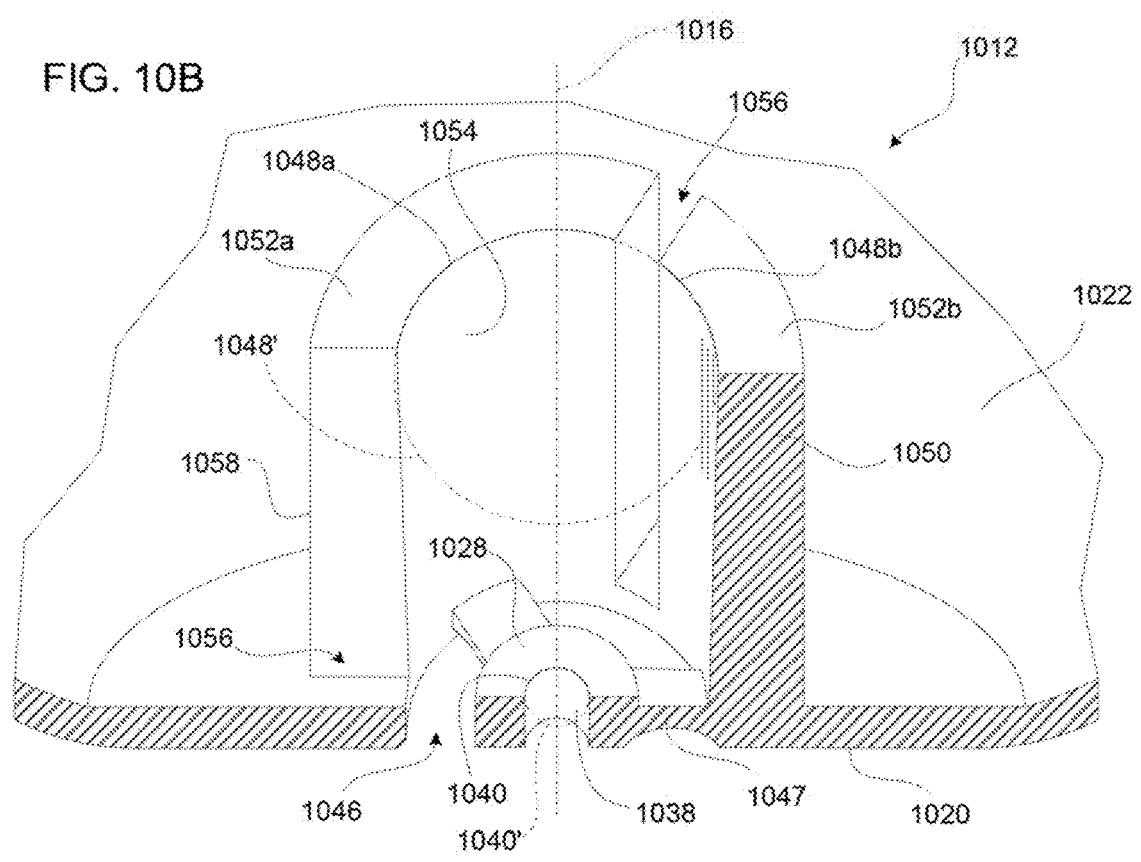
FIG. 10B shows the distal introducer end of the embodiment of FIG. 10A in cutaway isometric view.
Figures 10C, 10D:
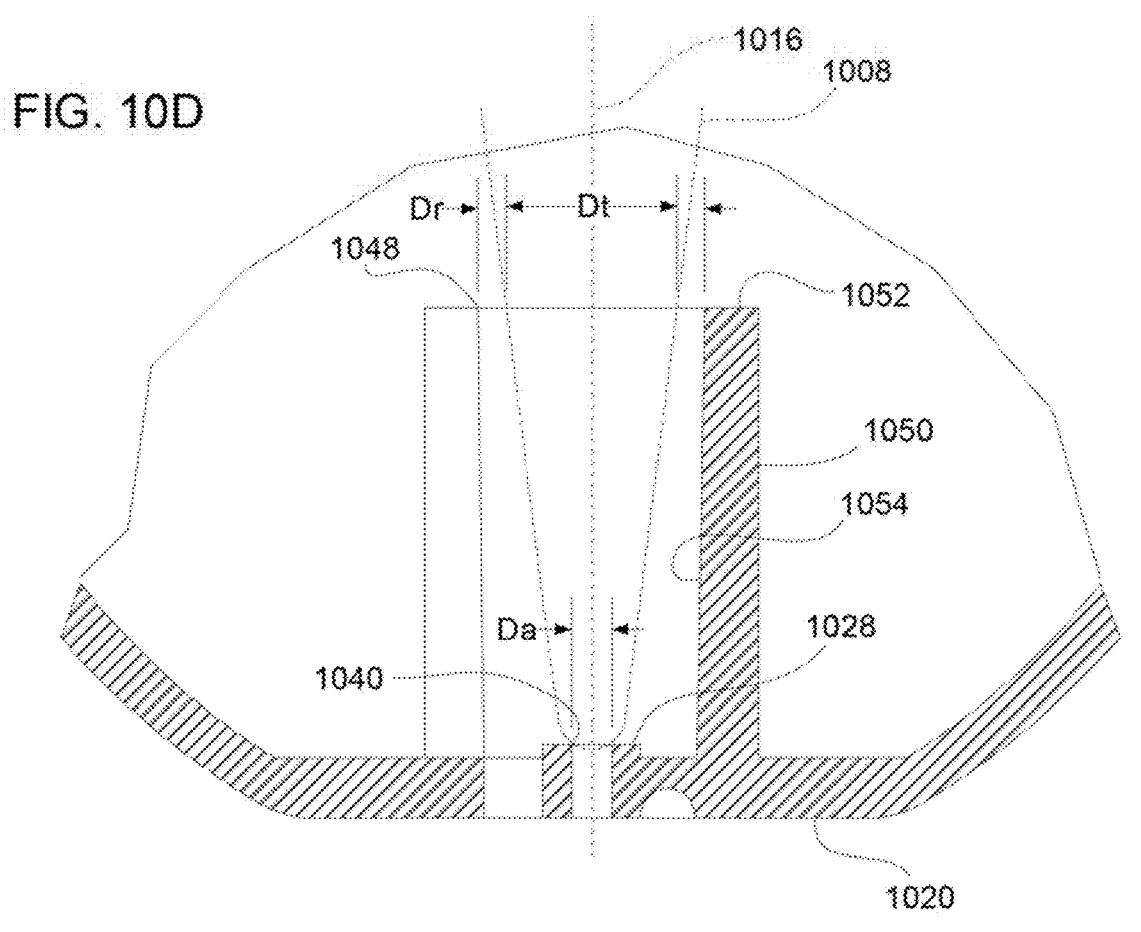

Referring more specifically to FIGS. 10B to 10D to show details, the end wall 1028 includes an end wall passage 1038 extending from the end wall 1028 towards the distal introducer end 1020. The end wall passage 1038 joins the introducer end wall 1028 at one or more end wall edges 1040. The end wall edges 1040 preferably are discrete sharp corners having an angle of approximately 90° between the introducer end wall 1028 and the end wall passage 1038, but this is not strictly required. In the example of FIGS. 10A-10D, the end wall passage 1038 joins the introducer end wall 1028 at a single circular end wall edge 1040 that lies in the plane of the end wall 1028.

The end wall edge 1040 defines an axial stop ring 1040' that is located in the plane of the end wall 1028, and shaped and dimensioned to contact the distal probe tip 1008 between the probe shaft 1006 and the terminal end 1010 of the distal probe tip 1008. More particularly, the distal probe tip 1008 and the end wall edge 1040 contact one another along a circular line of contact 1042 in the plane of the end wall 1028, where the end wall edge 1040 and the adjacent surface 1044 of the distal probe tip 1008 meet. The line of contact 1042 may be continuous, such when a conical or spherical probe tip surface 1044 contacts a continuous circular end wall edge 1040. Alternatively, the line of contact may be discontinuous, such as when a conical or spherical probe tip surface 1044 contacts a series of end wall edges 1040 that are arranged around a common center (see FIG. 11), or when the probe tip surface 1044 comprises a non-circular shape that contacts a circular end wall edge 1040 or the like.

The end wall edge 1040 may be dimensioned to hold a variety of different navigation probes 1002 at the circular line of contact 1042. For example, the end wall edge 1040 may have a diameter selected to contact a variety of probes having rounded or conical distal probe tips 1008, such that the rounded or conical distal probe tips 1008 will all fit, to some degree, into the end wall passage 1038 far enough to allow a portion of the distal probe tip 1008 to engage the end wall edge 1040. Thus, the different navigation probes 1002 are all held in the same plane relative to the longitudinal axis 1016. The end wall edge 1040 also preferably is selected to hold each type of navigation probe 1002 with its respective terminal end 1010 at a location within the confines of the outer introducer sidewall 1014, so that the terminal end 1010 cannot contact tissue into which the introducer 1012 is moved.

The end wall edge 1040 (or edges), and thus the axial stop ring 1040', may be located at any location throughout the introducer end wall 1028, but most preferably is centered on the centerline of the introducer passage 1024, which is represented in the Figures by the longitudinal axis 1016. This arrangement holds the navigation probe terminal end 1010 at what is typically considered to be the most relevant part of the introducer 1012 for surgical navigation purposes (i.e., the center of the distal introducer end 1020), thus simplifying registration of the surgical introducer system 1000 with an associated navigation tracking system.

The end wall passage 1038 can have any geometry between the end wall edge 1040 (or edges) and the distal introducer end 1020, provided the geometry does not interfere with proper contact between the distal probe tip 1008 and the end wall edge 1040. In the example of FIGS. 10A-10D, the end wall passage 1038 extends fully through the introducer from the introducer passage end wall 1028 to the distal introducer end 1020 to thereby form a central fluid passage between the introducer passage 1024 and an exterior of the introducer. The end wall passage 1038 is generally cylindrical (i.e., machined or molded as a cylindrical shape within the capabilities of the relevant technology). However, the end wall passage 1038 may have shape that tapers to be smaller or larger, in a direction perpendicular to the longitudinal axis 1016, as it extends towards the distal introducer end 1020, provided the taper angle does not result in surface-to-surface contact between the tapered wall of the end wall passage 1038 and the distal probe tip 1008 of the navigation probe 1002.

The introducer 1012 optionally may include one or more offset fluid passages 1046 positioned adjacent to the end wall passage 1038, and extending from the introducer passage 1024 to an exterior of the introducer 1012. In the example of FIGS. 10A-10D, the introducer 1012 has three offset fluid passages 1046 located in a ring around the introducer passage 1024. In this configuration, the introducer passage end wall 1028 is suspended within the offset fluid passages 1046 by arms 1047. The offset fluid passages 1046 can serve the same functions as the introducer tip openings described in relation to FIGS. 3A-5D. For example, the offset fluid passages 1046 allow fluid to pass into and out of the introducer passage 1024, thereby alleviating pressure and suction that might otherwise develop during insertion and removal of the introducer 1012.

The introducer 1012 optionally may include one or more intermediate wall edges 1048 (individually identified as 1048a, 1048b, etc.) defining a radial stop ring 1048' located between the introducer passage end wall 1028 and the proximal introducer end 1018. The intermediate wall edges 1048 are located in a common plane extending perpendicular to the longitudinal axis 1016, such that the radial stop ring 1048' also lies in this plane. The radial stop ring 1048' is arranged concentrically with the axial stop ring 1040' in relation to the longitudinal direction 1016, and, as shown in FIG. 10D, has a diameter Dr that is greater than a diameter Da of the axial stop ring 1040'.

The diameter Dr of the radial stop ring 1048' preferably is greater than a diameter Dt of a portion of the navigation probe 1002 located within the plane of the radial stop ring 1048' when the distal probe tip 1008 is in contact with the axial stop ring 1040'. In this example, the tapering distal probe tip 1008 lies in the plane of the radial stop ring 1048', but in other cases the radial stop ring 1048' may be positioned along the longitudinal axis 1016 to surround a cylindrical or non-tapering portion of the probe shaft 1006. With this arrangement, the probe 1002 can slide along the radial stop ring 1048' using the tapered surface of the tip 1008 to guide the probe 1002 to the axial stop ring 1040'. The probe 1002 can also be inserted into contact with the axial stop ring 1040' and still be spaced away from (i.e., not in contact with) the radial stop ring 1048' and the intermediate wall edges 1048 forming the radial stop ring 1048', by orienting the probe shaft 1006 parallel to the longitudinal axis 1016, such as shown in FIG. 10D.

The intermediate wall edges 1048 may be formed on extensions of the inner introducer sidewall 1022, such as a protrusion extending radially from the inner introducer sidewall 1022 towards the centerline of the introducer passage 1024. More preferably, the intermediate wall edges 1048 are formed by a proximal end of a probe receptacle 1050 extending along the longitudinal axis 1016 from a location adjacent to the introducer passage end wall 1028. More specifically, the probe receptacle 1050 comprises a proximal end surface 1052, which in this case is defined by segments 1052a, 1052b, which joins an inner receptacle surface 1054 at an angle to form the intermediate wall edges 1048. The intermediate wall edges preferably are relatively sharp edges that are not tapered, such that any contact between the intermediate wall edges 1048 and the navigation probe 1002 is limited to a line of contact extending in the plane of the radial stop ring 1048'. The proximal end surface 1052 may be tapered, but preferably is configured such that the navigation probe 1002 is incapable of being oriented to contact the proximal end surface 1052 once the distal terminal end 1010 of the probe tip 1008 is positioned between the plane of the radial stop ring 1048' and the axial stop ring 1040'. In this configuration, the tapered proximal end surface 1052 may help guide the probe tip 1008 towards the centerline of the introducer passage 1024, but once the distal terminal end 1010 passes beyond the plane of the radial stop ring 1048' any such guidance caused by the tapered proximal end surface 1052 stops. In a more preferred embodiment, the proximal end surface 1052 extends perpendicular to the longitudinal axis 1016 and in the plane of the radial stop ring 1048'.

The probe receptacle 1050 may include one or more lateral openings 1056 extending adjacent to the introducer passage end wall 1028, to thereby form one or more fluid communication paths from a portion of the introducer passage 1024 located between an outer wall 1058 of the probe receptacle and the inner introducer sidewall 1022, to a location adjacent to the end wall passage 1038. The lateral openings 1056 can provide the same functions as described above in relation to the slots of FIGS. 4A-5D-such as to help prevent fluid from accumulating in the space between the probe receptacle 1050 and the inner introducer sidewall 1022. The lateral openings 1056 may be formed as slots that extend along the full distance of the probe receptacle 1050 along the longitudinal axis 1016, or they may extend only partially along the length of the probe receptacle 1050.

Figure 11:
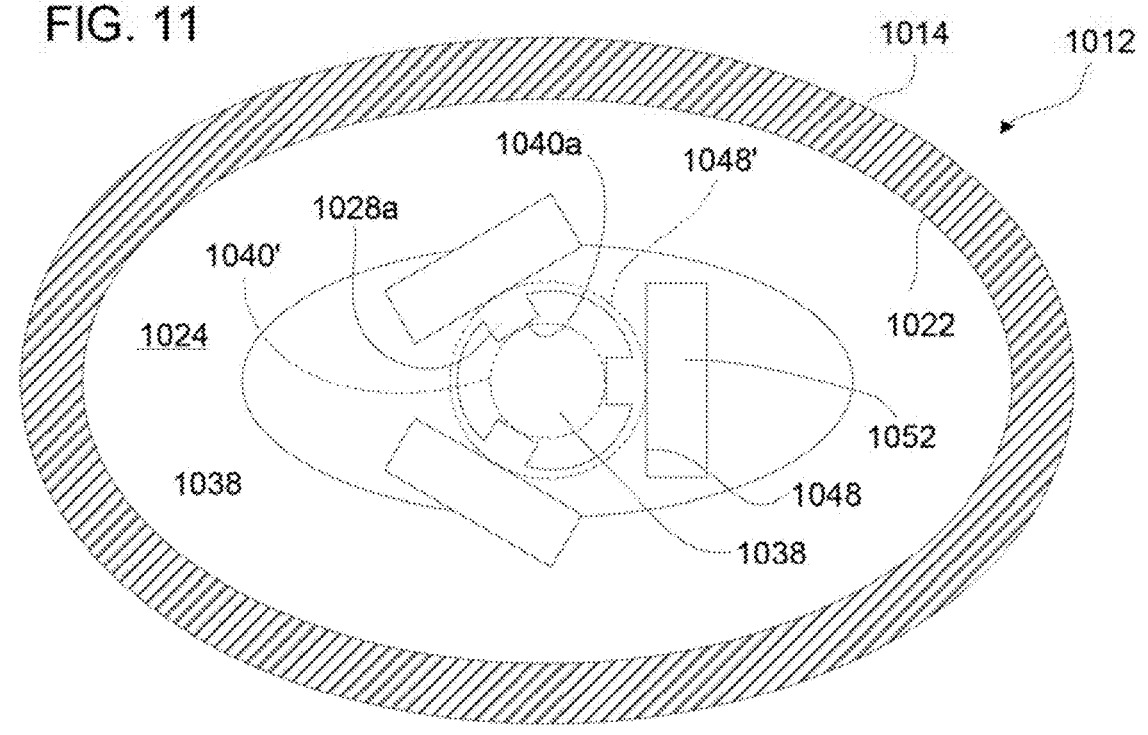
FIG. 11 is a cutaway view of an alternative embodiment of an introducer system, as viewed along the longitudinal axis of the introducer.

As noted above, the end wall passage 1038 may join the introducer end wall 1028 at multiple end wall edges 1040 to thereby define the axial stop ring 1040'. FIG. 11 shows an example of an introducer 1012 having such a construction, as viewed along the section XI-XI in FIG. 10A. Here, the introducer passage end wall 1028 is divided into three circumferentially spaced segments, each of which extends in a common plane perpendicular to the longitudinal axis 1016. Each end wall segment 1028 joins the end wall passage 1038 at a respective end wall edge segment 1040. (For clarity of illustration, only one of the three end wall segments 1028 and its respective end wall edge segment 1040 are marked with reference numbers.) The end wall edge segments 1040 collectively define an axial stop ring 1040'. In this case, there are three straight end wall edge segments 1040 arranged tangentially about a common center, but other numbers and shapes may be used (e.g., two end wall segments 1028 each having an arcuate end wall edge segment 1040, etc.).

FIG. 11 also illustrates an alternative configuration for a radial stop ring 1048'. In this case, the introducer has a probe receptacle 1050 formed by three generally flat walls, rather than the curved walls shown in FIG. 10B. Thus, the radial stop ring 1048' is defined by three straight intermediate wall edges 1048 arranged about the passage centerline.

In the embodiment of FIG. 11, and other embodiments in which the axial stop ring 1040' or radial stop ring 1048' is defined by a non-circular edge or arrangement of edges, the diameter of the stop ring 1040', 1048' is measured as the diameter of the largest circle that can fit within the inner boundary of the end wall edge(s) 1040 (for the axial stop ring 1040') or within the intermediate wall edge(s) 1048 (for a radial stop ring 1048').

Figure 12:
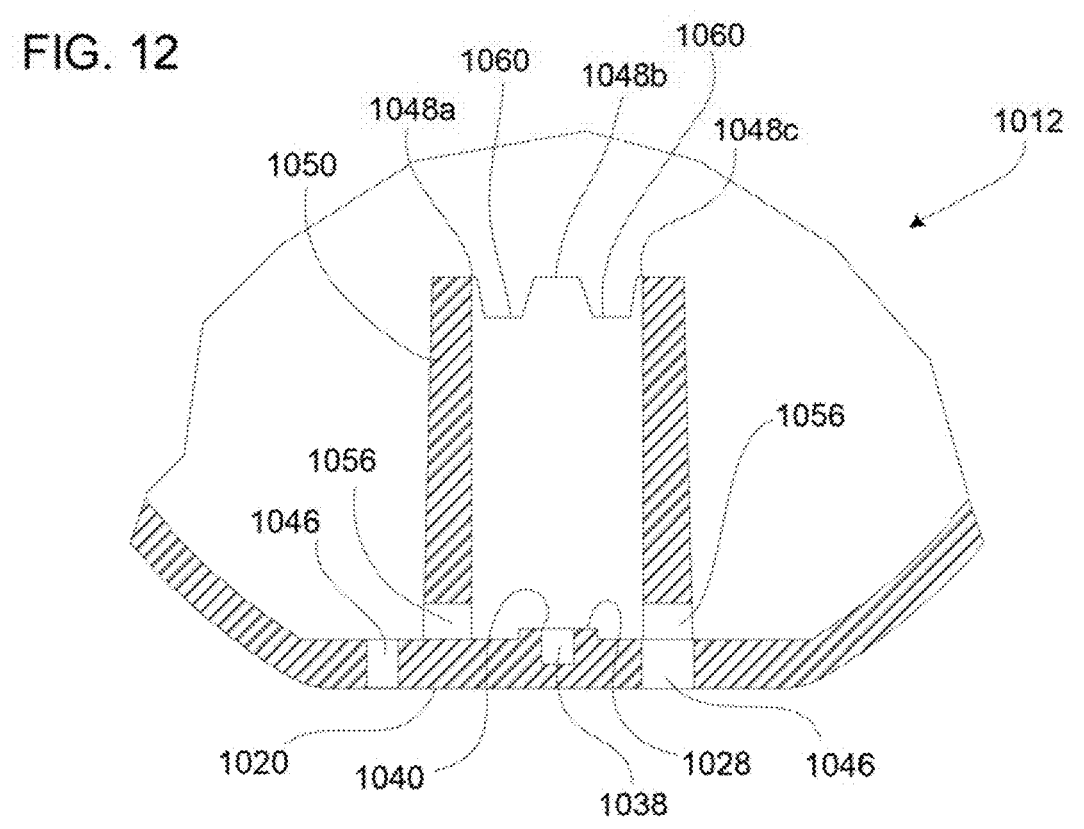
FIG. 12 is a cutaway view of the distal introducer end of another embodiment of an introducer system.

FIG. 12 illustrates another embodiment having various other modifications. In this case, the end wall passage 1038 does not extend all the way through the introducer wall. In addition, on the left-hand side, the introducer 1012 has an offset fluid passage 1046 located outside the confines of the probe receptacle 1050, and the probe receptacle has a lateral opening 1056 that allows fluid to pass from inside the receptacle 1050 to the offset fluid passage 1046. On the right-hand side, the introducer 1012 has an offset fluid passage 1046 and lateral opening 1056 that may be conveniently formed as a single void. For example, both the offset fluid passage 1046 and the lateral opening 1056 may be formed by a single operation of a drill, or by using an appropriately-shaped protrusion in a two-part molding assembly.

FIG. 12 also illustrates an example of an intermediate wall edge 1048 defined by discrete segments 1048a, 1048b,

1048c that are joined by connecting edges 1060. In this case, the discrete segments 1048a, 1048b, 1048c and connecting edges 1060 form a continuous series of intersecting edges, but only certain portions of the structure (i.e., segments 1048a, 1048b, 1048c) are positioned on a common plane to define a lateral stop ring 1048'.

Figure 13:
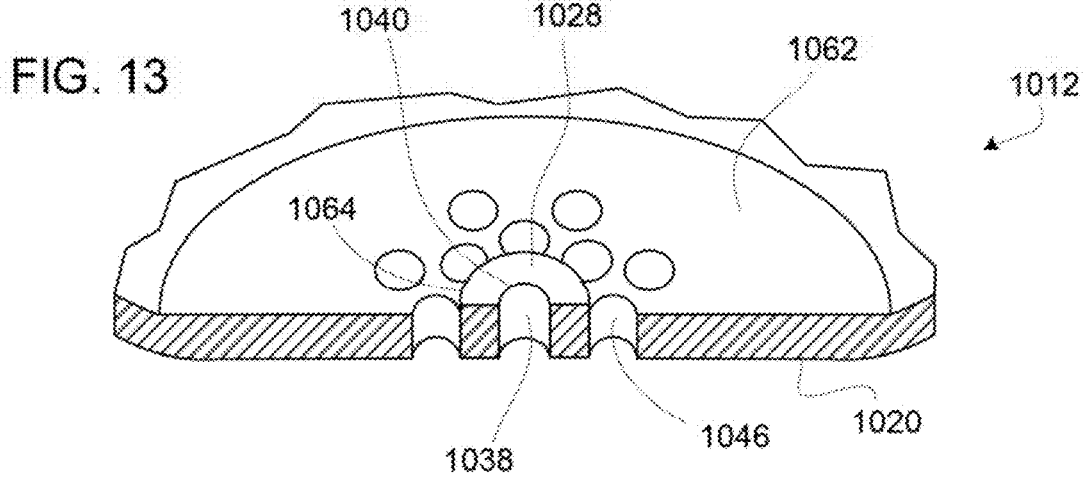
FIG. 13 is a cutaway view of the distal introducer end of another embodiment of an introducer system.

FIG. 13 shows another exemplary embodiment of an introducer 1012, which does not have a probe receptacle. In this example, the introducer passage end wall 1028 is surrounded by an outer end wall 1062. The outer end wall 1062 is located closer to the distal introducer end 1020 than the introducer passage end wall 1028. Thus, if a navigation probe 1002 is inserted into the introducer passage 1024 far enough to contact the outer end wall 1062, it must be pulled back in the proximal direction before the distal terminal end 1010 of the navigation probe 1002 can be inserted into the end wall passage 1038. Furthermore, the introducer passage end wall 1028 may join the outer end wall 1062 at a discrete longitudinally-extending step 1064, to make it difficult to slide the distal terminal end 1010 sideways into the end wall passage 1038. This structure may be used in conjunction with a probe clamp that inhibits locking until the navigation probe 1002 is properly seated in the axial stop ring 1040', in order to indicate when the probe 1002 is not properly installed. Such functionality will be apparent from the explanation provided below in relation to FIG. 17.

Figure 14:
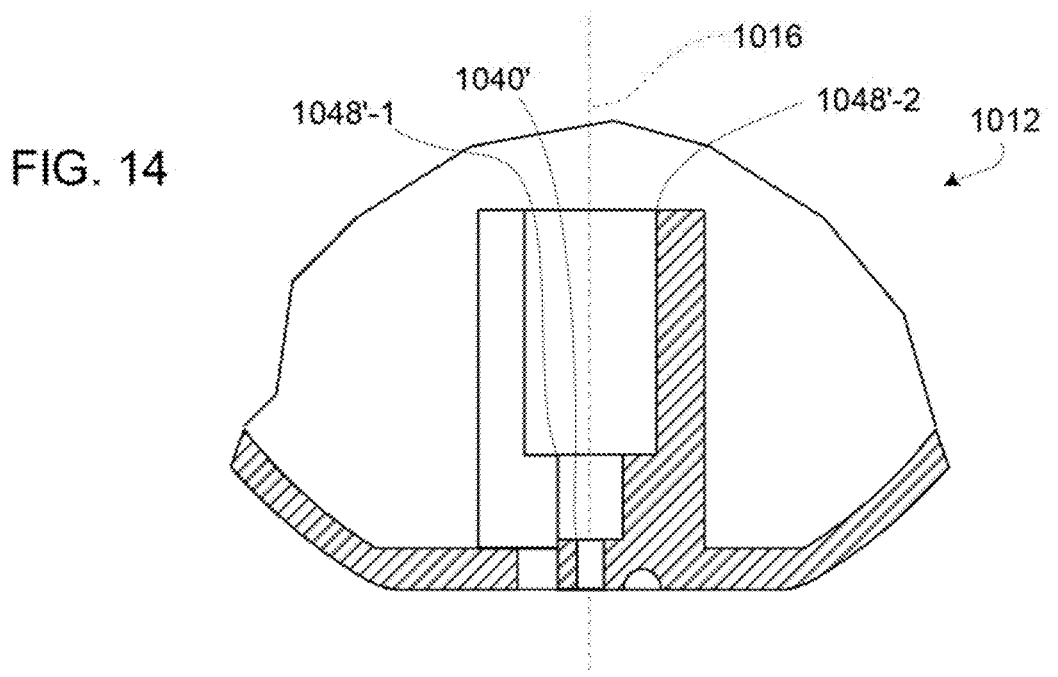
FIG. 14 is a cutaway view of the distal introducer end of another embodiment of an introducer system.

FIG. 14 shows another embodiment of an introducer 1012. In this case, the introducer 1012 has multiple radial stop rings 1048'-1, 1048'-2. The respective diameters of the radial stop rings 1048'-1, 1048'-2 increase as a function of a distance from the axial stop ring 1040' (i.e., the rings get larger towards the proximal introducer end 1018). Each radial stop ring 1048'-1, 1048'-2 also may have a respective diameter that is greater than the diameter of a portion of the navigation probe 1002 located within the plane of the respective radial stop ring 1048'-1, 1048'-2 when the navigation probe 1002 is inserted into contact with the axial stop ring 1040'. Thus, the navigation probe 1002 can be positioned such that it only contacts the axial stop ring 1040', by orienting the navigation probe 1002 along the longitudinal axis 1016.

Multiple radial stop rings 1048' may be provided by various manufacturing techniques. For example, in the embodiment of FIG. 14, the multiple radial stop rings 1048' may be formed by machining, such as drilling using a series of differently-sized drill bits or using a stepped drill bit. The embodiment of FIG. 14 also may be formed by two-part injection molding, with the mold movement direction being oriented along the longitudinal axis 1016.

Figure 15A:
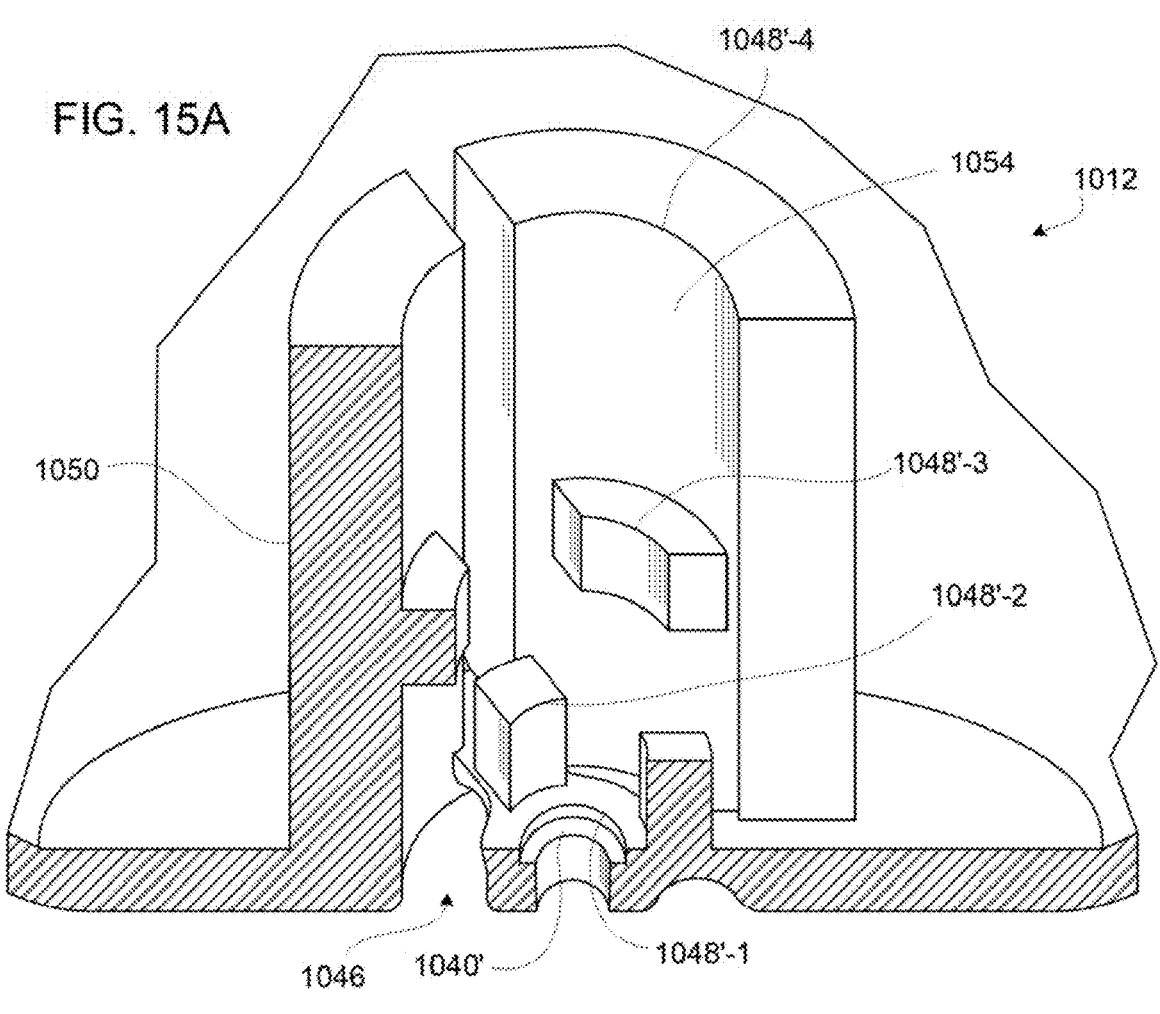
FIGS. 15A-15C are cutaway views of the distal introducer end of another embodiment of an introducer system in isometric view, side view, and front view, respectively.
Figure 15B:
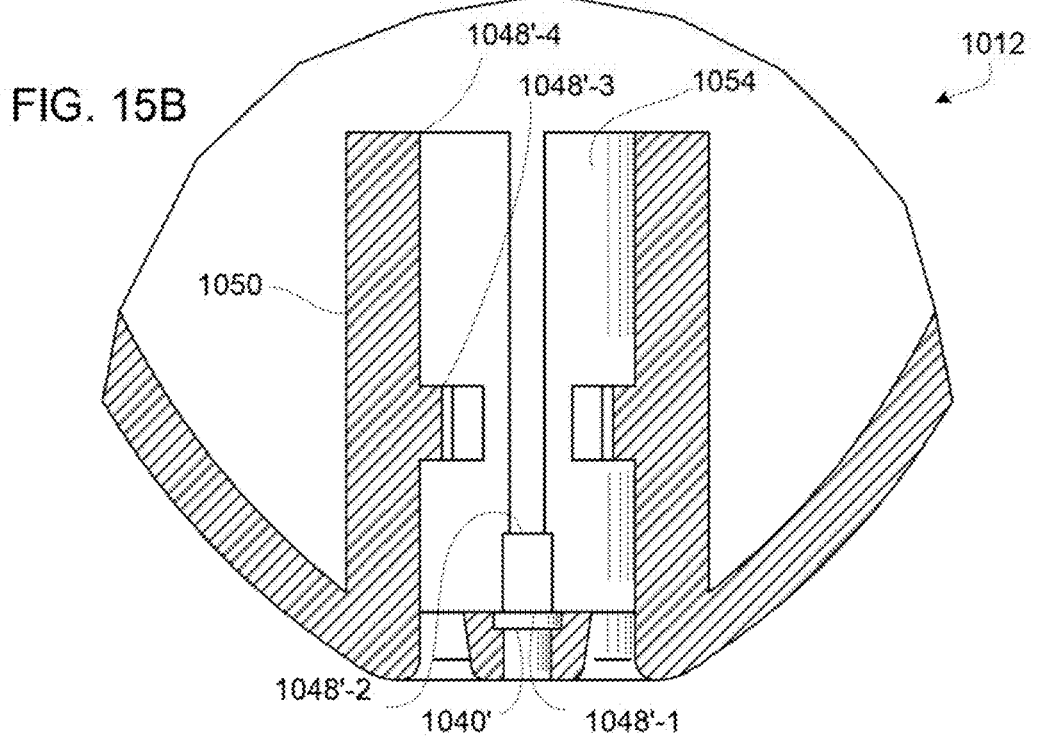
Figure 15C:
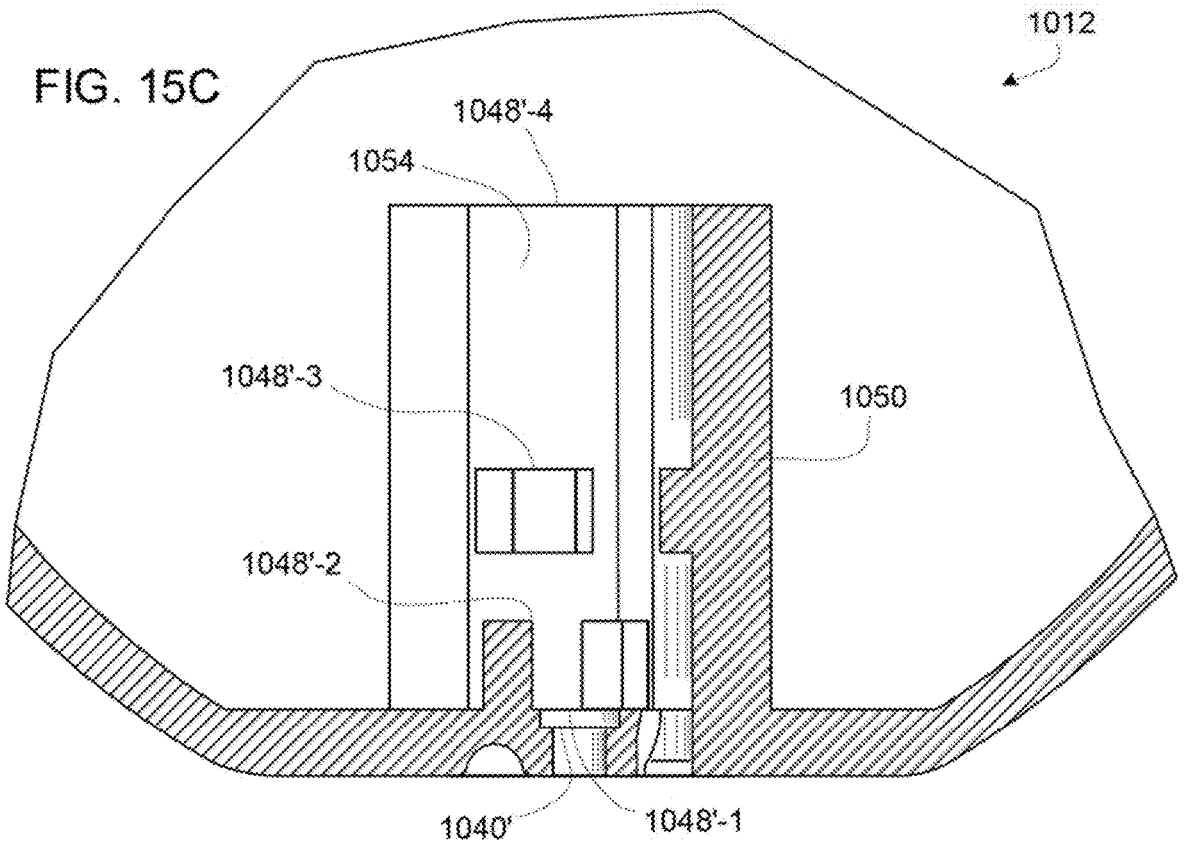

FIGS. 15A-15C show a variation on the embodiment of FIG. 14. In this case, the introducer 1012 has an axial stop ring 1040', and four radial stop rings 1048'-1, 1048'-2, 1048'-3, 1048'-4. The two most distal radial stop rings 1048'-1, 1048'-2 may be formed as stepped walls surrounding the axial stop ring 1040', and the most proximal radial stop ring 1048'-4 may be formed at the proximal end of a probe retainer 1050, such as described above. The remaining radial stop ring 1048'-3 may be conveniently formed as a radial protrusion from the inner surface 1054 of the probe receptacle 1050, by locating them directly above the offset fluid passages 1046, which allows fabrication by a two-part injection mold.

Embodiments having one or more radial stop rings 1048' may be configured to interact with and hold differently-shaped navigation probes 1002 in different ways. For example, the embodiment of FIGS. 15A-15C may be dimensioned such that some navigation probes can only be inserted far enough to contact the most distal radial stop ring 1048'-1, without contacting the axial stop ring 1040'. In this case, the most distal radial stop ring 1048'-1 acts as the axial stop ring for that type of navigation probe 1002. As another example, the radial stop rings 1048' may be configured such that all available navigation probes 1002 can be positioned into contact with the axial stop ring 1040', without contacting any of the radial stop rings 1048' (e.g., by aligning the probe 1002 with the longitudinal axis 1016). As still another example, one or more of the radial stop rings 1048' may be dimensioned to be in contact with a navigation probe 1002 having a particular geometry when the navigation probe tip 1008 is contacting the axial stop ring 1040' (e.g., one type of navigation probe 1002 may be dimensioned to simultaneously contact the entire proximal radial stop ring 1048'-4 while also contacting the axial stop ring 1040'). In this case, the combined contact provided by the axial stop ring 1040' and the radial stop ring 1048' can hold the navigation probe 1002 along the longitudinal axis 1016.

As a general matter, the axial stop ring 1040' (or whichever radial stop ring 1048' may be sized to act as an axial stop ring for a particular probe size) functions to stop the navigation probe 1002 at a fixed location along the longitudinal axis 1016, and the radial stop rings 1048' provide a boundary against excessive lateral movement of the probe. There is no continuous tapered surface between any radial stop ring 1048' and the axial stop ring 1040' (any tapered surface would be interrupted by the introducer passage end wall 1028 surrounding the axial stop ring 1040'). Thus, the structure relies on the tapered shape of the navigation probe tip 1008 to guide the navigation probe tip 1008 into the end wall passage 1038 and into contact with the axial stop ring 1040'.

Figures 16A, 16B:
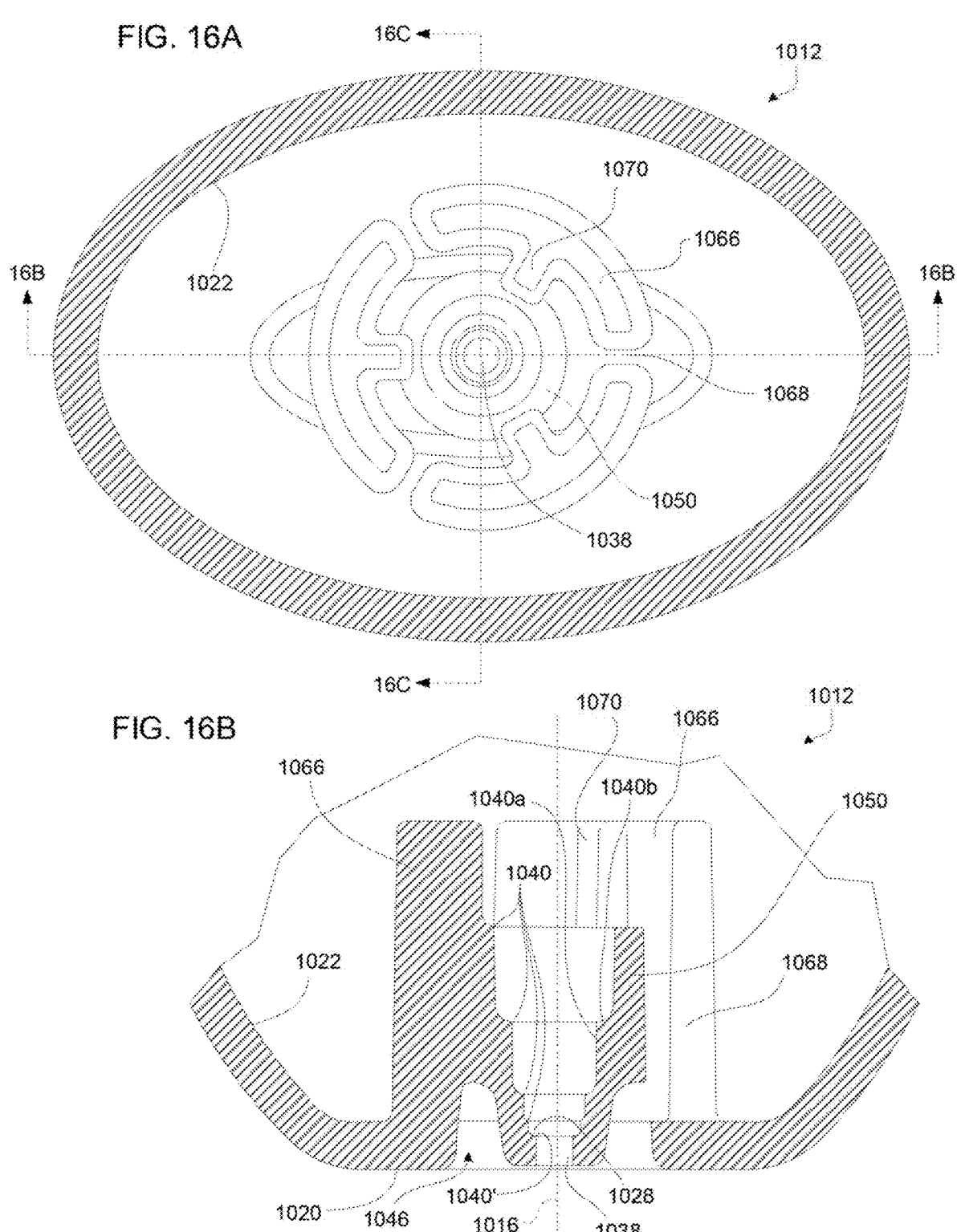
FIGS. 16A-16C are cutaway views of the distal introducer end of another embodiment of an introducer in top view, a view as seen along line 16B-16B of FIG. 16A, and a view as seen along line 16C-16C of FIG. 16A, respectively.
Figure 16C:
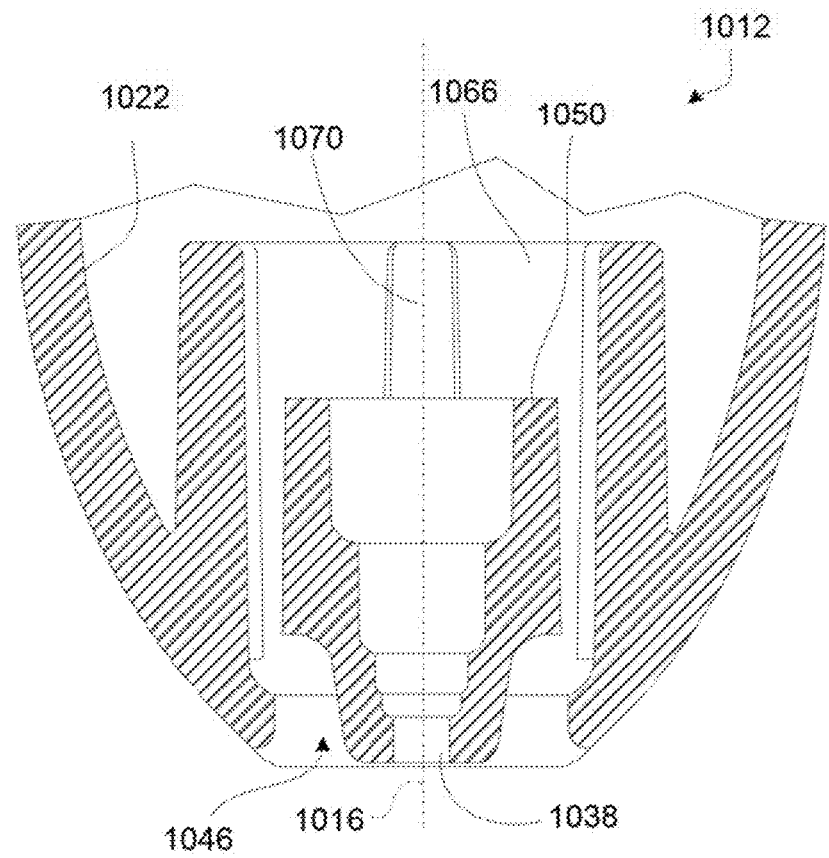

FIGS. 16A-16C show another embodiment of an introducer 1012, in which the axial stop ring 1040' and the adjacent introducer passage end wall 1028 are positioned within a probe receptacle 1050 having multiple axially-spaced end wall edges 1040. The probe receptacle 1050 comprises a continuous cylindrical body, and the end wall edges 1040 each extend continuously about the circumference of the cylindrical body (i.e., there are no radial slots or the like interrupting the probe receptacle 1050 or end wall edges 1040). However, other embodiments may include radial slots or the like. Also, some, and more preferably all, of the end wall edges 1040 may comprise an edge formed by surfaces that are oriented at an angle of approximately 85° to 90° relative to each other at the point of junction. For example, each end wall edge 1040 may be formed at an intersection of a generally cylindrical inner surface wall 1040a that extends along the longitudinal axis 1016, and a generally planar wall 1040b that extends perpendicular to the longitudinal axis 1016. Each planar wall 1040b also may join the other adjacent cylindrical wall 1040a (i.e., the cylindrical wall 1040a that is located further from the distal introducer end 1020 than the planar wall 1040b) with a beveled or radiused transition surface, such as shown. In this case, the end wall edges 1040 and transition surfaces preferably is dimensioned such that the navigation probe 1002 is unable to contact the transition surface due to interference with the end wall edges 1040.

As with the embodiments of FIGS. 14-15C, the respective diameters of the end wall edges 1040 increase as a function of distance from the distal introducer end 1020. The end wall edges 1040 may be selected such that each end wall edge 1040 acts as an axial stop ring for a particular type of navigation probe 1002. The end wall edges 1040 also may act as radial stop rings for navigation probes 1002 having a diameter that is smaller than the respective end wall edge 1040. Two or more of the end wall edges 1040 also may be configured to contact a single type of navigation probe 1002 at two locations when the navigation probe 1002 is fully-inserted into the introducer 1012. For example, the end wall edge 1040 closest to the distal introducer end 1020 may contact a spherical tip of the navigation probe 1002, and an end wall further away from the distal introducer end 1020 may contact the same navigation probe 1002 around the circumference of a tapered conical portion of the navigation probe 1002. Other alternatives and variations will be apparent to persons of ordinary skill in the art in view of the present disclosure.

In the embodiment of FIGS. 16A-16C the probe receptacle 1050 is attached to the rest of the introducer by a perimeter wall 1066 that surrounds the probe receptacle 1050 relative to the longitudinal axis 1016. The perimeter wall 1066 may have any suitable shape, such as the shown circular shape or an oval or rectilinear shape. The perimeter wall 1066 holds the probe receptacle 1050 over one or more fluid passages 1046 that lead out the distal introducer end 1020. The perimeter wall 1066 also may include one or more slots 1068 to allow fluid to pass between the fluid passages 1046 and the region of the introducer 1012 between the inner introducer wall 1022 and the outer wall of the perimeter wall 1066. The perimeter wall 1066 may be spaced radially from the probe receptacle 1050, and joined to it by inwardly-extending arms 1070 or the like.

Figure 17:
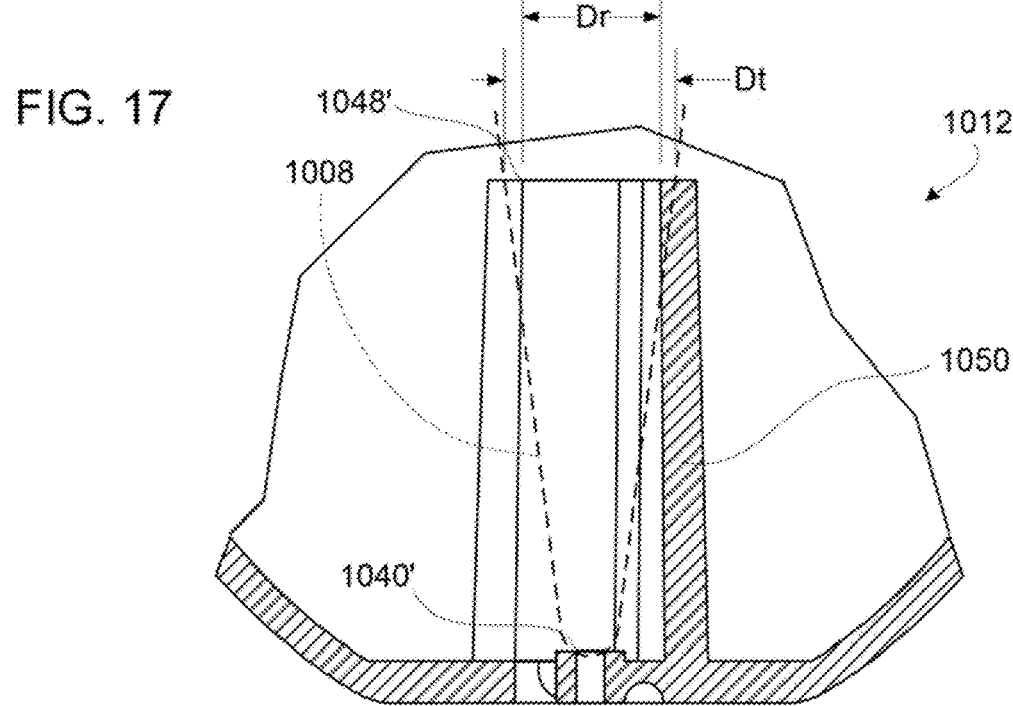
FIG. 17 is a cutaway view of the distal introducer end of another embodiment of an introducer system.

FIG. 17 shows another embodiment of an introducer 1012. In this case, the introducer 1012 has a structure forming an axial stop ring 1040', such as described above, and a probe recess 1050 with a radial stop ring 1048' that is dimensioned to interfere with insertion of the navigation probe 1002 into contact with the axial stop ring 1040'. More particularly, the diameter Dr of the radial stop ring 1048' is less than a diameter Dt of a portion of the navigation probe 1002 located within the plane of the radial stop ring 1048' when the distal probe tip 1008 is in contact with the axial stop ring 1040'. In this case, the probe recess 1050 is be configured to deflect away from the distal probe tip 1008 as the navigation probe 1002 is pushed into contact with the axial stop ring 1040'. This provides a self-centering function without requiring a continuously tapered wall from the radial stop ring 1048' to the axial stop ring 1040'. An advantage of this construction is that it avoids surface-to-surface contact between the navigation probe 1002 and the introducer 1012, thus avoiding large fluid movements that might be caused by such contact. Also, a surgeon can potentially tilt the navigation probe 1002 relative to the longitudinal axis 1016 while still keeping the navigation probe tip 1008 properly positioned in the axial stop ring 1040', by pressing sideways to bend the probe recess 1050 wall. The probe recess wall 1050 may include one or more slots or geometric shapes to facilitate such flexing. For example, the probe recess 1050 may be constructed of spaced flat walls, such as shown in FIG. 11.

Referring now to FIGS. 18-23, introducer systems 1000 such as those described herein may also include a probe retainer 1800 to selectively hold the navigation probe 1002 in relation to the introducer 1012. The probe retainer 1800 may be similar to the probe retainers 700 described above. For example, the probe retainer 1800 may have a receiver 1802 that is selectively affixed to the introducer 1212 by one or more clamps 1804. The receiver 1802 extends from proximal receiver end 1806 to a distal receiver end 1808, and has a receiver passage 1810 that is configured to receive the navigation probe shaft 1006. When the probe retainer 1800 is secured to the introducer 1212, the distal receiver end 1808 preferably extends within the introducer passage 1024, and is spaced from (out of contact with) the inner introducer sidewall 1022, and spaced from the introducer passage end wall 1028 and any probe receptacle 1050 or other structures that might be present in the introducer passage 1024. Thus, the distal receiver end 1808 is cantilevered within the introducer passage 1024. The proximal receiver end 1806 may extend in the proximal direction outside the introducer passage 1024, but this is not required.

In the shown example, the clamp 1804 comprises a pair of opposed clips 1812 that are each mounted to the receiver 1802 by one or more flexible arms 1814. The clamp 1804 is secured to the introducer 1012 by positioning the clips 1812 on the distal side of one or more ledges 1816 that extend radially from (or are recessed into) the proximal end of the retractor 1032. In this position, the arms 1814 (or other structures of the probe retainer 1800) are positioned against the proximal end 1018 of the introducer 1012. Thus, the clips 1812 simultaneously hold the introducer 1012 to the retractor 1032, and hold the receiver 1802 at a fixed position relative to the introducer 1012. The clips 1812 can be released by pressing against release arms 1818 to flex the arms 1814 and move the clips 1812 out of engagement with the ledges 1816.

The probe retainer 1800 also includes a lock 1820 that is movable between an unlocked position to allow the navigation probe shaft 1006 to move relative to the receiver passage 1810, and a locked position to fix the navigation probe shaft 1006 relative to the receiver passage 1810. The exemplary lock 1820 comprises a threaded lock nut 1820 that engages a corresponding threaded portion of the receiver 1802, to selectively collapse or expand the receiver passage 1810, as described above.

It will be appreciated that the clamp 1804 and lock 1820 may be replaced by any other suitable mechanism or mechanisms to hold the receiver 1802 in position relative to the introducer 1012.

The receiver passage 1810 is configured to position the navigation probe 1002 with its terminal end 1010 in contact with the axial stop ring 1040' when the probe retainer 1800 is secured to the introducer 1012, and the lock 1820 is in the locked position (i.e., when the parts are assembled into an introducing configuration). To this end, the receiver passage 1810 may extend concentrically along a receiver passage axis 1822 (see FIG. 20) that intersects the end wall passage 1038 when the probe retainer 1800 is secured to the proximal introducer end 1018.

The introducer system 1000 can be assembled into the introducing configuration by securing the probe retainer 1800 to the introducer 1012, sliding the navigation probe shaft 1006 down the receiver passage 1810 until the terminal end 1010 contacts the axial stop ring 1040', then moving the lock 1820 to the locked position to hold the navigation probe 1002 in place. Alternatively, the navigation probe 1002 can be installed in the probe retainer 1800 before securing the probe retainer 1800 to the introducer 1012.

The receiver passage 1810 may be configured to hold the navigation probe shaft 1008 with an amount of friction when the lock 1820 is unlocked. Such friction can be helpful to prevent the shaft 1008 from freely sliding along the receiver passage 1810 except when actively moved by a surgeon. Such friction can be provided, for example, by forming the receiver passage 1810 with tapered inner walls that converge towards the distal receiver end 1808 to a diameter less than the shaft diameter of the smallest navigation probe 1002 intended for use with the introducer system 1000, and forming slots in receiver 1802 to allow the tapered walls to flex radially outward when the probe shaft 1008 is inserted. Such flexing generates a restoring force, and thus friction, against the probe shaft 1008, to hold it against unwanted movement.

Figure 19:
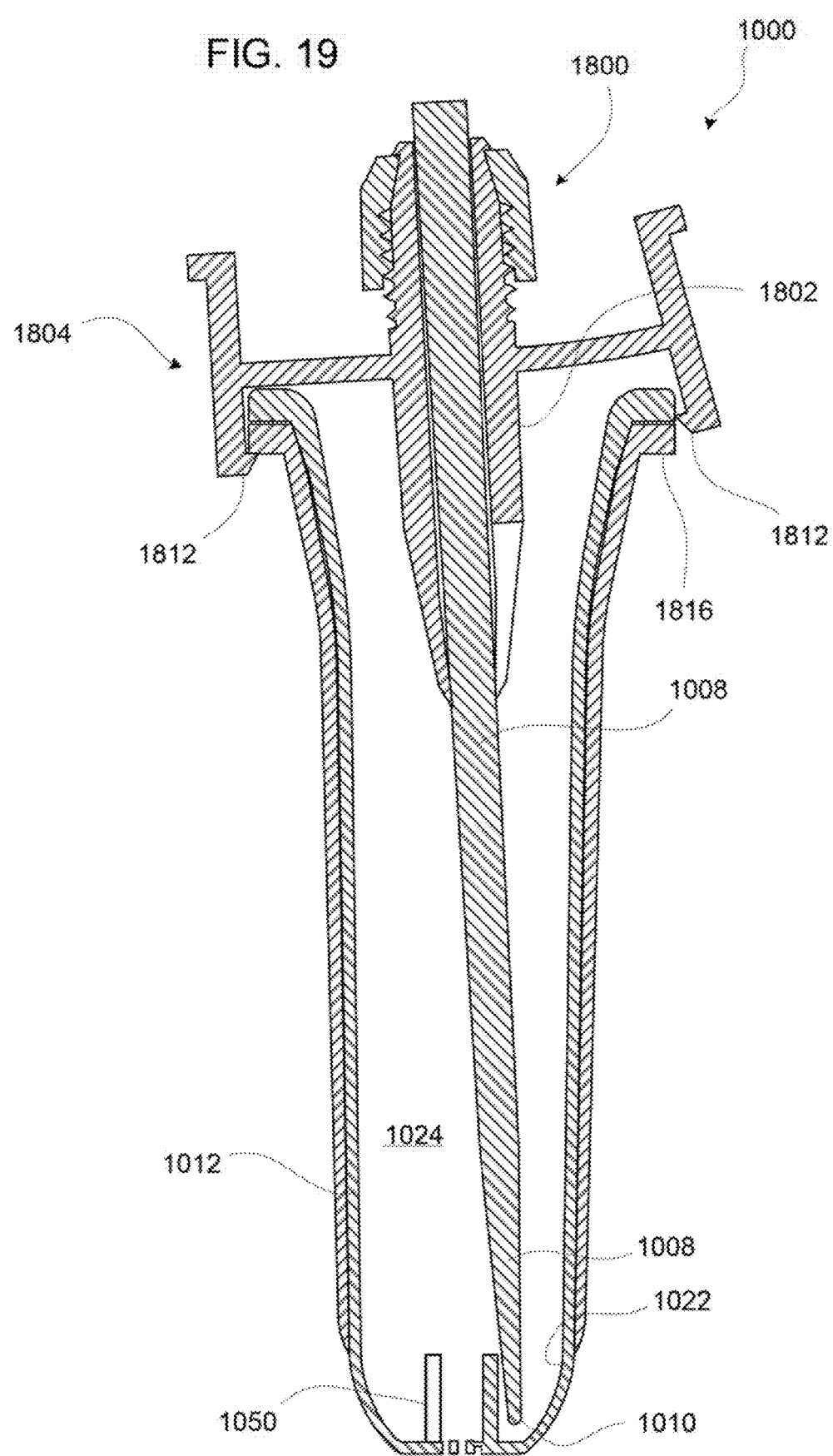
FIG. 19 is a cutaway side view of the embodiment of FIG. 17, shown in a different configuration.

The probe retainer 1800 also may be configured to prevent the terminal end 1010 of the navigation probe from being improperly placed within the introducer 1012. For example, as shown in FIG. 19, the clamp 1804 may be configured to prevent full installation if the terminal end 1010 is positioned outside a probe receptacle 1050 located at the distal end of the introducer channel 1024. More specifically, if the navigation probe 1002 and probe retainer 1800 are assembled together prior to being secured to the introducer 1012, it may be possible to position the terminal end 1010 between the inner introducer sidewall 1022 and the probe receptacle 1050. In this configuration, the navigation probe 1002 is not properly registered at the desired location within the introducer 1012. In this case, the probe receptacle 1050 holds the distal probe tip 1008 at an angle to the longitudinal axis 1016, and the probe shaft 1008 holds the receiver 1802 in a position in which the clamp 1804 cannot fully engage the introducer 1012. For example, as shown in FIG. 19, one of the clips 1812 may be positioned where it cannot engage the associated ledge 1816. Thus, the clamp 1804 is configured to prevent securement of the probe retainer 1800 to the introducer 1012 when the receiver passage axis 1822 is not oriented to intersect the end wall passage 1038. This provides a visible and tactile indication to the surgeon that the parts are not properly assembled, thus indicating that reassembly is required.

Figures 20, 21:
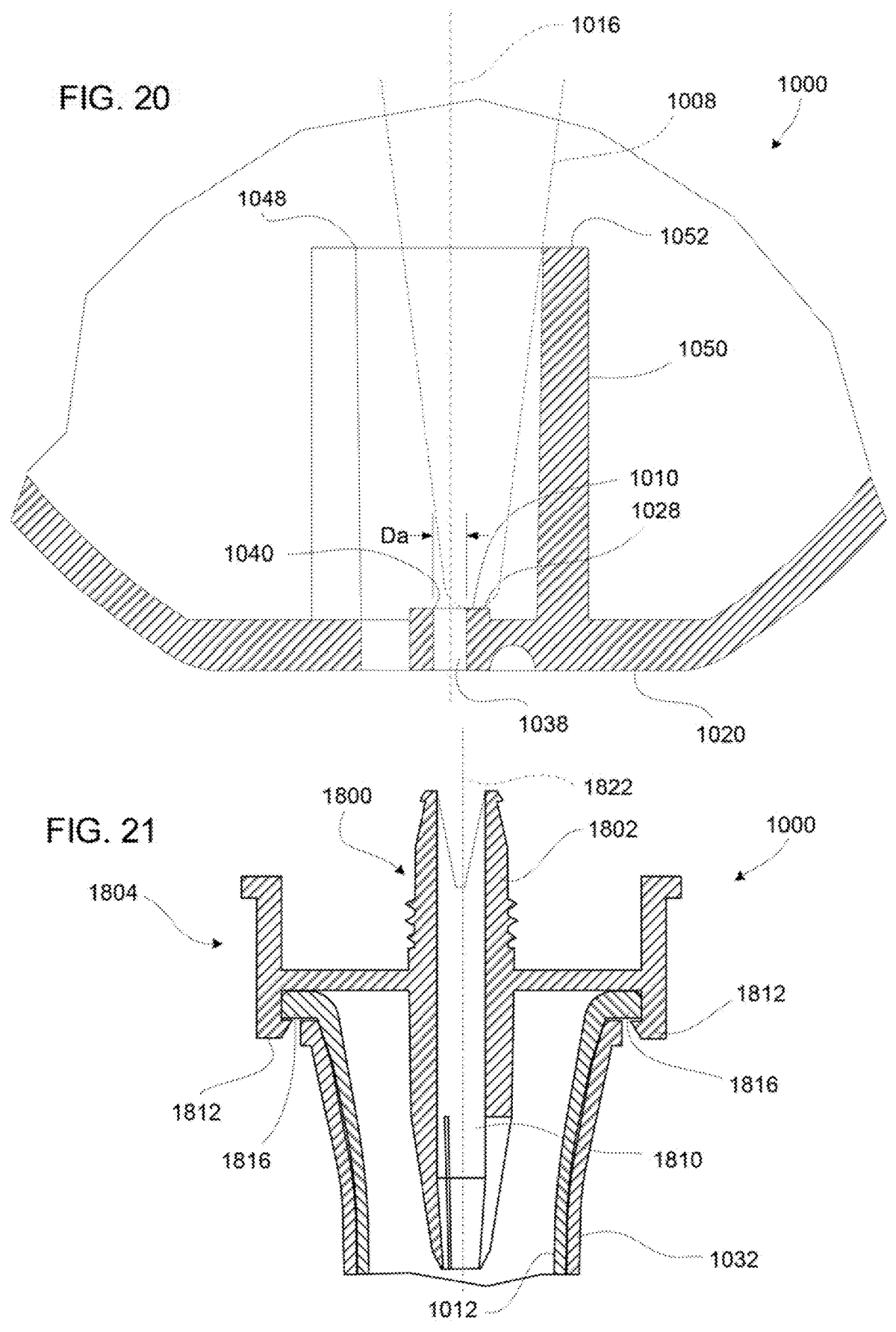

As noted above, the probe retainer 1800 holds the terminal end 1010 of the navigation probe 1002 against the axial stop ring 1040' when the lock 1820 is in the locked position. Prior to locking the lock 1820, it may be possible to tilt the probe shaft 1008 within the receiver passage 1810 such that the terminal end 1010 is in contact with the introducer passage end wall 1028 but not properly seated against the axial stop ring 1040'. This situation is shown in FIG. 20. Here, the terminal end 1010 of the navigation probe 1002 is not within the diameter Da of the axial stop ring 1040'. Movement of the navigation probe 1002 in the distal direction will be resisted by interaction between the terminal end 1010 and the end wall 1028, and the tapered outer wall of the navigation probe 1002 is not able to act against the end wall edges 1040 to guide the terminal end 1010 into the desired location within the end wall passage 1038. In this case, engaging the lock 1820 preferably re-centers the probe shaft 1008, and places the terminal end 1010 in the proper location along the longitudinal axis 1016. Upon doing so, the navigation probe 1002 is expected to snap into place with the distal end 1008 in contact with the axial stop ring 1040', but, even if the distal end 1008 is not fully engaged with the axial stop ring 1040', such distance is expected to be inconsequential for navigation purposes.

While the foregoing situation is not expected to present issues or deficiencies with the embodiment, it is also possible to configure the receiver 1002 to hold the navigation probe with the terminal end 1010 of the distal probe tip 1008 within the diameter Da of the axial stop ring 1040' when the probe retainer 1800 is secured to the proximal introducer end 1018, regardless of whether the lock 1820 is in the locked position or the unlocked position. Thus, it will not typically be possible during normal use to arrive at the situation shown in FIG. 20. This configuration may be obtained by, for example, creating preload on the lock 1820 to thereby hold the navigation probe shaft 1008 at two locations that are spaced apart along the receiver passage axis 1822, to prevent tilting relative to the receiver passage axis 1822. For example, referring to FIGS. 7A and 7B, the lock 1820 may have a threaded lock nut 714 that is fitted to the receiver 1802 with a preload that slightly compresses the proximal end of the receiver passage 1810 to move the inner surfaces 718 into engagement with the probe shaft 708, even when the lock is in the unlocked position. This preload can be achieved by positioning the retaining lip 720 to hold the lock nut 714 at a position to ensure some compression of the receiver passage 1810 even when the lock nut 714 is in its loosest position. Thus, the receiver passage 1810 effectively holds the probe shaft 1006 at or near both the proximal receiver end 1806 and the distal receiver end 1808 to hold it in a proper orientation at all times. A similar preload can be provided in the embodiment of FIGS. 9A and 9B by positioning the hooks 926 to hold the nut 914 at a position in which the tapered distal end 920 of the nut 914 compresses slightly to center the probe shaft 1008. Other alternatives and variations will be apparent to persons of ordinary skill in the art in view of the present disclosure.

FIG. 21 shows an alternative embodiment of an introducer system 1000. The lock 1820 and other parts are omitted for clarity. This embodiment is similar to the embodiment of FIG. 18, but the clips 1812 of the clamp 1804 are configured to engage ledges 1816 located on the introducer 1012, rather than the retractor 1032. This allows assembly of the introducer 1012, probe retainer 1800 and navigation probe 1002 into a unit that can be attached to and removed from the retractor 1032.

Figure 22:
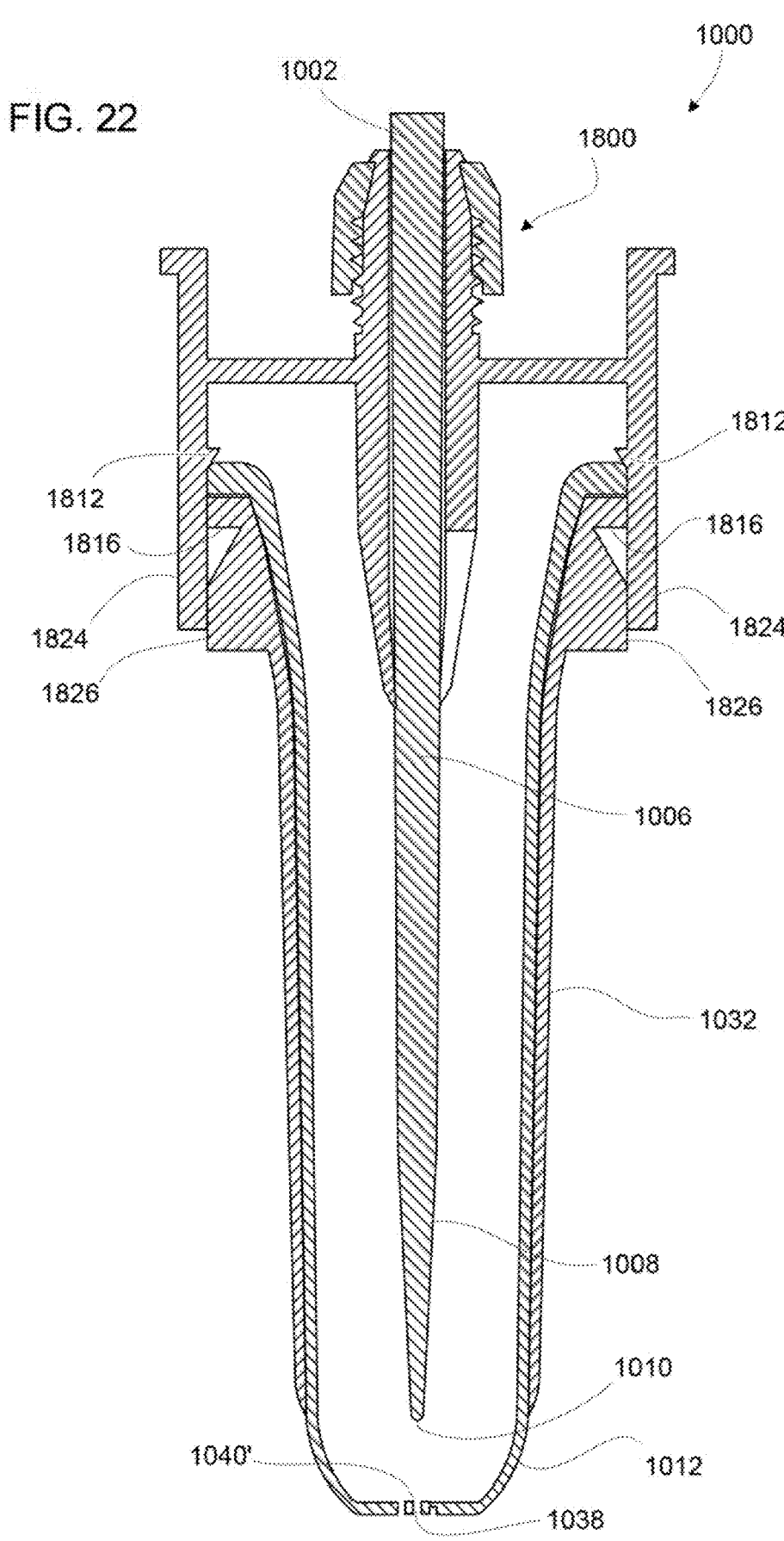
FIG. 22 a cutaway side view of another exemplary embodiment of an introducer system, including a probe retainer, shown with the probe retainer partially inserted to the installed position.
Figure 23:
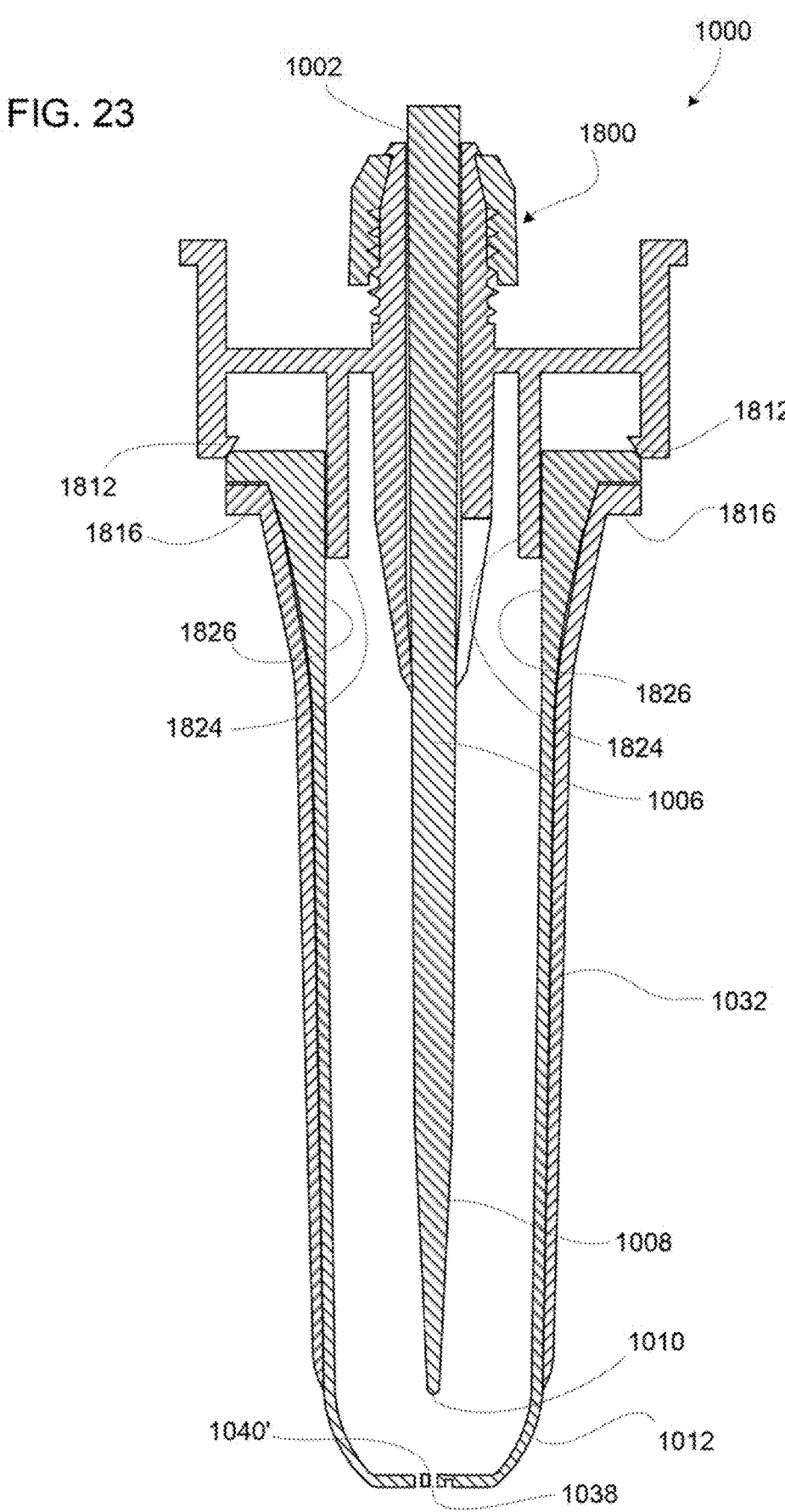
FIG. 23 a cutaway side view of another exemplary embodiment of an introducer system, including a probe retainer, shown with the probe retainer partially inserted to the installed position.

FIGS. 22 and 23 show two other alternative embodiments of introducer systems 1000, in which the probe retainer 1800 and one or both of the introducer 1012 and retractor 1032 are provided with insertion guides to ensure proper guidance of the navigation probe 1002 into engagement with axial stop ring 1040' and assembly into the introducing configuration. In the case of FIG. 22, the clamp 704 includes first guide walls 1824 that extend distally from each clip 1812 along the longitudinal axis 1016. The first guide walls 1824 are positioned to surround and slide along respective second guide walls 1826 provided on the introducer 1012 and/or retractor 1032. The first and second guide walls 1824, 1826 are dimensioned to align the receiver 1802 passage axis 1822 to intersect the end wall passage 1038 before the probe retainer 1800 reaches the point where the clips 1812 engage with the ledges 1816. In FIG. 23, the first guide walls 1824 are provided on the clamp arms 1814, and the second guide walls 1826 are provided on the inner introducer sidewall 1022. In each case, the insertion guides align the navigation probe 1002 with the end wall passage 1038, which helps avoid situations like the one described in relation to FIG. 19.

The embodiments of FIGS. 22 and 23 both have introducers 1012 that lack probe receptacles 1050. However, if a probe receptacle 1050 is provided, the probe receptacle preferably terminates at a proximal receptacle end that is positioned such that the insertion guides properly orient the probe 1002 towards the end wall passage 1038 before the probe's terminal end 1010 reaches the proximal receptacle end, thus eliminating the possibility of the probe tip being positioned radially outside the probe receptacle 1050.

It will be understood that the features described in relation to the foregoing embodiments may be reconfigured and used with other embodiments. For example, a probe retainer 1800 as described in relation to FIG. 18 may be modified in all of the ways described in relation to the probe retainers 700, 900 described elsewhere herein. Similarly, features and modification shown in embodiments of one Figure may be used in any other embodiment, as may be desired to provide a useful effect. Other alternatives and variations will be apparent to persons of ordinary skill in the art in view of the present disclosure.

The present disclosure describes a number of new, useful and nonobvious features and/or combinations of features that may be used alone or together. The embodiments described herein are all exemplary, and are not intended to limit the scope of the inventions. It will be appreciated that the inventions described herein can be modified and adapted in various and equivalent ways, and all such modifications and adaptations are intended to be included in the scope of this disclosure and the appended claims.

We claim:

1. A surgical access port assembly comprising:
   a shaft retainer comprising:
      a receiver having:
         a receiver channel extending in a longitudinal direction and configured to receive a shaft in a proximal open end of the receiver channel, and limit movement of the shaft in a lateral direction that is perpendicular to the longitudinal direction, and
         a first threaded surface, and
      a lock having:
         a central passage extending in the longitudinal direction, and
         a second threaded surface,
      wherein:
         the lock and receiver are movable between a first configuration in which the lock and receiver allow the shaft to move relative to the lock and receiver along the longitudinal direction, and a second configuration in which the lock and receiver prevent the shaft from moving relative to the lock and receiver along the longitudinal direction, and
         the lock is rotatable relative to the receiver to engage the first threaded surface with the second threaded surface to thereby move the lock and receiver between the first configuration and the second configuration;
   an introducer extending along the longitudinal direction from a proximal introducer end to a distal introducer end, the distal introducer end defining a tapered outer surface that reduces in size in a distal direction extending away from the proximal introducer end; and
   a retractor removably attached to the introducer, the retractor comprising a retractor sidewall defining a hollow retractor passage extending from a proximal retractor end to a distal retractor end, wherein the retractor is configured to selectively secure to a remainder of the surgical access port assembly with the tapered outer surface of the introducer extending in the longitudinal direction distally beyond the distal retractor end, and wherein the hollow retractor passage has a retractor passage cross-sectional profile as viewed along the longitudinal direction, wherein the retractor passage cross-sectional profile comprises an elongated non-circular shape.

2. The surgical access port assembly of claim 1, wherein the retractor passage cross-sectional profile is oval.

3. The surgical access port assembly of claim 2, wherein the retractor passage cross-sectional profile is elliptical.

4. The surgical access port assembly of claim 2, wherein the retractor passage cross-sectional profile is oval entirely from the proximal retractor end to the distal retractor end.

5. The surgical access port assembly of claim 1, wherein the introducer comprises an introducer sidewall defining a hollow introducer passage extending from the proximal introducer end to the distal introducer end.

6. The surgical access port assembly of claim 5, wherein the hollow introducer passage has an introducer passage cross-sectional profile, as viewed along the longitudinal direction, wherein the introducer passage cross-sectional profile matches the elongated non-circular shape of the retractor passage cross-sectional profile, at least in a portion of the hollow introducer passage located within the hollow retractor passage when the introducer is attached to the retractor.

7. The surgical access port assembly of claim 5, wherein:

the retractor sidewall has a uniform retractor sidewall thickness from a first location adjacent to the proximal retractor end to a second location adjacent to the distal retractor end;

the introducer sidewall comprises a uniform introducer sidewall thickness in at least a portion of the hollow introducer passage located from the first location to the second location when the introducer is attached to the retractor.

8. The surgical access port assembly of claim 5, wherein the hollow introducer passage has an introducer passage cross-sectional profile as viewed along the longitudinal direction, wherein the introducer passage cross-sectional profile is oval entirely from the proximal introducer end to the distal introducer end.

9. The surgical access port assembly of claim 8, wherein the introducer further comprises a receptacle wall extending within the hollow introducer passage from the distal introducer end towards the proximal introducer end, the receptacle wall comprising one or more inner surfaces defining a receptacle.

10. The surgical access port assembly of claim 9, wherein the one or more inner surfaces define a circular cross-sectional shape as viewed along the longitudinal direction.

11. The surgical access port assembly of claim 10, wherein the circular cross-sectional shape tapers to reduce in size away towards the distal introducer end.

12. The surgical access port assembly of claim 10, wherein the circular cross-sectional shape comprises at least two stepped cylindrical wall segments.

13. The surgical access port assembly of claim 9, wherein the receptacle wall comprises one or more axial slots configured to permit fluid to flow radially though the receptacle wall.

14. The surgical access port assembly of claim 9, wherein the introducer comprises one or more openings at the distal introducer end, wherein the one or more openings are in fluid communication with the hollow introducer passage without passing through the receptacle.

15. The surgical access port assembly of claim 9, wherein the receiver extends into the hollow introducer passage and terminates at a distal receiver end that is spaced proximally from the receptacle wall when the shaft retainer is attached to the introducer.

16. The surgical access port assembly of claim 5, wherein the shaft retainer is removably connected to the introducer at the proximal introducer end by one or more releasable clamps, and wherein the one or more releasable clamps do not block an entirety of the hollow introducer passage at the proximal introducer end.

17. The surgical access port assembly of claim 1, wherein the retractor sidewall comprises a transparent material.

18. The surgical access port assembly of claim 1, wherein the distal introducer end comprises a transparent material.

19. The surgical access port assembly of claim 1, wherein the receiver channel comprises one or more slots extending along the longitudinal direction.

20. The surgical access port assembly of claim 19, wherein:

at least one of the receiver and the lock comprises a tapered surface;

the one or more slots extend radially thought the tapered surface; and when the lock and the receiver are in the second configuration, the tapered surface is configured to compress an inner surface of the receiver channel against the shaft.

* * * * *